US009718766B2

(12) United States Patent
Yu et al.

(10) Patent No.: US 9,718,766 B2
(45) Date of Patent: Aug. 1, 2017

(54) HIGH PENETRATION DRUGS AND THEIR COMPOSITIONS THEREOF FOR TREATMENT OF PARKINSON DISEASES

(71) Applicant: Techfields Pharma Co., Ltd., Suzhou (CN)

(72) Inventors: Chongxi Yu, Plainfield, IL (US); Lina Xu, Jiangsu (CN)

(73) Assignee: Techfields Pharma Co., Ltd., Suzhou, Jiangsu (CN)

( * ) Notice: Subject to any disclaimer, the term of this patent is extended or adjusted under 35 U.S.C. 154(b) by 0 days.

(21) Appl. No.: 14/854,616

(22) Filed: Sep. 15, 2015

(65) Prior Publication Data

US 2016/0002157 A1   Jan. 7, 2016

Related U.S. Application Data

(63) Continuation of application No. PCT/CN2013/072728, filed on Mar. 15, 2013.

(51) Int. Cl.
*A61K 31/195* (2006.01)
*C07C 219/06* (2006.01)
*C07C 317/44* (2006.01)
*A61K 31/137* (2006.01)
*C07C 229/36* (2006.01)
*A61K 31/198* (2006.01)
*A61K 31/277* (2006.01)
*C07C 271/16* (2006.01)
*C07C 271/22* (2006.01)
*C07D 321/12* (2006.01)
*C07C 219/10* (2006.01)
*C07C 219/14* (2006.01)
*C07C 219/28* (2006.01)
*C07C 229/12* (2006.01)
*C07C 327/30* (2006.01)
*C07C 229/58* (2006.01)
*C07D 455/02* (2006.01)
*C07D 471/04* (2006.01)
*C07C 237/06* (2006.01)
*C07C 237/20* (2006.01)
*C07D 207/16* (2006.01)
*C07K 5/083* (2006.01)
*C07D 211/62* (2006.01)
*C07K 5/097* (2006.01)
*A61K 31/197* (2006.01)
(Continued)

(52) U.S. Cl.
CPC .......... *C07C 317/44* (2013.01); *A61K 31/137* (2013.01); *A61K 31/195* (2013.01); *A61K 31/197* (2013.01); *A61K 31/198* (2013.01); *A61K 31/24* (2013.01); *A61K 31/40* (2013.01); *C07C 219/06* (2013.01); *C07C 219/10* (2013.01); *C07C 219/14* (2013.01); *C07C 219/28* (2013.01); *C07C 219/32* (2013.01); *C07C 229/12* (2013.01); *C07C 229/36* (2013.01); *C07C 229/58* (2013.01); *C07C 237/06* (2013.01); *C07C 237/08* (2013.01); *C07C 237/20* (2013.01); *C07C 271/16* (2013.01); *C07C 271/22* (2013.01); *C07C 327/30* (2013.01); *C07C 327/36* (2013.01); *C07D 207/16* (2013.01); *C07D 211/62* (2013.01); *C07D 321/12* (2013.01); *C07D 455/02* (2013.01); *C07D 471/04* (2013.01); *C07K 5/0806* (2013.01); *C07K 5/0823* (2013.01); *C07C 2102/08* (2013.01)

(58) Field of Classification Search
CPC .... A61K 31/195; C07C 219/06; C07C 229/36
See application file for complete search history.

(56) References Cited

U.S. PATENT DOCUMENTS 3,939,253 A    2/1976 Bodor et al.
4,311,706 A    1/1982 Bodor et al.
(Continued)

FOREIGN PATENT DOCUMENTS

CN    1470506 A    1/2004
CN    101478971 A    7/2009
(Continued)

OTHER PUBLICATIONS

Hobbs et al (2009): STN International, HCAPLUS database (Columbus, Ohio), Accession No. 2009: 198484.*
Barcia et al., "Inflammation and Parkinson's Disease," *Parkinson's Disease*, vol. 2011, Article ID 729054, 2 pages (2011).
Berge et al., "Pharmaceutical Salts," *Journal of Pharmaceutical Sciences*, 66(1): 1-19 (1977).
Bodor et al., "Improved Delivery through Biological Membranes. 4. Prodrugs of L-Dopa," *J. Med. Chem.*, 20 (11): 1435-1445 (1977).
Cools, "Dopaminergic modulation of cognitive function-implications for L-DOPA treatment in Parkinson's disease," *Neuroscience & Biobehavioral Reviews*, 30: 1-23 (2006).
Gao et al., "Novel anti-inflammatory therapy for Parkinson's disease," *Trends Pharmacol Sci.*, 24(8):395-401 (2003).
(Continued)

*Primary Examiner* — Golam M M Shameem
(74) *Attorney, Agent, or Firm* — Finnegan, Henderson, Farabow, Garrett & Dunner LLP

(57) ABSTRACT

One aspect of the invention provides a composition of novel high penetration compositions (HPC) or a high penetration prodrug (HPP) for treatment of Parkinson's disease. The HPCs/HPPs are capable of being converted to parent active drugs or drug metabolites after crossing the biological barrier and thus can render treatments for the conditions that the parent drugs or metabolites can. Additionally, the HPPs are capable of reaching areas that parent drugs may not be able to access or to render a sufficient concentration at the target areas and therefore render novel treatments. The HPCs/HPPs can be administered to a subject through various administration routes, e.g., locally delivered to an action site of a condition with a high concentration or systematically administered to a biological subject and enter the general circulation with a faster rate.

9 Claims, 16 Drawing Sheets

(51) Int. Cl.
    *A61K 31/24*     (2006.01)
    *A61K 31/40*     (2006.01)
    *C07C 219/32*     (2006.01)
    *C07C 237/08*     (2006.01)
    *C07C 327/36*     (2006.01)

(56) References Cited

U.S. PATENT DOCUMENTS

| | | | | |
|---|---|---|---|---|
| 7,829,592 B2* | 11/2010 | Xiang | ................... | C07C 229/36 |
| | | | | 514/533 |
| 8,324,273 B2* | 12/2012 | Xiang | ................... | C07C 229/36 |
| | | | | 514/533 |
| 8,377,986 B2* | 2/2013 | Hobbs | ........................... | 514/533 |
| 2010/0069336 A1 | 3/2010 | Yu et al. | | |

FOREIGN PATENT DOCUMENTS

| | | |
|---|---|---|
| CN | 101687792 A | 3/2010 |
| DE | 2153813 A | 10/1971 |
| DE | 2338350 A1 | 2/1974 |
| JP | A-S50-029527 | 3/1975 |
| JP | A-H21-2009-527467 | 7/2009 |
| JP | A-H21-2009-542797 | 12/2009 |
| JP | A-H21-2009-543857 | 12/2009 |
| JP | A-H21-2009-544685 | 12/2009 |
| JP | A-H22-2010-500989 | 1/2010 |
| JP | A-H22-2010-502583 | 1/2010 |
| JP | A-H22-2010-505936 | 2/2010 |
| JP | A-H22-2010-529101 | 8/2010 |
| JP | A-H23-2011-522035 | 7/2011 |
| JP | A-H24-2012-511027 | 5/2012 |
| JP | A-H24-2012-526055 | 10/2012 |
| JP | A-H24-2012-529443 | 11/2012 |
| WO | WO 2007/117687 A2 | 10/2007 |
| WO | WO 2008/012603 A1 | 1/2008 |
| WO | WO 2008/012605 A1 | 1/2008 |
| WO | WO 2008/017903 A1 | 2/2008 |
| WO | WO 2008/029199 A1 | 3/2008 |
| WO | WO2008/079387 A1 | 7/2008 |
| WO | WO 2008/149181 A1 | 12/2008 |
| WO | WO 2009/022098 A1 | 2/2009 |
| WO | WO2009/101616 A1 | 8/2009 |
| WO | WO 2010/065936 A1 | 6/2010 |
| WO | WO2011/008675 A2 | 1/2011 |

OTHER PUBLICATIONS

Jankovic, "Parkinson's disease: clinical features and diagnosis," *J Neurol Neurosurg Psychiatry*, 79: 368-376 (2008).

Obeso et al., "Functional Organization of the Basal Ganglia: Therapeutic Implications for Parkinson's Disease," *Mov Disord.*, 23(Suppl 3): S548-S559 (2008).

Parkinson's Disease—National Clinical Guideline for Diagnosis and Management in Primary and Secondary Care, NICE Clinical Guidelines, No. 35, National Collaborating Centre for Chronic Conditions (UK), London: Royal College of Physicians (UK) (2006).

International Search Report for International Application No. PCT/CN2013/072728, dated Dec. 19, 2013 (6 pages).

International Preliminary Report on Patentability for International Application No. PCT/CN2013/072728, dated Sep. 15, 2015 (7 pages).

Extended European Search Report for European Patent Application No. EP 13878173, dated Mar. 14, 2017 (17 pages).

* cited by examiner

US 9,718,766 B2

HIGH PENETRATION DRUGS AND THEIR COMPOSITIONS THEREOF FOR TREATMENT OF PARKINSON DISEASES

PRIORITY CLAIM

This application is a continuation of International Patent Application No. PCT/CN/13/72728, filed Mar. 15, 2013, which is incorporated by reference herein in its entirety, including the drawings.

FIELD OF THE INVENTION

The invention relates to the field of pharmaceutical compositions. More specifically, one aspect of the invention relates to pharmaceutical compositions capable of penetrating one or more biological barriers and methods of using the pharmaceutical compositions for preventing and/or treating Parkinson's disease and/or Parkinsonian syndromes in a subject.

BACKGROUND OF THE INVENTION

Parkinson's disease (PD) is a neurological disorder characterized by a degeneration of dopamine neurons in the substantia nigra and a loss of dopamine in the putamen. It is described as a motor disease, but it also produces cognitive and behavioral symptoms. Parkinson's disease may result from the death of dopamine-generation cells in the substatia nigra, a region of the midbrain. The cause of this cell death may be unknown (primary parkisonism) or known (secondary parkinsonism). Parkinson's disease may cause many symptoms in a wide variety of functions including movement, attention and learning. The primary symptoms of Parkinson's disease result from reduced activity of dopamine-secreting cells caused by cell death in the pars compacta region of the substantia nigra. A particular conceptual model of the motor circuit and its alteration with PD has been of great influence since 1980, although some limitations have been pointed out which have led to modifications [Obeso J A, Rodriguez-Oroz M C, Benitez-Temino B, et al. (2008). "Functional organization of the basal ganglia: therapeutic implications for Parkinson's disease". *Mov. Disord.* 23 (Suppl 3): S548-59]. In this model, the basal ganglia normally exert a constant inhibitory influence on a wide range of motor systems, preventing them from becoming active at inappropriate times. When a decision is made to perform a particular action, inhibition is reduced for the required motor system, thereby releasing it for activation. Dopamine acts to facilitate this release of inhibition, so high levels of dopamine function tend to promote motor activity, while low levels of dopamine function, such as occur in PD, demand greater exertions of effort for any given movement. Thus the net effect of dopamine depletion is to produce hypokinesia [Obeso J A, Rodriguez-Oroz M C, Benitez-Temino B, et al. (2008). "Functional organization of the basal ganglia: therapeutic implications for Parkinson's disease". *Mov. Disord.* 23 (Suppl 3): S548-59].

The main families of drugs known for treating motor symptoms are levodopa (usually combined with a dopa decarboxylase inhibitor or COMT inhibitor), dopamine agonists and MAO-B inhibitors [The National Collaborating Centre for Chronic Conditions, ed. (2006). "Symptomatic pharmacological therapy in Parkinson's disease", *Parkinson's Disease*. London: Royal College of Physicians. pp. 59-100]. Levodopa is well known to improve motor symptoms but its effects in cognitive and behavioral symptoms are more complex [Cools R (2006). "Dopaminergic modulation of cognitive function-implications for L-DOPA treatment in Parkinson's disease". *Neurosci Biobehav Rev* 30 (1): 1-23]. Levodopa preparations contribute to the development of motor complications in PD. These comprise abnormal involuntary movements or dyskinesias, such as athetosis and dystonia, along with response fluctuations in which people experience "wearing off" of the drug's effects and/or unpredictable switching between the "on" and the "off" state. Levodopa may also cause nausea, vomiting, gastrointestinal bleeding, dyskinesia at peak dose, and end-of-dose deterioration of function.

Thus, there is a need to develop better treatments to address those problems.

BACKGROUND OF THE INVENTION

One aspect of the invention relates to HPPs of levodopa and/or dopamine.

Another aspect of the invention relates to pharmaceutical compositions comprising one or more HPPs disclosed herein. In certain embodiments, the pharmaceutical composition comprises one or more high penetration prodrugs of NSAID and one or more high penetration prodrugs of dopamine and/or levodopa.

where the parent drug(s) of the HPPs may be the same or different, and may be levodopa, dopamine, aspirin, ibuprofen, and/or other NSAIDs as disclosed herein.

Another aspect of the invention relates to a method of using a composition of the invention in penetrating one or more biological barriers in a biological subject.

Another aspect of the invention relates to a method of using a composition of the invention, or a pharmaceutical composition thereof in treating a condition in a biological subject.

Another aspect of the invention relates to a method of using one or more HPPs or a pharmaceutical composition thereof in treating Parkinson's disease and/or related conditions in a biological subject or subject by administrating the one or more HPPs or a pharmaceutical composition thereof to the biological subject or subject.

DETAILED DESCRIPTION OF THE INVENTION

I. High Penetration Prodrugs of Levodopa

Figure 1:
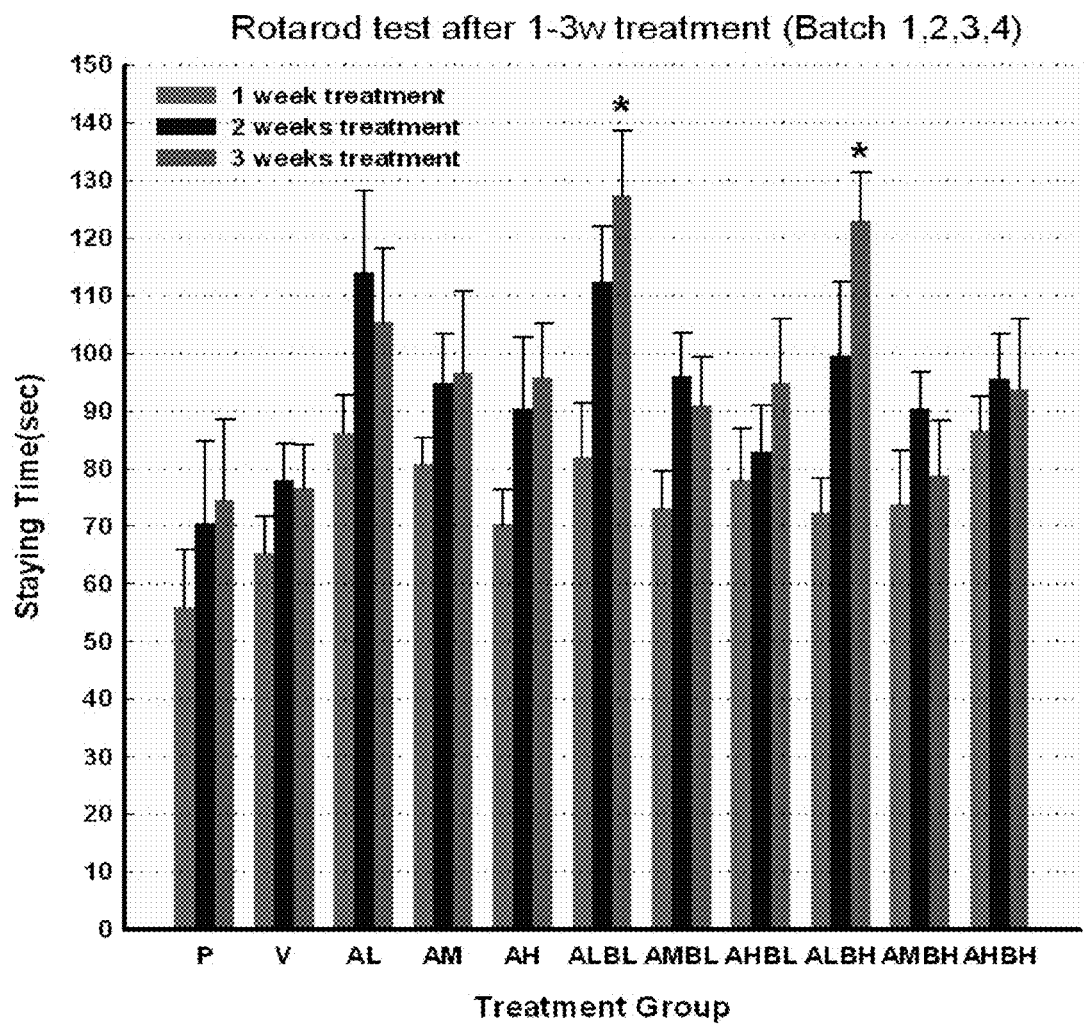
FIG. 1. The staying time results in Totarod test after 1-3 week treatment (n=12) (Example 31).

One aspect of the invention relates to a high penetration prodrug of levodopa having a structure selected from the group consisting of Structure Pro-L-Dopa-1, Structure Pro-L-Dopa-2, Structure Pro-L-Dopa-3, Structure Pro-L-Dopa-4 and Structure Pro-L-Dopa-5:

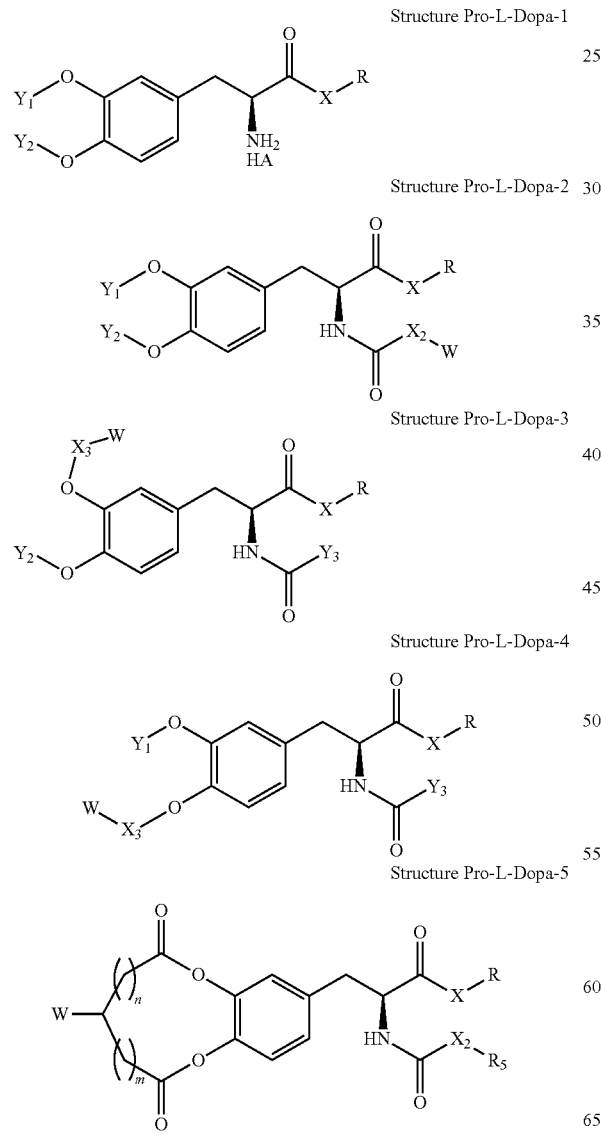

including stereoisomers and pharmaceutically acceptable salts thereof, wherein:

W is selected from the group consisting of H, substituted and unsubstituted alkyl, substituted and unsubstituted cycloalkyl, substituted and unsubstituted heterocycloalkyl, substituted and unsubstituted alkyloxy, substituted and unsubstituted alkenyl, substituted and unsubstituted alkynyl, substituted and unsubstituted aryl, substituted and unsubstituted heteroaryl, the protonatable amine group, pharmaceutically acceptable substituted and unsubstituted amine groups, Structure W-1, Structure W-2, Structure W-3, Structure W-4, Structure W-5, Structure W-6, Structure W-7, Structure W-8, Structure W-9, Structure W-10, Structure W-11, and Structure W-12:

Structure W-1

Structure W-2

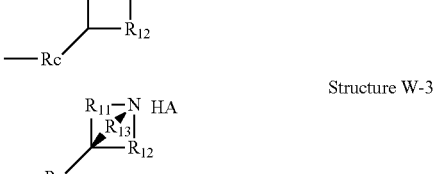

Structure W-3

Structure W-4

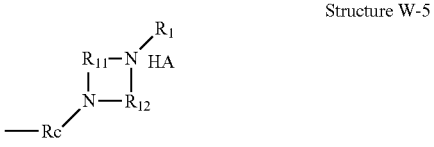

Structure W-5

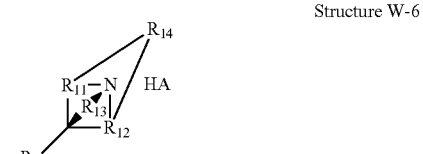

Structure W-6

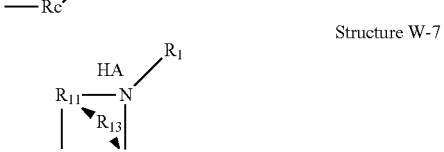

Structure W-7

Structure W-8

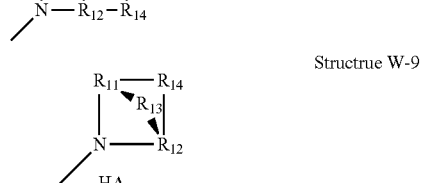

Structrue W-9

-continued

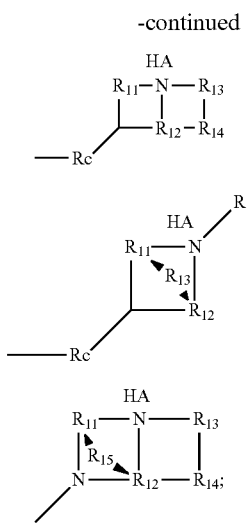

Structure W-10

Structure W-11

Structure W-12

HA is selected from the group consisting of nothing, and pharmaceutically acceptable acid, e.g. hydrochloride hydrobromide, hydroiodide, nitric acid, sulfic acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid and pamoic acid;

$R_1$ and $R_2$ are independently selected from the group consisting of H, substituted and unsubstituted alkyl, substituted and unsubstituted cycloalkyl, substituted and unsubstituted heterocycloalkyl, substituted and unsubstituted alkyloxyl, substituted and unsubstituted alkenyl, substituted and unsubstituted alkynyl, substituted and unsubstituted aryl and substituted and unsubstituted heteroaryl residues;

$R_{11}$-$R_{15}$ are independently selected from the group consisting of nothing, H, $CH_2C(=O)OR_{11}$, substituted and unsubstituted alkyl, substituted and unsubstituted cycloalkyl, substituted and unsubstituted heterocycloalkyl, substituted and unsubstituted alkoxyl, substituted and unsubstituted perfluoroalkyl, substituted and unsubstituted alkyl halide, substituted and unsubstituted alkenyl, substituted and unsubstituted alkynyl, substituted and unsubstituted aryl, and substituted and unsubstituted heteroaryl;

X is selected from the group consisting of O, S, and $NR_3$;

$X_2$ is selected from the group consisting of nothing, O, S, $NR_3$, $CHR_3$—O, $CHR_3$—S, $CHR_3$—O, O—$CHR_3$—O, O—$CHR_3$—S, S—$CHR_3$—O, and S—$CHR_3$—S;

$X_3$ is selected from the group consisting of nothing, C=O, C=S, C(=O)—O, O, S, $NR_3$, C(=O)—O—$CHR_3$—O, C(=O)—O—$CHR_3$—S, C(=O)—S—$CHR_3$—O, and C(=O)—S—$CHR_3$—S:

$Y_1$ is selected from the group consisting of $R_3C(=O)$, $R_3O$—C(=O), and $R_3S$—C(=O);

$Y_2$ is selected from the group consisting of $R_3C(=O)$, $R_3O$—C(=O), and $R_3S$—C(=O);

$Y_3$ is selected from the group consisting of $R_3$, $OR_3$, $SR_3$, $NR_3R_4$, O—$CHR_3$—$OR_4$, O—$CHR_3$—$SR_4$, and S—$CHR_3$—$OR_4$;

n and m is selected from the group consisting of 0, 1, 2, 3, 4, 5, 6, 7, and 8.

$R_c$ is selected from the group consisting of nothing, $CH_2C(=O)OR_6$, substituted and unsubstituted alkyl, substituted and unsubstituted cycloalkyl, substituted and unsubstituted heterocycloalkyl, substituted and unsubstituted alkoxyl, substituted and unsubstituted perfluoroalkyl, substituted and unsubstituted alkyl halide, substituted and unsubstituted alkenyl, substituted and unsubstituted alkynyl, substituted and unsubstituted aryl, and substituted and unsubstituted heteroaryl, wherein any $CH_2$ in R may be further replaced with O, S, P, or $NR_6$;

R is selected from the group consisting of nothing, $CH_2C(=O)OR_6$, substituted and unsubstituted alkyl, substituted and unsubstituted cycloalkyl, substituted and unsubstituted heterocycloalkyl, substituted and unsubstituted alkoxyl, substituted and unsubstituted perfluoroalkyl, substituted and unsubstituted alkyl halide, substituted and unsubstituted alkenyl, substituted and unsubstituted alkynyl, substituted and unsubstituted aryl, and substituted and unsubstituted heteroaryl, wherein any $CH_2$ in R may be further replaced with O, S, P, or $NR_6$;

$R_3$ and $R_4$ are independently selected from the group consisting of nothing, $CH_2C(=O)OR_6$, substituted and unsubstituted alkyl, substituted and unsubstituted cycloalkyl, substituted and unsubstituted heterocycloalkyl, substituted and unsubstituted alkoxyl, substituted and unsubstituted perfluoroalkyl, substituted and unsubstituted alkyl halide, substituted and unsubstituted alkenyl, substituted and unsubstituted alkynyl, substituted and unsubstituted aryl, and substituted and unsubstituted heteroaryl, wherein any $CH_2$ in R may be further replaced with O, S, P, or $NR_6$;

Each $R_6$ is independently selected from the group consisting of H, F, Cl, Br, I, $Na^+$, $K^+$, C(=O)$R_5$, 2-oxo-1-imidazolidinyl, phenyl, 5-indanyl, 2,3-dihydro-1H-inden-5-yl, 4-hydroxy-1,5-naphthyridin-3-yl, substituted and unsubstituted alkyl, substituted and unsubstituted cycloalkyl, substituted and unsubstituted heterocycloalkyl, substituted and unsubstituted alkenyl, substituted and unsubstituted alkynyl, substituted and unsubstituted alkyloxyl, substituted and unsubstituted cycloalkyloxyl, substituted and unsubstituted aryl, substituted and unsubstituted heteroaryl, —C(=O)—W, -$L_1$-$L_4$-$L_2$-W, and W;

each $R_5$ is independently selected from the group consisting of H, C(=O)$NH_2$, $CH_2CH_2OR_6$, $CH_2CH_2N(CH_3)_2$, $CH_2CH_2N(CH_2CH_3)_2$, Cl, F, Br, I, substituted and unsubstituted alkyl, substituted and unsubstituted cycloalkyl, substituted and unsubstituted heterocycloalkyl, substituted and unsubstituted alkyloxyl, substituted and unsubstituted cycloalkyloxyl, substituted and unsubstituted aryl, substituted and unsubstituted heteroaryl, substituted and unsubstituted alkylcarbonyl, substituted and unsubstituted alkylamino, —C(=O)—W, $L_1$-$L_4$-$L_2$-W, and W;

$L_1$ is selected from the group consisting of nothing, O, S, —O-$L_3$-, —S-$L_3$-, —N($L_3$)-, —N($L_3$)-$CH_2$—O, —N($L_3$)-$CH_2$—N($L_5$)-, —O—$CH_2$—O—, —O—CH($L_3$)-O, and —S—CH($L_3$)-O—;

$L_2$ is selected from the group consisting of nothing, O, S, —O-$L_3$-, —S-$L_3$-, —N($L_3$)-, —N($L_3$)-$CH_2$—O, —N($L_3$)-$CH_2$—N($L_5$)-, —O—$CH_2$—O—, —O—CH($L_3$)-O, —S—CH($L_3$)-O—, —O-$L_3$-, —N-$L_3$-, —S-$L_3$-, —N($L_3$)-$L_5$- and $L_3$;

$L_4$ is selected from the group consisting of nothing, C=O, C=S,

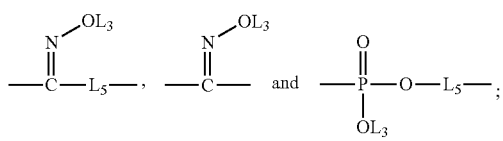

for each $L_1$, $L_2$, and $L_4$, each $L_3$ and $L_5$ is independently selected from the group consisting of nothing, H, $CH_2C(=O)OL_6$, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, P, or $NL_3$;

each $L_6$ is independently selected from the group consisting of H, OH, Cl, F, Br, I, substituted and unsubstituted alkyl, substituted and unsubstituted cycloalkyl, and substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, N, $P(O)OL_6$, $CH=CH$, $C\equiv C$, $CHL_6$, $CL_6L_7$, aryl, heteroaryl, or cyclic groups;

each $L_7$ is independently selected from the group consisting of H, OH, Cl, F, Br, I, substituted and unsubstituted alkyl, substituted and unsubstituted cycloalkyl, and substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, N, $P(O)OL_6$, $CH=CH$, $C\equiv C$, $CHL_6$, $CL_6L_7$, aryl, heteroaryl, or cyclic groups; and any $CH_2$ groups may be replaced with O, S, or NH.

II. High Penetration Prodrugs of Dopamine

Another aspect of the invention relates to a high penetration pro-drug of dopamine comprises a structure selected from the group consisting of Structure Pro-dopamine-1, Structure Pro-dopamine-2, Structure Pro-dopamine-3, and Structure Pro-dopamine-4, and Structure Pro-dopamine-5:

Structure Pro-dopamine-1
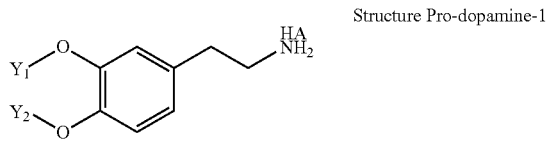

Structure Pro-dopamine-2
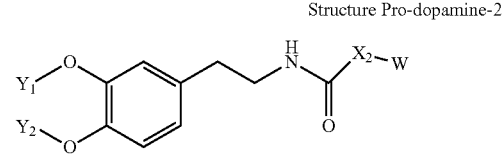

Structure Pro-dopamine-3
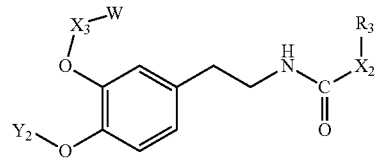

Structure Pro-dopamine-4
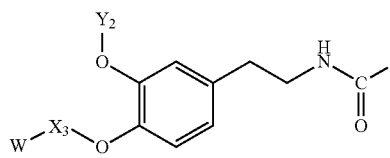

Structure Pro-dopamine-5
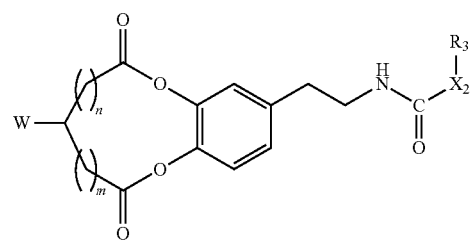

including stereoisomers and pharmaceutically acceptable salts thereof, wherein W, HA, X, $X_2$, $X_3$, $Y_1$, $Y_2$, $Y_3$, n, m, $R_c$, R, $R_1$, $R_2$, $R_3$, $R_4$, $R_5$, $R_6$, $R_{11}$-$R_{15}$, $L_1$, $L_2$, and $L_4$ are defined the same as supra.

III. Pharmaceutical Compositions Comprising a High Penetration Prodrug of NSAID and One or More High Penetration Prodrug of Dopamine and/or Levodopa Another aspect of the invention relates to a pharmaceutical composition comprising one or more high penetration prodrugs of NSAID and one or more high penetration prodrugs of dopamine and/or levodopa.

A high penetration pro-drug of NSAID comprises a structure selected from the group consisting of Structure NSAID-1, Structure NSAID-2, Structure NSAID-3, Structure NSAID-4, Structure NSAID-5, Structure NSAID-6, Structure NSAID-7, Structure NSAID-8, Structure NSAID-9, Structure NSAID-10, Structure NSAID-11, Structure NSAID-12, and Structure NSAID-13:

Structure NSAID-1
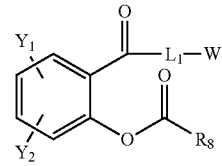

Structure NSAID-2
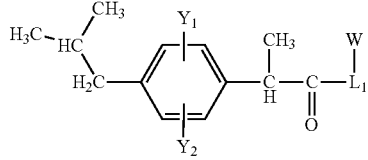

Structure NSAID-3
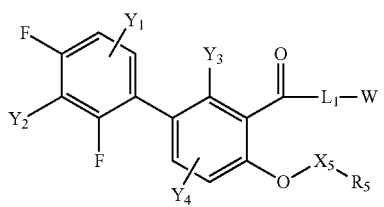

Structure NSAID-4
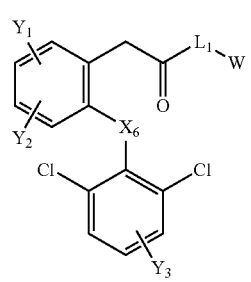

Structure NSAID-5
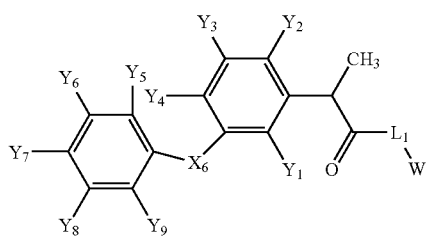

Structure NSAID-6
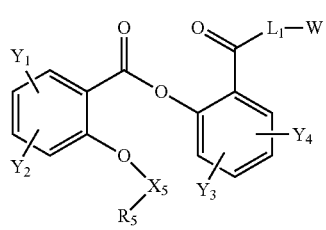

Structure NSAID-7
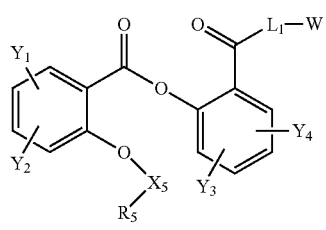

Structure NSAID-8
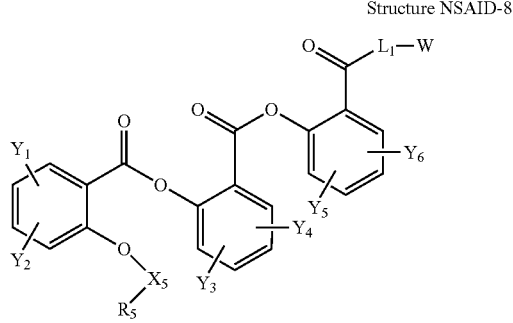

Structure NSAID-9
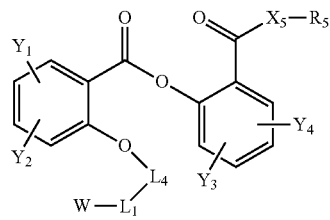

Structure NSAID-10
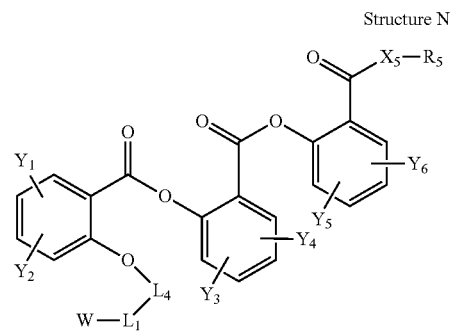

Structure NSAID-11
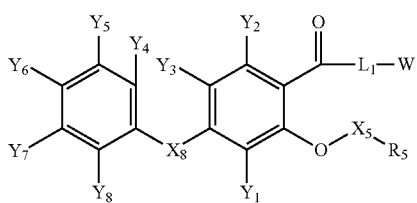

Structure NSAID-12
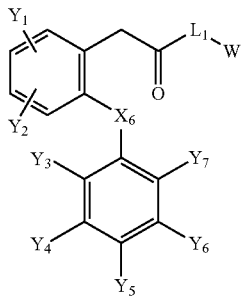

Structure NSAID-13
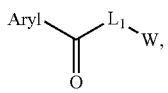

including stereoisomers and pharmaceutically acceptable salts thereof, wherein:

Aryl- is selected from the group consisting of Aryl-1, Aryl-2, Aryl-3, Aryl-4, Aryl-5, Aryl-6, Aryl-7, Aryl-8, Aryl-9, Aryl-10, Aryl-11, Aryl-12, Aryl-13, Aryl-14, Aryl-15, Aryl-16, Aryl-17, Aryl-18, Aryl-19, Aryl-20, Aryl-21, Aryl-22, Aryl-23, Aryl-24, Aryl-25, Aryl-26, Aryl-27, Aryl-28, Aryl-29, Aryl-30, Aryl-31, Aryl-32, Aryl-33, Aryl-34, Aryl-35, Aryl-36, Aryl-37, Aryl-38, Aryl-39, Aryl-40, Aryl-41, Aryl-42, Aryl-43, Aryl-44, Aryl-45, Aryl-46, Aryl-47, Aryl-48, Aryl-49, Aryl-50, Aryl-51, Aryl-52, Aryl-53, Aryl-54, Aryl-55, Aryl-56, Aryl-57, Aryl-58, Aryl-59, Aryl-60, Aryl-61, Aryl-62, Aryl-63, Aryl-64, Aryl-65, Aryl-66, Aryl-67, Aryl-68, Aryl-69, Aryl-70, and Aryl-71:

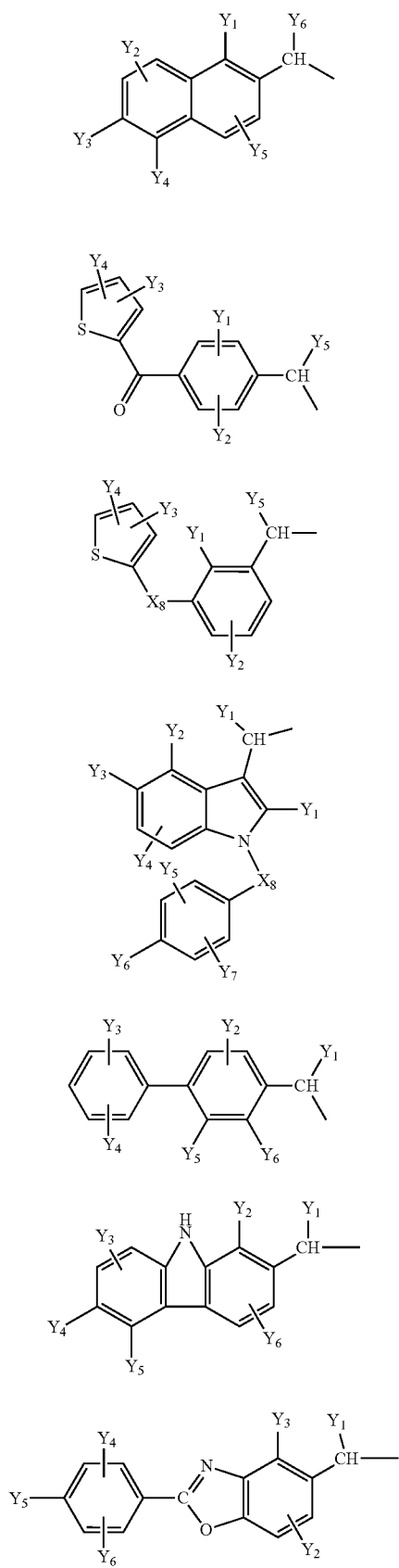
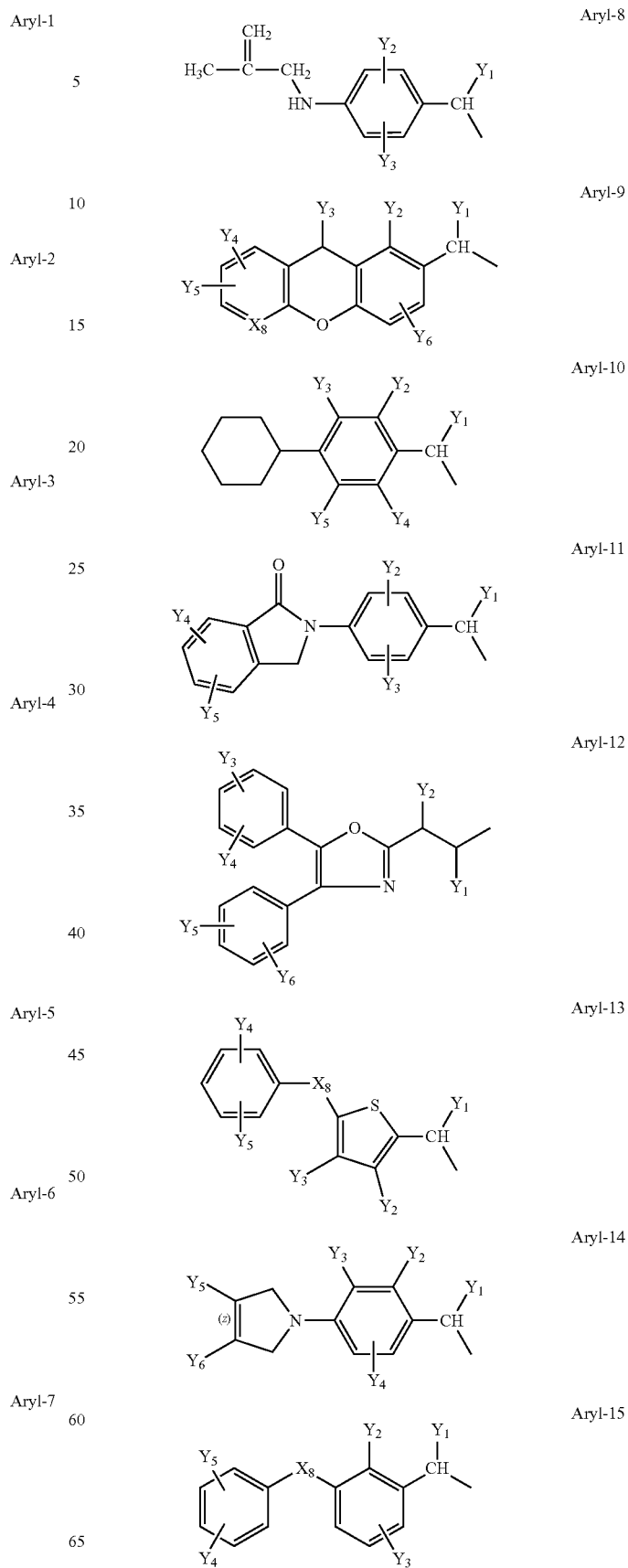

Aryl-16
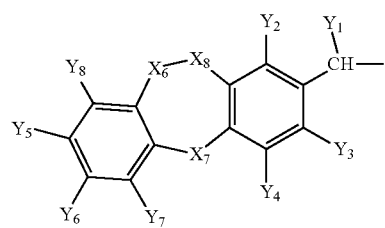
Aryl-17
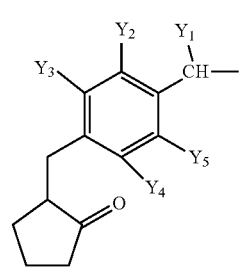
Aryl-18
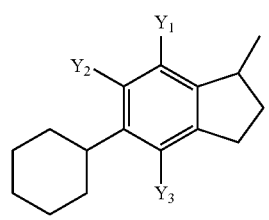
Aryl-19
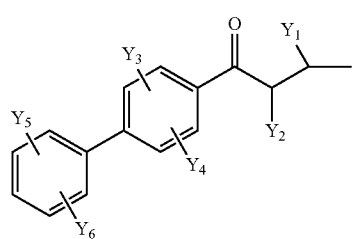
Aryl-20
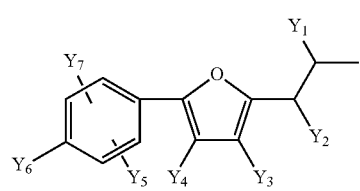
Aryl-21
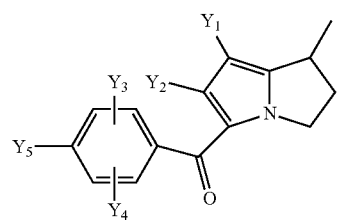
Aryl-22
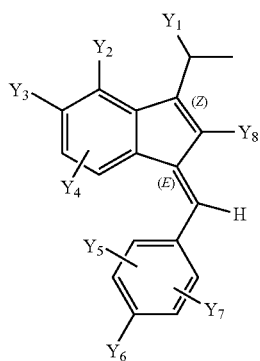
Aryl-23
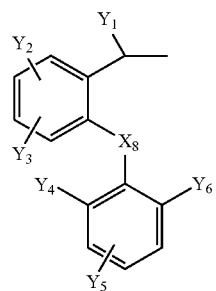
Aryl-24
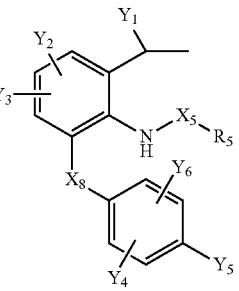
Aryl-25
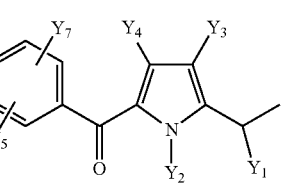
Aryl-26
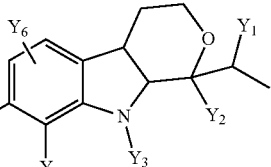
Aryl-27
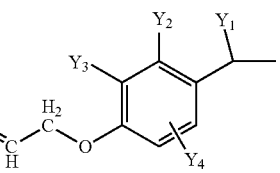

-continued

Aryl-28

Aryl-29

Aryl-30

Aryl-31

Aryl-32

Aryl-33

-continued

Aryl-34

Aryl-35

Aryl-36

Aryl-37

Aryl-38

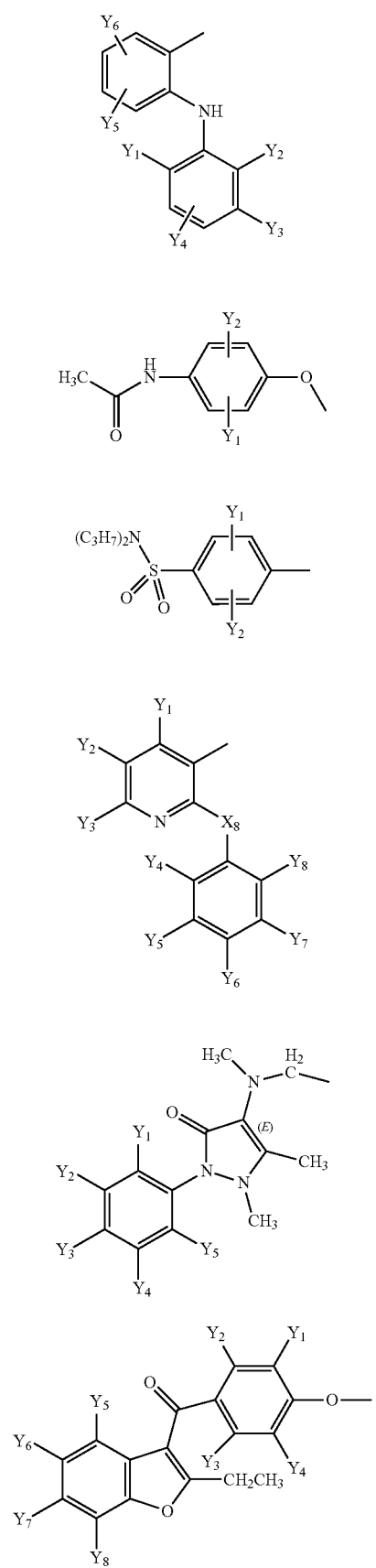

-continued
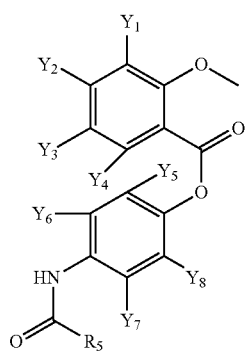
Aryl-50
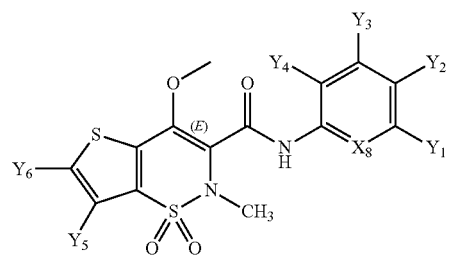
Aryl-51
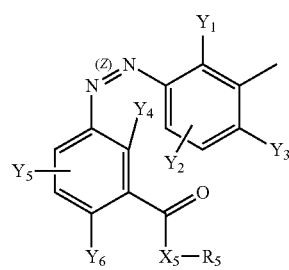
Aryl-52
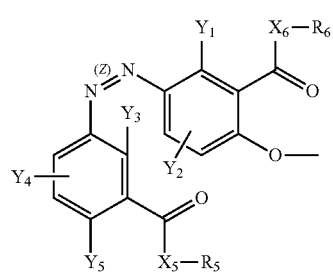
Aryl-53
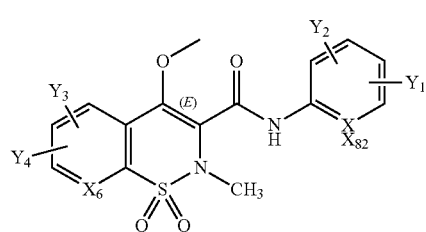
Aryl-54
-continued
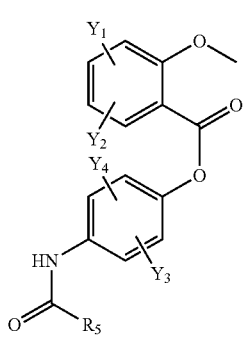
Aryl-55
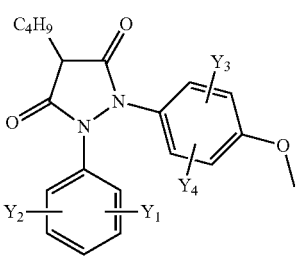
Aryl-56
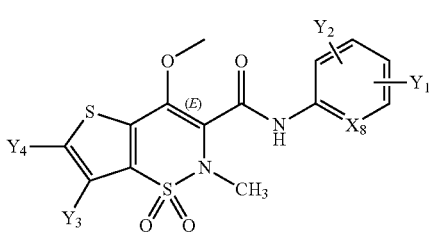
Aryl-57
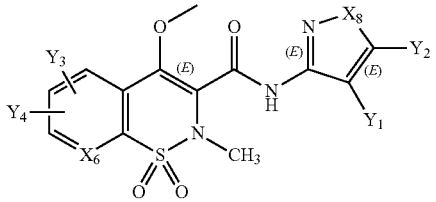
Aryl-58
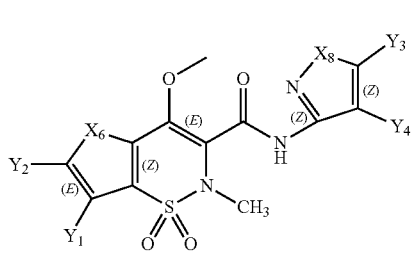
Aryl-59
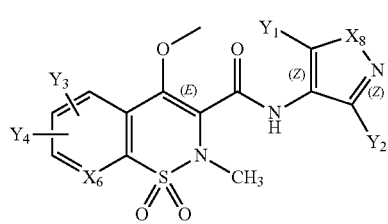
Aryl-60

Aryl-61
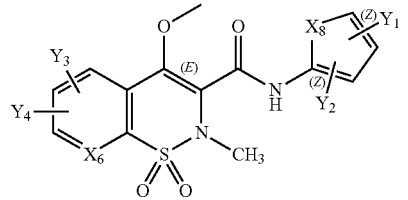

Aryl-62
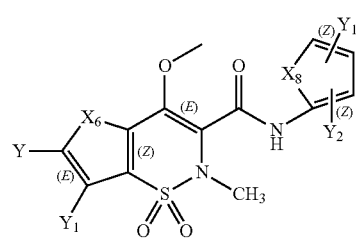

Aryl-63
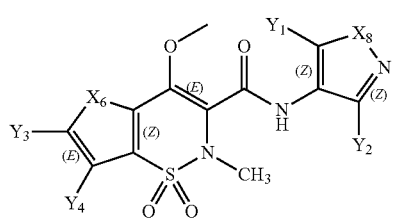

Aryl-64
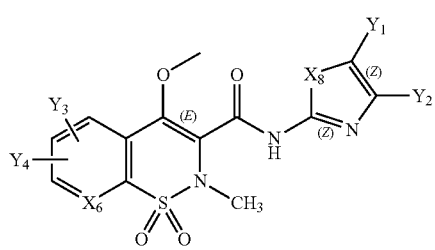

Aryl-65
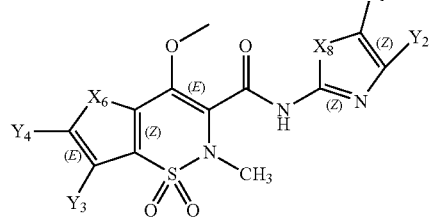

Aryl-66
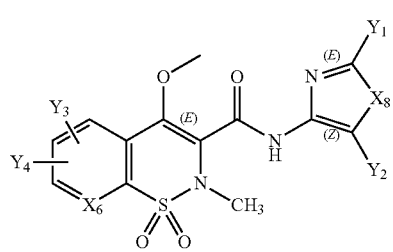

Aryl-67
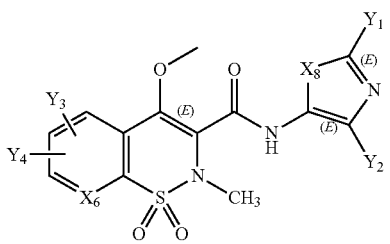

Aryl-68
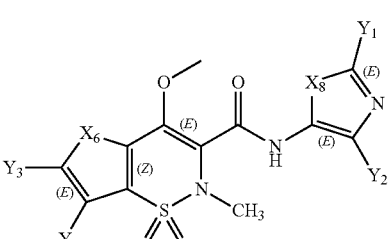

Aryl-69
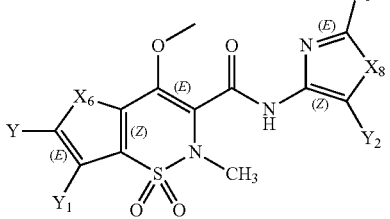

Aryl-70
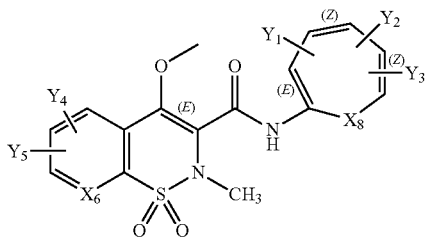

Aryl-71
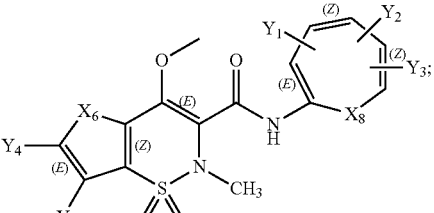

W, HA, X, $X_2$, $X_3$, $Y_1$, $Y_2$, $Y_3$, n, m, $R_c$, R, $R_1$, $R_2$, $R_3$, $R_4$, $R_5$, $R_6$, $R_{11}$-$R_{15}$, $L_1$, $L_2$, and $L_4$, are defined the same as supra;

$X_6$ and $X_8$ are independently selected from the group consisting of nothing, C(=O), C(=S), OC(=O), OC(=S), $CH_2$, CH, S, O and $NR_5$;

$Y_4$, $Y_5$, $Y_6$, $Y_7$, $Y_8$, and $Y_9$ are independently selected from the group consisting of H, OH, OW, OC(=O)W, $L_1$-$L_4$-$L_2$-W, OC(=O)$CH_3$, $CH_3$, $C_2H_5$, $C_3H_7$, $C_4H_9$, $R_6$, $SO_3R_6$, $CH_2OR_6$, $CH_2OC(=O)R_6$, $CH_2C(=O)OR_8$, $OCH_3$, $OC_2H_5$, $OR_6$, $CH_3SO_2$, $R_6SO_2$, $CH_3SO_3$, $R_6SO_3$, $NO_2$, ON, $CF_3$, $OCF_3$, $CH_2(CH_2)_nNR_5R_6$, $CH_2(CH_2)_nOR_6$, CH(C(=O)$NH_2$)$NHR_6$, $CH_2C(=O)NH_2$, F, Br, I, Cl, CH=CHC(=O)NHCH$_2$C(=O)OW, CH=CHC(=O)NHCH$_2$$L_1$-$L_4$-$L_2$-W, $NR_8C(=O)R_5$, $SO_2NR_5R_8$, C(=O)

$R_5$, $SR_5$, $R_6OOCCH(NHR_7)(CH_2)_nC(=O)NH—$, $R_6OOCCH(NHR_7)(CH_2)_nSC(=O)NH—$, $CF_3SCH_2C(=O)NH—$, $CF_3CH_2C(=O)NH—$, $CHF_2SCH_2C(=O)NH—$, $CH_2FSCH_2C(=O)NH—$, $NH_2C(=O)CHFS—CH_2C(=O)NH—$, $R_7NHCH(C(=O)OW)CH_2SCH_2C(=O)NH—$, $R_7NHCH(L_1-L_4-L_2-W)CH_2SCH_2C(=O)NH—$, $CNCH_2SCH_2C(=O)NH—$, $CH_3(CH_2)_nC(=O)NH—$, $R_7N=CHNR_7CH_2CH_2S—$, $R_7N=C(NHR_7)NHC(=O)—$, $R_7N=C(NHR_7)NHC(=O)CH_2$, $CH_3C(Cl)=CHCH_2SCH_2C(=O)NH—$, $(CH_3)_2C(OR_6)—$, $CNCH_2C(=O)NH—$, $CNCH_2CH_2S—$, $R_7HN=CH(NR_7)CH_2CH_2S—$, $CH_2=CHCH_2SCH_2C(=O)NH—$, $CH_3CH(OH)—$, $CH_3CH(OR_8)—$, $CH_3CH(Y_1)—$, $(CH_3)_2CH—$, $CH_3CH_2—$, $CH_3(CH_2)_nCH=CH(CH_2)_mC(=O)NH—$, substituted and unsubstituted perfluoroalkyl, substituted and unsubstituted alkoxyl, substituted and unsubstituted alkylthio, substituted and unsubstituted alkylamino, substituted and unsubstituted perfluoroalkyl, substituted and unsubstituted alkyl halide and substituted and unsubstituted alkylcarbonyl;

each $R_7$ is independently selected from the group consisting of H, F, Cl, Br, I, $CH_3NHC(=O)CH_2CH(NHR_8)C(=O)$, $R_5N=C(NHR_6)NHC(=O)—$, $C(=O)CH_3$, $C(=O)R_6$, $PO(OR_5)OR_6$, substituted and unsubstituted alkyl, substituted and unsubstituted cycloalkyl, substituted and unsubstituted heterocycloalkyl, substituted and unsubstituted alkyloxyl, substituted and unsubstituted alkenyl, substituted and unsubstituted alkynyl, substituted and unsubstituted aryl, substituted and unsubstituted heteroaryl, substituted and unsubstituted alkylcarbonyl, substituted and unsubstituted alkylamino, $L_1-L_4-L_2-W$, and $C—(=O)—W$; and each $R_8$ is independently selected from the group consisting of H, F, Cl, Br, I, $CH_3$, $C_2H_5$, $CF_3$, $CH_2CH_2F$, $CH_2CH_2Cl$, $CH_2CH_2Br$, $CH_2CH_2I$, $CH_2CHF_2$, $CH_2CF_3$, $CH_2F$, $CH_2Cl$, $CH_2Br$, $CH_2I$, $CH_2NR_6R_7$, $CH(NHR_7)CH_2C(=O)NH_2$, $C_3H_7$, $C_4H_9$, $C_5H_{11}$, $R_6$, $C(=O)R_6$, $C(=O)NH_2$, $CH_2C(=O)NH_2$, $CH_2OC(=O)NH_2$, $PO(OR_5)OR_6$, $C(CH_3)_2C(=O)OR_6$, $CH(CH_3)C(=O)OR_6$, $CH_2C(=O)OR_6$, $C(=O)—W$, $L_1-L_4-L_2-W$, W, substituted and unsubstituted perfluoroalkyl, substituted and unsubstituted alkyl, substituted and unsubstituted cycloalkyl, substituted and unsubstituted heterocycloalkyl, substituted and unsubstituted alkoxyl, substituted and unsubstituted alkylamino, substituted and unsubstituted perfluoroalkyl, substituted and unsubstituted alkyl halide and substituted and unsubstituted alkylcarbonyl.

As used herein, the term "pharmaceutically acceptable salt" means those salts of compounds of the invention that are safe for application in a subject. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,11-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 J. PHARM. SCI. 1-19 (1977), incorporated herein by reference.

As used herein, unless specified otherwise, the term "alkyl" means a branched or unbranched, saturated or unsaturated, monovalent or multivalent hydrocarbon group, including saturated alkyl groups, alkenyl groups and alkynyl groups. Examples of alkyl include, but are not limited to, methyl, ethyl, propyl, isopropyl, butyl, isobutyl, t-butyl, pentyl, hexyl, heptyl, octyl, nonyl, decyl, undecyl, dodecyl, ethenyl, propenyl, butenyl, isobutenyl, pentenyl, hexenyl, heptenyl, octenyl, nonenyl, decenyl, undecenyl, dodecenyl, ethynyl, propynyl, butynyl, isobutynyl, pentynyl, hexynyl, heptynyl, octynyl, nonynyl, decynyl, undecynyl, dodecynyl, methylene, ethylene, propylene, isopropylene, butylene, isobutylene, t-butylene, pentylene, hexylene, heptylene, octylene, nonylene, decylene, undecylene and dodecylene. In certain embodiments, the hydrocarbon group contains 1 to 30 carbons. In certain embodiments, the hydrocarbon group contains 1 to 20 carbons. In certain embodiments, the hydrocarbon group contains 1 to 12 carbons.

As used herein, unless specified otherwise, the term "cycloalkyl" means an alkyl which contains at least one ring and no aromatic rings. Examples of cycloalkyl include, but are not limited to, cyclopropyl, cyclobutyl, cyclopentyl, cyclohexyl, cycloheptyl, cyclooctyl, cyclononyl, cyclodecyl, cycloundecyl and cyclododecyl. In certain embodiments, the hydrocarbon chain contains 1 to 30 carbons. In certain embodiments, the hydrocarbon group contains 1 to 20 carbons. In certain embodiments, the hydrocarbon group contains 1 to 12 carbons.

As used herein, unless specified otherwise, the term "heterocycloalkyl" means a cycloalkyl wherein at least one ring atom is a non-carbon atom. Examples of the non-carbon ring atom include, but are not limited to, S, O and N.

As used herein, unless specified otherwise, the term "alkoxyl" means an alkyl, cycloalkyl or heterocycloalkyl, which contains one or more oxygen atoms. Examples of alkoxyl include, but are not limited to, $—CH_2—OH$, $—OCH_3$, $—O—R_e$, $—R_e—OH$, $—R_{e1}—O—R_{e2}—$, wherein $R_e$, $R_{e1}$ and $R_{e2}$ can be the same or different alkyl, cycloalkyl or heterocycloalkyl.

As used herein, unless specified otherwise, the term "alkyl halide" means an alkyl, cycloalkyl or heterocycloalkyl, which contains one or more halogen atoms, wherein the halogen atoms can be the same or different. The term "halogen" means fluorine, chlorine, bromine or iodine. Examples of alkyl halide include, but are not limited to, $—R_e—F$, $—R_e—Cl$, $—R_e—Br$, $—R_e—I$, $—R_e(F)—$, $—R_e(Cl)—$, $—R_e(Br)—$ and $—R_e(I)—$, wherein $R_e$ is an alkyl, cycloalkyl or heterocycloalkyl.

As used herein, unless specified otherwise, the term "alkylthio" means an alkyl, cycloalkyl or heterocycloalkyl, which contains one or more sulfur atoms. Examples of alkylthio include, but are not limited to, $—CH_2—SH$, $—SCH_3$, $—S—R_e$, $—R_e—SH$, $—R_{e1}—S—R_{e2}—$, wherein $R_e$, $R_{e1}$ and $R_{e2}$ are the same or different alkyl, cycloalkyl or heterocycloalkyl.

As used herein, unless specified otherwise, the term "alkylamino" means an alkyl, cycloalkyl or heterocycloalkyl, which contains one or more nitrogen atoms. Examples of alkylamino include, but are not limited to, $—CH_2—NH$, $—NCH_3$, $—N(R_{e1})—R_{e2}$, $—N—R_e$, $—R_e—NH_2$, $—R_{e1}—N—R_{e2}$ and $—R_e—N(R_{e1})—R_{e2}$ wherein $R_e$, $R_{e1}$ and $R_{e2}$ are the same or different alkyl, cycloalkyl or heterocycloalkyl.

As used herein, unless specified otherwise, the term "alkylcarbonyl" means an alkyl, cycloalkyl or heterocycloalkyl, which contains one or more carbonyl groups. Examples of alkylcarbonyl group include, but are not limited to, aldehyde group (—$R_e$—C(O)—H), ketone group (—$R_e$—C(O)—$R_{e1}$), carboxylic acid group ($R_e$—C(=O)OH), ester group (—$R_e$—C(=O)O—$R_{e1}$), carboxamide, (—$R_e$—C(=O)O—N($R_{e1}$)$R_{e2}$), enone group (—$R_e$—C(O)—C($R_{e1}$)=C($R_{e2}$)$R_{e3}$), acyl halide group (—$R_e$—C(O)—$X_h$) and acid anhydride group (—$R_e$—C(O)—O—C(O)—$R_{e1}$), wherein $R_e$, $R_{e1}$, $R_{e2}$ and $R_{e3}$ are the same or different alkyl, cycloalkyl, or heterocycloalkyl; and $X_h$ is a halogen.

As used herein, unless specified otherwise, the term "perfluoroalkyl" means an alkyl, cycloalkyl or heterocycloalkyl, which contains one or more fluoro group, including, without limitation, perfluoromethyl, perfluoroethyl, perfluoropropyl.

As used herein, unless specified otherwise, the term "aryl" means a chemical structure comprising one or more aromatic rings. In certain embodiments, the ring atoms are all carbon. In certain embodiments, one or more ring atoms are non-carbon, e.g. oxygen, nitrogen, or sulfur ("heteroaryl"). Examples of aryl include, without limitation, phenyl, benzyl, naphthalenyl, anthracenyl, pyridyl, quinoyl, isoquinoyl, pyrazinyl, quinoxalinyl, acridinyl, pyrimidinyl, quinazolinyl, pyridazinyl, cinnolinyl, imidazolyl, benzimidazolyl, purinyl, indolyl, furanyl, benzofuranyl, isobenzofuranyl, pyrrolyl, indolyl, isoindolyl, thiophenyl, benzothiophenyl, pyrazolyl, indazolyl, oxazolyl, benzoxazolyl, isoxazolyl, benzisoxazolyl, thiaxolyl, quanidino and benzothiazolyl.

In certain embodiments, the pharmaceutical composition comprises at least one HPP of a parent drug that can be used to treat Parkinson's disease or a related compound thereof, and a pharmaceutically acceptable carrier.

In certain embodiments, a pharmaceutical composition may comprise more than one HPPs of the same or different parent drugs. The different parent drugs can belong to the same or different categories of drugs that are used to treat Parkinson's disease. For example, a pharmaceutical composition may comprise HPPs of parent drugs or related compounds thereof, wherein the parent drugs are selected from the group consisting of Levodopa, dopamine, aspirin and other nonsteroidal anti-inflammatory drugs (NSAIDs), and any combinations thereof.

A pharmaceutical composition may further comprise water.

A pharmaceutical composition may further comprise an alcohols (e.g., ethanol, glycerol, isopropanol, octanol, etc.).

In certain embodiments, a pharmaceutical composition comprises HPPs of parent drugs or related compounds thereof, wherein at least one of the parent drugs is levodopa (e.g. HPPs comprising one or more structures of structure Pro-L-dopa-1, Pro-L-dopa-2, Pro-L-dopa-3, Pro-L-dopa-4, and/or Pro-L-dopa-5); dopamine (e.g. HPPs comprising one or more structures of structure Pro-dopamine-1, Pro-dopamine-2, Pro-dopamine-3, Pro-dopamine-4, and/or Structure Pro-dopamine-5); and at least one of the parent drug is aspirin or other anti-inflammatory drugs (e.g. HPPs comprising one or more structures selected from the group consisting of Structure NSAID-1, Structure NSAID-2, Structure NSAID-3, Structure NSAID-4, Structure NSAID-5, Structure NSAID-6, Structure NSAID-7, NSAID-8, Structure NSAID-9, Structure NSAID-10, Structure NSAID-11, Structure NSAID-12, and Structure NSAID-13.)

In certain embodiments, a pharmaceutical composition comprises 4-(2-(2-(methylamino)acetamido)ethyl)-1,2,-phenylene dibenzoate hydrochloride, 4-(2-(2-(methylamino)acetamido)ethyl)-1,2,-phenylene dibenzoate acetic acid, 4-(6-methyl-4,8-dioxo-5,7-dioxa-2,9-diazadecan-11-yl)-1,2,-phenylene dibenzoate hydrobromide, 4-(2-(2-amino-3-phenylpropanamido)ethyl)-1,2,-phenylene dibenzoate hydrochloride, 4-(2-(((1-((pyrrolidine-2-carbonyl)oxy)ethoxy)amino)ethyl)-1,2,-phenylene dibenzoate hydrochloride, 4-(2-piperidine-4-carboxamido)ethyl)-1,2,-phenylene bis(2-ethylbutanoate) hydrochloride, 4-(2-(((-octahydro-1H-quinolizin-3-yl)oxy)carbonyl)amino)ethyl)-1,2,-phenylene bis(2-ethylbutanoate)acetate, 1-(((2-(4-amino-2,5-dioxo-2,3,4,5-tetrahydrobenzo[b][1,4]dioxocin-8-yl)ethyl)carbamoyl)oxy)ethyl isobutyrate hydrofluoride, 1-(((2-(3-amino-2,5-dioxo-2,3,4,5-tetrahydrobenzo[b][1,4]dioxocin-8-yl)ethyl)carbamoyl)oxy)ethyl isobutyrate hydrofluoride, (-(2-((ethoxycarbonyl)amino)ethyl)-2-(2-methylamino)acetoxy)phenyl benzoate hydrochloride, 5-(2-((ethoxycarbonyl)amino)ethyl)-2-(2-methylamino)acetoxy)phenyl benzoate hydrochloride, 4-(2-aminoethyl)-1,2-phenylene dibenzoate hydrochloride, (S)-4-(2-amino-3-isopropoxy-3-oxopropyl)-1,2-phenylene dibenzoate hydrochloride, (S)-4-(2-amino-3-(heptan-4-yloxy)-3-oxopropyl)-1,2-phenylene dibenzoate hydrochloride, (S)-4-(2-amino-3-isopropoxy-3-oxopropyl)-1,2-phenylene dipentanoate hydrochloride, (S)-4-(2-amino-3-ethoxy-3-oxopropyl)-1,2-phenylene diacetate hydrochloride, (S)-4-(2-amino-3-oxo-3-(pentan-3-yloxy)propyl)-1,2-phenylene bis(2-methylpropanoate) hydrobromide, (S)-4-(2-aminoacetamido)-3-isopropoxy-3-oxopropyl)-1,2-phenylene dibenzoate hydrochloride, 4-((2S)-3-oxo-3-(pentan-3-yloxy)-2-(pyrrolidine-2-carboxamido)propyl)-1,2-phenylene dibenzoate hydrofluoride, (S)-4-(3-isopropoxy-3-oxo-2-(piperidine-4-carboxamido)propyl)-1,2-phenylene dibenzoate hydrochloride, 4-((2S)-3-isopropoxy-3-2-(octahydro-1H-quinolizine-2-carboxamido)-3-oxopropyl)-1,2-phenylene bis(2-methylpropanoate) hydrochloride, (2S)-isopropyl 3-(3-amino-2,5-dioxo-2,3,4,5-tetrahydrobenzo[b][1,4]dioxocin-8-yl)-2-(((1-(isobutyryloxy)ethoxy)carbonyl)amino)propanoate hydrobromide, (2S)-isopropyl 3-(4-amino-2,5-dioxo-2,3,4,5-tetrahydrobenzo[b][1,4]dioxocin-8-yl)-2-(((1-(isobutyryloxy)ethoxy)carbonyl)amino)propanoate hydrobromide, 5-((2S)-2-(((1-(isobutyryloxy)ethoxy)carbonyl)amino-3-isopropoxy-3-oxopropyl)-2-(2-(methylamino)acetoxy)phenyl benzoate hydrochloride, 4-((2S)-2-(((1-(isobutyryloxy)ethoxy)carbonyl)amino-3-isopropoxy-3-oxopropyl)-2-(2-(methylamino)acetoxy)phenyl benzoate hydrochloride, 4-((2S)-3-isopropoxy-2-((((octahydroindolizin-1-yl)oxy)carbonyl)amino)-3-oxopropyl)-1,2-phenylene dibenzoate acetate, 2-(diethylamino)ethyl 2-[(2,6-dichloro-3-methylphenyl)amino]benzoate.acetate, (Z)-2-(diethylaminoethyl)ethyl 2-(5-fluoro-2-methyl-1-(4-methylsulfinyl)benzylidene)-1H-inden-1-yl)acetate.AcOH, 2-(dimethylamino)ethyl 2-(3-phenoxyphenyl) propionate-.hydrochloride, S-(2-(dimethylamino)ethyl 2-(3-phenoxyphenyl) propanethioate hydrochloride, 2-(dipropylamino)ethyl 4-acetoxy-2',4'-difluoro-[1,1'-biphenyl]-3-carboxylate hydrochloride, 2-(diethylamino)ethyl 2-(4-isobutylphenyl) propionate hydrochloride, and/or 2-(diethylamino)ethyl 2-acetoxybenzoate.

In certain embodiments, the pharmaceutical composition further comprises one or more catechol-O-methyl transferase inhibitors. In certain embodiments, the one or more catechol-O-methyl transferase inhibitors are applied orally.

Catechol-O-methyl transferase (COMT) metabolizes L-Dopa into 3-methoxy-4-hydroxy-L-phenylalanine (3-OMD) in the periphery, which does not easily cross the blood brain barrier (BBB). Entacapone and tolcapone are Catechol-O-methyl transferase inhibitors and prevents COMT from metabolizing L-DOPA into 3-methoxy-4-hydroxy-L-phenylalanine in the periphery to avoid the undesirable effects of L-DOPA.

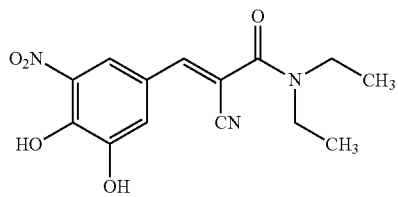

Entacapone [(2E)-2-cyano-3-(3,4-dihydroxy-5-nitrophenyl)-N,N-diethylprop-2-enamide]

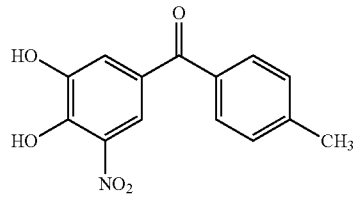

Tolcapone [(3,4-dihydroxy-5-nitrophenyl)(4-methylphenyl)methanone]

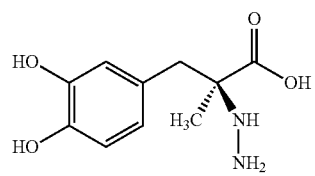

(2S)-3-(3,4-dihydroxyphenyl)-2-hydrazino-2-methylpropanoic acid (Carbidopa)

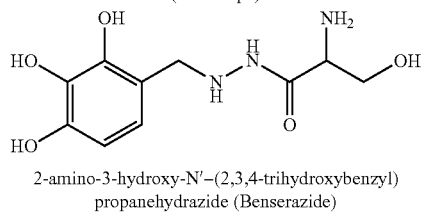

2-amino-3-hydroxy-N'-(2,3,4-trihydroxybenzyl) propanehydrazide (Benserazide)

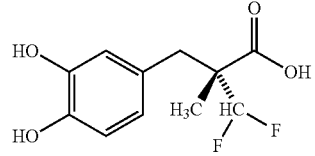

(2S)-2-Amino-2-[3,4-dihydroxyphenyl)methyl]-3,3-difluoropropanoic acid (alpha-difluoromethyl-DAPA)

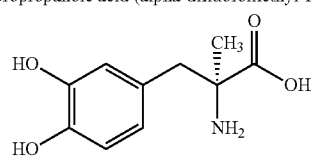

(S)-2-amino-3-(3,4-dihydroxyphenyl)-2-methyl-propanoic acid (methyldopa)

BERGE ET AL., 66 J. PHARM. SCI. 1-19 (1977).

For example, a pharmaceutical composition may comprise HPPs of parent drugs or related compounds thereof, wherein the parent drugs are selected from the group consisting of Levodopa, dopamine, aspirin and other nonsteroidal anti-inflammatory drugs (NSAIDs), and any combinations thereof plus an orally administrated catechol-O-methyl transferase inhibitor (e.g. entacapone, and tolcapone).

In certain embodiments, the pharmaceutical composition further comprises one or more aromatic-L-amino-acid decarboxylase (DOPA Decarboxylase or DDC) inhibitors. In certain embodiments, the one or more aromatic-L-amino-acid decarboxylase inhibitors are applied orally. Aromatic-L-amino-acid decarboxylase (DOPA Decarboxylase or DDC) an enzyme important in the biosynthesis of L-DOPA to Dopamine (DA). DDC exists both outside of (body periphery) and within the confines of the blood-brain barrier. The DDC inhibitors prevent DDC conversion of levodopa to dopamine. However, exogenously provided levadopa gets metabolized peripherally to its active metabolite dopamine before reaching the blood-brain barrier. Therefore, the PD brain, which is deficient in dopamine, will not receive as much of its prodrug precursor levodopa due to peripheral DDC breakdown. However, carbidopa and other DDC inhibitors as a peripheral DDC inhibitor can decrease peripheral DDC conversion of levodopa before it crosses the blood-brain barrier. In other words, carbidopa and other DDC inhibitors have no effect on brain DDC conversion of levodopa to dopamine. Ultimately, a greater proportion of the exogenously provided levodopa reaches the brain.

Examples of DDC inhibitors include, without limitation, carbidopa, benserazide, difluromethyldopa, and α-methyldopa.

In certain embodiments, a pharmaceutical composition may comprise more than one HPPs of different parent drugs. The different parent drugs can belong to the same or different categories of drugs that are used to treat Parkinson's disease. For example, a pharmaceutical composition may comprise HPPs of parent drugs or related compounds thereof, wherein the parent drugs are selected from the group consisting of Levodopa, dopamine, aspirin and other non-steroidal anti-inflammatory drugs (NSAIDs), and any combinations thereof plus one or more DDC inhibitors selected from the group consisting of carbidopa, benserazide, difluromethyldopa, α-methyldopa, and any other aromatic-L-amino-acid decarboxylase inhibitor.

In certain embodiments, a pharmaceutical composition comprises (S)-4-(2-amino-3-isopropoxy-3-oxopropyl)-1,2-phenylene dibenzoate and 2-(diethylamino)ethyl 2-acetoxybenzoate.

In certain embodiments, a pharmaceutical composition comprises (S)-4-(2-amino-3-isopropoxy-3-oxopropyl)-1,2-phenylene dibenzoate, 2-(diethylamino)ethyl 2-acetoxybenzoate, carbidopa and/or entacapone.

In certain embodiments, a pharmaceutical composition comprises (S)-4-(2-amino-3-oxo-3-(pentan-3-yloxy)propyl)-1,2-phenylene bis(2-methylpropanoate) and 2-(diethylamino)ethyl 2-(4-isobutylphenyl)propionate.

In certain embodiments, a pharmaceutical composition comprises 4-(2-(((1-((pyrrolidine-2-carbonyl)oxy)ethoxy)amino)ethyl)-1,2,-phenylene dibenzoate and 4-(dimethylamino)butyl 2-(3-phenoxyphenyl) propionate.

In certain embodiments, a pharmaceutical composition comprises (S)-4-(2-amino-3-oxo-3-(pentan-3-yloxy)propyl)-1,2-phenylene bis(2-methylpropanoate), 2-(diethylamino)ethyl 2-(4-isobutylphenyl)propionate, carbidopa and/or entacapone.

In certain embodiments, a pharmaceutical composition comprises (S)-4-(2-amino-3-(heptan-4-yloxy)-3-oxopropyl)-1,2-phenylene dibenzoate, and 2-(dipropylamino)ethyl 4-acetoxy-2',4'-difluoro-[1,1'-biphenyl]-3-carboxylate.

In certain embodiments, a pharmaceutical composition comprises (S)-4-(2-amino-3-(heptan-4-yloxy)-3-oxopropyl)-1,2-phenylene dibenzoate, and 2-(dipropylamino)ethyl 4-acetoxy-2',4'-difluoro-[1,1'-biphenyl]-3-carboxylate, carbidopa and/or entacapone.

In certain embodiments, a pharmaceutical composition comprises a therapeutically effective amount of one or more HPPs disclosed herein. As used herein, a "therapeutically effective amount," "therapeutically effective concentration" or "therapeutically effective dose" is an amount which, as compared to a corresponding subject who has not received such amount, results in improved treatment, healing, prevention, or amelioration of a disease, disorder, or side effect, or a decrease in the rate of advancement of a disease or disorder.

This amount will vary depending upon a variety of factors, including but not limited to the characteristics of the HPPs disclosed herein or pharmaceutical compositions thereof (including activity, pharmacokinetics, pharmacodynamics, and bioavailability thereof), the physiological condition of the subject treated (including age, sex, disease type and stage, general physical condition, responsiveness to a given dosage, and type of medication) or cells, the nature of the pharmaceutically acceptable carrier or carriers in the formulation, and the route of administration. Further, an effective or therapeutically effective amount may vary depending on whether the one or more HPPs disclosed herein or the pharmaceutical composition thereof is administered alone or in combination with other drug(s), other therapy/therapies or other therapeutic method(s) or modality/modalities. One skilled in the clinical and pharmacological arts will be able to determine an effective amount or therapeutically effective amount through routine experimentation, namely by monitoring a cell's or subject's response to administration of the one or more HPPs disclosed herein or the pharmaceutical composition thereof and adjusting the dosage accordingly. A typical dosage may range from about 0.1 mg/kg to about 100 mg/kg or more, depending on the factors mentioned above. In other embodiments, the dosage may range from about 0.1 mg/kg to about 100 mg/kg; or about 1 mg/kg to about 100 mg/kg; or about 5 mg/kg up to about 100 mg/kg. For additional guidance, see Remington: The Science and Practice of Pharmacy, 21st Edition, Univ. of Sciences in Philadelphia (USIP), Lippincott Williams & Wilkins, Philadelphia, Pa., 2005, which is hereby incorporated by reference as if fully set forth herein for additional guidance for determining a therapeutically effective amount.

As used herein, the term "about" refers to ±10%, ±5%, or ±1%, of the value following "about."

The term "pharmaceutically acceptable carrier" as used herein means a pharmaceutically-acceptable material, composition or vehicle, such as a liquid or solid filler, diluent, excipient, solvent or encapsulating material, involved in carrying or transporting an HPP from one location, body fluid, tissue, organ (interior or exterior), or portion of the body, to another location, body fluid, tissue, organ, or portion of the body.

Each carrier is "pharmaceutically acceptable" in the sense of being compatible with the other ingredients, e.g., an HPP, of the formulation and suitable for use in contact with the tissue or organ of a biological subject without excessive toxicity, irritation, allergic response, immunogenicity, or other problems or complications, commensurate with a reasonable benefit/risk ratio.

In certain embodiments, the pharmaceutically acceptable carrier is selected from the group consisting of alcohol, acetone, ester, cellulose, mannitol, croscarmellose sodium, vegetable oil, hydroxypropyl methylcellulose, water, and aqueous solution.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; and (21) other non-toxic compatible substances employed in pharmaceutical formulations such as acetone.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

In one embodiment, the pharmaceutically acceptable carrier is an aqueous carrier, e.g. buffered saline and the like. In certain embodiments, the pharmaceutically acceptable carrier is a polar solvent, e.g. acetone and alcohol.

The concentration of HPP in these formulations can vary widely, and will be selected primarily based on fluid volumes, viscosities, body weight and the like in accordance with the particular mode of administration selected and the biological subject's needs. For example, the concentration can be 0.0001% to 100%, 0.001% to 50%, 0.01% to 30%, 0.1% to 20%, 1% to 10% wt.

The compositions of the invention can be administered for prophylactic, therapeutic, and/or hygienic use. Such administration can be topical, mucosal, e.g., oral, nasal, vaginal, rectal, parenteral, transdermal, subcutaneous, intramuscular, intravenous, via inhalation, ophthalmic and other convenient routes. The pharmaceutical compositions can be administered in a variety of unit dosage forms depending upon the method of administration. For example, unit dosage forms suitable for oral administration include powder, tablets, pills, capsules and lozenges and for transdermal administration include solution, suspension and gel.

Thus, a typical pharmaceutical composition for transdermal, oral, and intravenous administrations would be about $10^{-8}$ g to about 100 g, about $10^{-8}$ g to about $10^{-5}$ g, about $10^{-6}$ g to about 1 g, about $10^{-6}$ g to about 100 g, about 0.001 g to about 100 g, about 0.01 g to about 10 g, or about 0.1 g to about 1 g per subject per day. Dosages from about 0.001 mg, up to about 100 g, per subject per day may be used. Actual methods for preparing parenterally administrable compositions will be known or apparent to those skilled in the art and are described in more detail in such publications as Remington: The Science and Practice of Pharmacy 21st ed., Lippincott Williams & Wilkins, (2005).

IV. Applications of HPPs i) Methods for Penetrating a Biological Barrier.

Another aspect of the invention relates to a method of using a composition of the invention in penetrating one or more biological barriers in a biological subject. The method comprises a step of administering to a biological subject an HPP or a pharmaceutical composition thereof. In certain embodiments, an HPP exhibits more than about 20 times or higher, 50 times or higher, >about 100 times or higher, >about 200 time higher, >about 300 times or higher, >about 500 times or higher, >about 1,000 times or higher penetration rate through one or more biological barriers than its parent drug.

The term "biological barrier" as used herein refers to a biological layer that separates an environment into different spatial areas or compartments, which separation is capable of modulating (e.g. restricting, limiting, enhancing or taking no action in) the passing through, penetrating or translocation of substance or matter from one compartment/area to another. The different spatial areas or compartments as referred to herein may have the same or different chemical or biological environment(s). The biological layer as referred herein includes, but is not limited to, a biological membrane, a cell layer, a biological structure, an inner surface of subjects, organisms, organs or body cavities, an external surface of subjects, organisms, organs or body cavities, or any combination or plurality thereof.

Examples of a biological membrane include a lipid bilayer structure, eukaryotic cell membrane, prokaryotic cell membrane, and intracellular membrane (e.g., nucleus or organelle membrane, such as membrane or envelope of Golgi apparatus, rough and smooth endoplasmic reticulum (ER), ribosomes, vacuoles, vesicles, liposomes, mitochondria, lysosome, nucleus, chloroplasts, plastids, peroxisomes or microbodies).

The lipid bilayer referred to herein is a double layer of lipid-class molecules, including, but not limited to, phospholipids and cholesterol. In a particular embodiment, lipids for bilayer are amphiphilic molecules consisting of polar head groups and non-polar fatty acid tails. The bilayer is composed of two layers of lipids arranged so that their hydrocarbon tails face one another to form an oily core held together by the hydrophobic effect, while their charged heads face the aqueous solutions on either side of the membrane. In another particular embodiment, the lipid bilayer may contain one or more embedded protein and/or sugar molecule(s).

Examples of a cell layer include a lining of eukaryotic cells (e.g., epithelium, lamina propria and smooth muscle or muscularis mucosa (in gastrointestinal tract)), a lining of prokaryotic cells (e.g., surface layer or S-layer which refers to a two dimensional structure monomolecular layer composed of identical proteins or glycoproteins, specifically, an S-layer refers to a part of a cell envelope commonly found in bacteria and archaea), a biofilm (a structured community of microorganisms encapsulated within a self-developed polymeric matrix and adherent to a living or inert surface), and a plant cell layer (e.g., epidermis). The cells may be normal cells or pathological cells (e.g. disease cells, cancer cells).

Examples of biological structures include structures sealed by tight or occluding junctions that provide a barrier to the entry of toxins, bacteria and viruses, e.g. the blood milk barrier and the blood brain barrier (BBB). In particular, BBB is composed of an impermeable class of endothelium, which presents both a physical barrier through tight junctions adjoining neighboring endothelial cells and a transport barrier comprised of efflux transporters. The biological structure may also include a mixture of cells, proteins and sugars (e.g. blood clots).

Examples of the inner surface of subjects, organisms, organs or body cavities include buccal mucosa, esophageal mucosa, gastric mucosa, intestinal mucosa, olfactory mucosa, oral mucosa, bronchial mucosa, uterine mucosa and endometrium (the mucosa of the uterus, inner layer of the wall of a pollen grain or the inner wall layer of a spore), or a combination or plurality thereof.

Examples of the external surface of subjects, organisms, organs or body cavities include capillaries (e.g. capillaries in the heart tissue), mucous membranes that are continuous with skin (e.g. such as at the nostrils, the lips, the ears, the genital area, and the anus), outer surface of an organ (e.g. liver, lung, stomach, brain, kidney, heart, ear, eye, nose, mouth, tongue, colon, pancreas, gallbladder, duodenum, rectum stomach, colonrectum, intestine, vein, respiratory system, vascular, anorectum and pruritus ani), skin, cuticle (e.g. dead layers of epidermal cells or keratinocytes or superficial layer of overlapping cells covering the hair shaft of an animal, a multi-layered structure outside the epidermis of many invertebrates, plant cuticles or polymers cutin and/or cutan), external layer of the wall of a pollen grain or the external wall layer of a spore), and a combination or plurality thereof.

In addition, a biological barrier further includes a sugar layer, a protein layer or any other biological layer, or a combination or plurality thereof. For example, skin is a biological barrier that has a plurality of biological layers. A skin comprises an epidermis layer (outer surface), a demis layer and a subcutaneous layer. The epidermis layer contains several layers including a basal cell layer, a spinous cell layer, a granular cell layer, and a stratum corneum. The cells in the epidermis are called keratinocytes. The stratum corneum ("horny layer") is the outmost layer of the epidermis, wherein cells here are flat and scale-like ("squamous") in shape. These cells contain a lot of keratin and are arranged in overlapping layers that impart a tough and oilproof and waterproof character to the skin's surface.

ii) Methods for Treating Parkinson's Disease in a Biological Subject

Another aspect of the invention relates to a method of using a composition of the invention, or a pharmaceutical composition thereof in treating a condition in a biological subject. The method comprises administrating the pharmaceutical composition to the biological subject.

The term "treating" as used herein means curing, alleviating, inhibiting, or preventing. The term "treat" as used herein means cure, alleviate, inhibit, or prevent. The term "treatment" as used herein means cure, alleviation, inhibition or prevention.

The term "biological subject," or "subject" as used herein means an organ, a group of organs that work together to perform a certain task, an organism, or a group of organisms. The term "organism" as used herein means an assembly of molecules that function as a more or less stable whole and has the properties of life, such as animal, plant, fungus, or micro-organism.

The term "animal" as used herein means a eukaryotic organism characterized by voluntary movement. Examples of animals include, without limitation, vertebrata (e.g. human, mammals, birds, reptiles, amphibians, fishes, marsipobranchiata and leptocardia), tunicata (e.g. thaliacea, appendicularia, sorberacea and ascidioidea), articulata (e.g. insecta, myriapoda, malacapoda, arachnida, pycnogonida, merostomata, crustacea and annelida), gehyrea (anarthropoda), and helminthes (e.g. rotifera).

The conditions the method can treat include conditions that can be treated by the parent drug of the HPP are Parkinson's disease and related conditions.

iii). Methods of Using One or More HPPs or a Pharmaceutical Compositions Thereof in Treatments of Parkinson's Disease and Related Conditions.

Another aspect of the invention relates to a method of using one or more HPPs or a pharmaceutical composition thereof in treating Parkinson's disease and/or related conditions in a biological subject or subject by administrating the one or more HPPs or a pharmaceutical composition thereof to the biological subject or subject.

In certain embodiments, a method of treating a Parkinson's disease and related conditions in a subject comprises administering a therapeutic effective amount of an HPP, or a pharmaceutical composition thereof to the subject.

An HPP or a pharmaceutical composition thereof can be administered to a biological subject by any administration route known in the art, including without limitation, oral, enteral, buccal, nasal, topical, rectal, vaginal, aerosol, transmucosal, epidermal, transdermal, dermal, ophthalmic, pulmonary, subcutaneous, and/or parenteral administration. The pharmaceutical compositions can be administered in a variety of unit dosage forms depending upon the method of administration.

The preferred administered methods are transdermal, dermal, topical administration for a compound.

In certain embodiments, the method further comprises orally administering to the subject a therapeutically effective amount of one or more COMT inhibitors and/or one or more DDC inhibitors described supra.

When a plurality of drugs (e.g. HPPs, COMT inhibitors and DDC inhibitors) are applied to a subject, the plurality of HPPs and/or other drugs can be applied at substantially the same time or at different times. The plurality of drugs may be mixed together before the administration to the subject, or administered to the subject separately. In certain embodiments, some of the plurality of drugs are mixed before administration, while others are applied separately. Each drug may be applied in any possible order, and any possible manner.

As used herein, a pharmaceutical composition may comprise multiple components that are applied to the subject in different administration route. For example, a pharmaceutical composition comprising one or more HPPs and one or more COMT inhibitors and/or one or more DDC inhibitors described supra, the one or more HPPs may be applied transdermally, topically, or dermally, while the one or more COMT inhibitors and/or one or more DDC inhibitors described supra may be applied orally. The multiple components may be applied in any order and any combination possible.

An HPP or a pharmaceutical composition thereof can be given to a subject in the form of formulations or preparations suitable for each administration route. The formulations useful in the methods of the invention include one or more HPPs, one or more pharmaceutically acceptable carriers therefor, and optionally other therapeutic ingredients. The formulations may conveniently be presented in unit dosage form and may be prepared by any methods well known in the art of pharmacy. The amount of active ingredient which can be combined with a carrier material to produce a single dosage form will vary depending upon the subject being treated and the particular mode of administration. The amount of an HPP which can be combined with a carrier material to produce a pharmaceutically effective dose will generally be that amount of an HPP which produces a therapeutic effect. Generally, out of one hundred percent, this amount will range from about 1 percent to about ninety-nine percent of the HPP, preferably from about 1 percent to about 20 percent.

Methods of preparing these formulations or compositions include the step of bringing into association an HPP with one or more pharmaceutically acceptable carriers and, optionally, one or more accessory ingredients. In general, the formulations are prepared by uniformly and intimately bringing into association an HPP with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an HPP as an active ingredient. A compound may also be administered as a bolus, electuary, or paste.

In solid dosage forms for oral administration (e. g., capsules, tablets, pills, dragees, powders, granules and the like), the HPP is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate, (5) solution retarding agents, such as paraffin, (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered HPPs or peptidomimetic moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of an HPP therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain pacifying agents and may be of a composition that they release the HPP(s) only, or preferentially, in a certain portion of the gastrointestinal tract, optionally, in a delayed manner. Examples of embedding compositions which can be used include polymeric substances and waxes. The HPP can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the HPP, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the HPP, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more HPPs with one or more suitable non-irritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent. Formulations which are suitable for vaginal administration also include pessaries, tampons, creams, gels, pastes, foams or spray formulations containing such carriers as are known in the art to be appropriate.

Formulations for the topical or transdermal or epidermal or dermal administration of an HPP composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required. The ointments, pastes, creams and gels may contain, in addition to the HPP composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the HPP composition, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane. The best formulations for the topical or transdermal administration are pure water, solution, aqueous solution, ethanol and water solution, and isopropanol and water solution.

An HPP or a pharmaceutical composition thereof can be alternatively administered by aerosol. This can be accomplished by preparing an aqueous aerosol, liposomal preparation or solid particles containing the HPPs. A nonaqueous (e. g., fluorocarbon propellant) suspension could be used. Sonic nebulizers can also be used. An aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches can also be used to deliver HPP compositions to a target site. Such formulations can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Formulations suitable for parenteral administration comprise an HPP in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the formulations suitable for parenteral administration include water, ethanol, polyols (e. g., such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Formulations suitable for parenteral administration may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Injectable depot forms are made by forming microencapsule matrices of an HPP or in biodegradable polymers such as polylactide-polyglycolide. Depending on the ratio of the HPP to polymer, and the nature of the particular polymer employed, the rate of drug release can be controlled. Examples of other biodegradable polymers include poly (orthoesters) and poly (anhydrides). Depot injectable formulations are also prepared by entrapping the HPP in liposomes or microemulsions which are compatible with body tissue.

In certain embodiments, an HPP or a pharmaceutical composition thereof is delivered to an action site in a therapeutically effective dose. As is known in the art of pharmacology, the precise amount of the pharmaceutically effective dose of an HPP that will yield the most effective results in terms of efficacy of treatment in a given patient will depend upon, for example, the activity, the particular nature, pharmacokinetics, pharmacodynamics, and bioavailability of a particular HPP, physiological condition of the subject (including race, age, sex, weight, diet, disease type and stage, general physical condition, responsiveness to a given dosage and type of medication), the nature of pharmaceutically acceptable carriers in a formulation, the route and frequency of administration being used, and the severity or propensity of the condition that is to be treated. However, the above guidelines can be used as the basis for fine-tuning the treatment, e. g., determining the optimum dose of administration, which will require no more than routine experimentation consisting of monitoring the subject and adjusting the dosage. Remington: The Science and Practice of Pharmacy (Gennaro ed. 20.sup.th edition, Williams & Wilkins PA, USA) (2000).

IV. Advantages

Levodopa may cause nausea, vomiting, gastrointestinal bleeding, dyskinesia at peak dose, and end-of-dose deterioration of function. These problems may be solved by transdermally administration of the high penetration compositions of L-Dopa and dopamine which can deliver a minimal therapeutically effective amount constantly to avoid gastrointestinal bleeding, dyskinesia at peak dose, and end-of-dose deterioration of function.

Recently, increasing evidence from human and animal studies has suggested that neuroinflammation is an important contributor to the neuronal loss in PD. Moreover, the pro-inflammatory agent lipopolysaccharide itself can directly initiate degeneration of dopamine-containing neurons or combine with other environmental factor(s), such as the pesticide rotenone, to exacerbate such neurodegeneration. These effects provide strong support for the involvement of inflammation in the pathogenesis of PD. Although dopamine replacement can alleviate symptoms of the disorder, there is no proven therapy to halt the underlying progressive degeneration of dopamine-containing neurons. The transdermally administration of the high penetration compositions of L-Dopa and/or dopamine with the high penetration compositions of aspirin and/or other NSAID may not only alleviate symptoms of Parkinson's disease, but also halt the underlying progressive degeneration of dopamine containing neurons.

When the high penetration compositions of L-Dopa and/or dopamine, and aspirin and/or other NSAID are administered transdermally, Carbidopa, benserazide, difluromethyldopa, α-methyldopa, and/or other DDC inhibitors and/or and/or entacapone, andtolcapone, and/or other COMT inhibitors are administrated orally can help a greater proportion of the exogenously provided levodopa or dopamine reaches the brain to reduce the L-dopa or dopamine side effects.

V. Examples

The following examples are provided to better illustrate the claimed invention and are not to be interpreted in any way as limiting the scope of the invention. All specific compositions, materials, and methods described below, in whole or in part, fall within the scope of the invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the invention. It is the intention of the inventors that such variations are included within the scope of the invention. Furthermore, all references cited herein are incorporated by reference in their entireties, as if fully set forth herein.

Example 1

Preparation of 4-(2-(2-(methylamino)acetamido)ethyl)-1,2,-phenylene dibenzoate hydrochloride

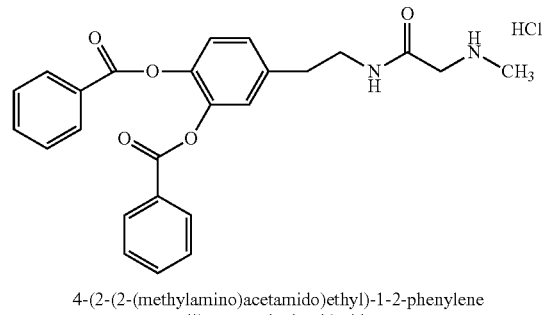

4-(2-(2-(methylamino)acetamido)ethyl)-1-2-phenylene dibenzoate hydrochloride

In this example, a dopamine.HCl solution was prepared by adding dopamine.HCl (19 g) into acetone (200 mL). Water (200 mL) and sodium bicarbonate (R0090, 50 g) were added into the dopamine.HCl solution to provide a 1st mixture. Then Boc-N-methylglycine N-hydroxysuccinimide ester (Boc-Sar-OSu, 29 g) was added to the 1st mixture to provide a 2nd mixture. The 2nd mixture was stirred at RT overnight, and added ethyl acetate (R0061, 500 mL) for extraction. The organic layer was separated, and washed with water (2×100 mL), 20% citric acid (2×200 mL), and water (3×100 mL), respectively, and dried over sodium sulfate to provide a 3rd solution. Then the sodium sulfate was filtered and washed with ethyl acetate to provide a 4th mixture. The 3rd solution and the 4th mixture were combined, and added first with pyridine (R0081, 30 mL), and then with benzoyl chloride (R0488, 30 g) drop by drop to provide a 5th mixture. The 5th mixture was stirred at RT for 2 hours, then washed with water (2×100 mL), 5% sodium bucarbonate (2×100 mL), water (100 mL), 20% citric acid (2×200 mL), and water (3×100 mL), respectively, and dried over sodium sulfate to provide a 6th solution. The sodium sulfate was filtered and washed with ethyl acetate to provide a 7th solution. The 6th solution and the 7th solution were combined and concentrated to about 200 mL (an 8th solution). Into the 8th solution was added anisole (20 g), and then bubbled HCl gas (20 g) to form precipitation. The precipitated solid was collected and washed with ethyl acetate to yield 4-(2-(2-(methylamino)acetamido)ethyl)-1,2-phenylene dibenzoate hydrochloride salt.

Example 2

Preparation of 4-(2-(2-(methylamino)acetamido)ethyl)-1,2,-phenylene dibenzoate acetic acid In this example, 4-(2-(2-(methylamino)acetamido)-1,2,-phenylene dibenzoate hydrochloride (23 g) was dissolved in isopropanol (300 mL) to provide a 1st mixture. Sodium acetate (4 g) was added into the 1st mixture to provide a 2nd mixture. The 2nd mixture was stirred at RT for 2 hours, and filtered to remove solid therein. The filtered solution was evaporated to dryness to yield 4-(2-(2-(methylamino)acetamido)ethyl)-1,2,-phenylene dibenzoate acetic acid salt.

Example 3

Preparation of 4-(6-methyl-4,8-dioxo-5,7-dioxa-2,9-diazadecan-11-yl)-1,2,-phenylene dibenzoate hydrobromide

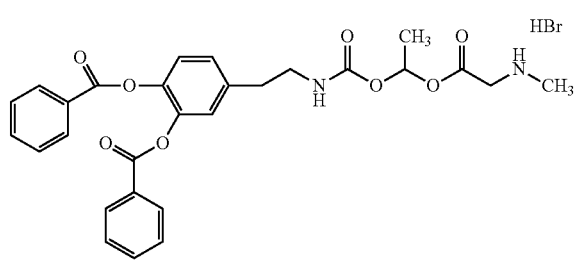

4-(6-methyl-4,8-dioxo-5,7-dioxa-2,9-diazaundecan-11-yl)-1,2-phenylene dibenzoate hydrobromide In this example, a dopamine.HCl solution was prepared by adding dopamine.HCl (19 g) into acetone (200 mL). Water (200 mL) and sodium bicarbonate (R0090, 50 g) were added into the dopamine.HCl solution to provide a 1st mixture. Then di-tert-butyl dicarbonate (22 g) was added to the 1st mixture to provide a 2nd mixture. The 2nd mixture was stirred at RT overnight, and added ethyl acetate (R0061, 500 mL) for extraction. The organic layer was separated, and washed with water (2×100 mL), 20% citric acid (2×200 mL), and water (3×100 mL), respectively, and dried over sodium sulfate to provide a 3rd solution. Then the sodium sulfate was filtered and washed with ethyl acetate to provide a 4th mixture. The 3rd solution and the 4th mixture were combined, and added first with pyridine (R0081, 30 mL), and then with benzoyl chloride (R0488, 30 g) drop by drop to provide a 5th mixture. The 5th mixture was stirred at RT for 2 hours, then washed with water (2×100 mL), 5% sodium bucarbonate (2×100 mL), water (100 mL), 20% citric acid (2×200 mL), and water (3×100 mL), respectively, and dried over sodium sulfate to provide a 6th solution. The sodium sulfate was filtered and washed with ethyl acetate to provide a 7th solution. The 6th solution and the 7th solution were combined and concentrated to about 200 mL (an 8th solution). Into the 8th solution was added anisole (20 g), and then bubbled HCl gas (20 g) to form precipitation. The precipitated solid was collected and washed with ethyl acetate, and then suspended in DCM (200 mL) to provide a 9th mixture. Sodium bicarbonate (20 g) and tetrabutylammonium hydrogen sulfate (11 g) were added into the 9th mixture to provide a 10th mixture. Then 1-chloroethyl chloroformate (16 g) was added into the 10th mixture to provide an 11th mixture. The 11th mixture was stirred at RT overnight. Then the organic layer of the 11th mixture was collected and washed with water (3×200 mL), and dried over anhydrous sodium sulfate to provide a 12th solution. The sodium sulfate was removed by filtration and washed with DCM to provide a 13th solution. The 12th solution and the 13th solution were combined and evaporated to dryness. The residue was dissolved in acetonitrile (200 mL) to provide a 14th mixture. Boc-sarcosine (36 g) was added into the 14th mixture to provide a 15th mixture. A mixture of [diisopropylethylamine (34 mL) and Boc-sarcosine (36 g) was prepared first and then added into the 15th mixture to provide a 16th mixture. The 16th mixture was stirred at 55° C. for 48 hours, and added ethyl acetate (500 mL) with stirring. The obtained organic layer was collected and washed with 5% sodium bicarbonate (3×100 mL) and water (3×100 mL), respectively, and dried over anhydrous sodium sulfate to provide a 17th solution. The sodium sulfate was filtered and washed with ethyl acetate to provide a 18th solution. The 17th solution and the 18th solution were combined and concentrated to 300 mL. Into the concentrated solution was added anisole (20 g) and then bubbled HBr gas (30 g) to provide precipitation. The precipitated solid was collected and washed with ethyl acetate to yield 4-(6-methyl-4,8-dioxo-5,7-dioxa-2,9-diazadecan-11-yl)-1,2,-phenylene dibenzoate hydrobromide.

Example 4

Preparation of 4-(2-(2-amino-3-phenylpropanamido)ethyl)-1,2,-phenylene dibenzoate hydrochloride 4-(2-(2-amino-3-phenylpropanamido)ethyl)-1,2-phenylene dibenzoate hydrochloride In this example, a dopamine.HCl solution was prepared by adding dopamine.HCl (19 g) into acetone (200 mL). Water (200 mL) and sodium bicarbonate (R0090, 50 g) were added into the dopamine.HCl solution to provide a 1st mixture. Then boc-phenylalanine N-hydroxysuccinimide ester (Boc-Phe-OSu, 36 g) was added to the 1st mixture to provide a 2nd mixture. The 2nd mixture was stirred at RT overnight, and added ethyl acetate (R0061, 500 mL) for extraction. The organic layer was separated, and washed with water (2×100 mL), 20% citric acid (2×200 mL), and water (3×100 mL), respectively, and dried over sodium sulfate to provide a 3rd solution. Then the sodium sulfate was filtered and washed with ethyl acetate to provide a 4th mixture. The 3rd solution and the 4th mixture were combined, and added first with pyridine (R0081, 30 mL), and then with benzoyl chloride (R0488, 30 g) drop by drop to provide a 5th mixture. The 5th mixture was stirred at RT for 2 hours, then washed with water (2×100 mL), 5% sodium bucarbonate (2×100 mL), water (100 mL), 20% citric acid (2×200 mL), and water (3×100 mL), respectively, and dried over sodium sulfate to provide a 6th solution. The sodium sulfate was filtered and washed with ethyl acetate to provide a 7th solution. The 6th solution and the 7th solution were combined and concentrated to about 200 mL (an 8th solution). Into the 8th solution was added anisole (20 g), and then bubbled HCl gas (20 g) to form precipitation. The precipitated solid was collected and washed with ethyl acetate to yield 4-(2-(2-amino-3-phenylpropanamido)ethyl)-1,2,-phenylene dibenzoate hydrochloride.

Example 5

Preparation of 4-(2-(((1-((pyrrolidine-2-carbonyl)oxy)ethoxy)amino)ethyl)-1,2,-phenylene dibenzoate hydrochloride

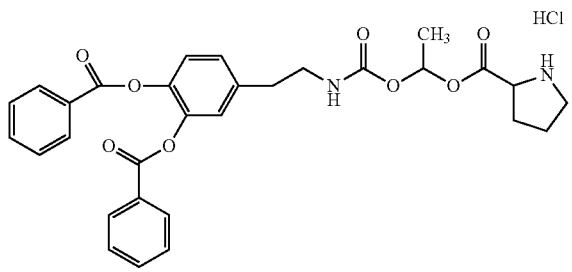

4-(2-(((1-((pyrrolidine-2-carbonyl)oxy)ethoxy)carbonyl)amino)ethyl)-1,2-phenylene dibenzoate hydrochloride In this example, a dopamine.HCl solution was prepared by adding dopamine.HCl (19 g) into acetone (200 mL). Water (200 mL) and sodium bicarbonate (R0090, 50 g) were added into the dopamine.HCl solution to provide a 1st mixture. Then di-tert-butyl dicarbonate (22 g) was added to the 1st mixture to provide a 2nd mixture. The 2nd mixture was stirred at RT overnight, and added ethyl acetate (R0061, 500 mL) for extraction. The organic layer was separated, and washed with water (2×100 mL), 20% citric acid (2×200 mL), and water (3×100 mL), respectively, and dried over sodium sulfate to provide a 3rd solution. Then the sodium sulfate was filtered and washed with ethyl acetate to provide a 4th mixture. The 3rd solution and the 4th mixture were combined, and added first with pyridine (R0081, 30 mL), and then with benzoyl chloride (R0488, 30 g) drop by drop to provide a 5th mixture. The 5th mixture was stirred at RT for 2 hours, then washed with water (2×100 mL), 5% sodium bucarbonate (2×100 mL), water (100 mL), 20% citric acid (2×200 mL), and water (3×100 mL), respectively, and dried over sodium sulfate to provide a 6th solution. The sodium sulfate was filtered and washed with ethyl acetate to provide a 7th solution. The 6th solution and the 7th solution were combined and concentrated to about 200 mL (an 8th solution). Into the 8th solution was added anisole (20 g), and then bubbled HCl gas (20 g) to form precipitation. The precipitated solid was collected and washed with ethyl acetate, and then suspended in DCM (200 mL) to provide a 9th mixture. Sodium bicarbonate (20 g) and tetrabutylammonium hydrogen sulfate (11 g) were added into the 9th mixture to provide a 10th mixture. Then 1-chloroethyl chloroformate (16 g) was added into the 10th mixture to provide an 11th mixture. The 11th mixture was stirred at RT overnight. Then the organic layer of the 11th mixture was collected and washed with water (3×200 mL), and dried over anhydrous sodium sulfate to provide a 12th solution. The sodium sulfate was removed by filtration and washed with DCM to provide a 13th solution. The 12th solution and the 13th solution were combined and evaporated to dryness. The residue was dissolved in acetonitrile (200 mL) to provide a 14th mixture. Boc-sarcosine (36 g) was added into the 14th mixture to provide a 15th mixture. A mixture of [diisopropylethylamine (34 mL) and Boc-sarcosine (36 g) was prepared first and then added into the 15th mixture to provide a 16th mixture. The 16th mixture was stirred at 55° C. for 48 hours, and added ethyl acetate (500 mL) with stirring. The obtained organic layer was collected and washed with 5% sodium bicarbonate (3×100 mL) and water (3×100 mL), respectively, and dried over anhydrous sodium sulfate to provide a 17th solution. The sodium sulfate was filtered and washed with ethyl acetate to provide a 18th solution. The 17th solution and the 18th solution were combined and concentrated to 300 mL. Into the concentrated solution was added anisole (20 g) and then bubbled HCl gas (30 g) to provide precipitation. The precipitated solid was collected and washed with ethyl acetate to yield 4-(2-(((1-((pyrrolidine-2-carbonyl)oxy)ethoxy)amino)ethyl)-1,2,-phenylene dibenzoate hydrochloride.

Example 6

Preparation of 4-(2-piperidine-4-carboxamido)ethyl)-1,2,-phenylene bis(2-ethylbutanoate) hydrochloride

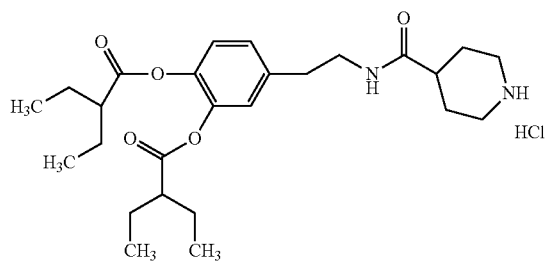

4-(2-(piperidine-4-carboxamido)ethyl)-1,2-phenylene bis(2-ethylbutanoate) hydrochloride In this example, a dopamine.HCl solution was prepared by adding dopamine.HCl (19 g) into acetone (200 mL). Water (200 mL) and sodium bicarbonate (R0090, 50 g) were added into the dopamine.HCl solution to provide a 1st mixture. Then Boc-piperidine-4-carboxylic acid N-hydroxysuccinimide ester (Boc-Inp-OSu, 33 g) was added to the 1st mixture to provide a 2nd mixture. The 2nd mixture was stirred at RT overnight, and added ethyl acetate (R0061, 500 mL) for extraction. The organic layer was separated, and washed with water (2×100 mL), 20% citric acid (2×200 mL), and water (3×100 mL), respectively, and dried over sodium sulfate to provide a 3rd solution. Then the sodium sulfate was filtered and washed with ethyl acetate to provide a 4th mixture. The 3rd solution and the 4th mixture were combined, and added first with pyridine (R0081, 30 mL), and then with 2-ethylbutyryl chloride (28 g) drop by drop to provide a 5th mixture. The 5th mixture was stirred at RT for 2 hours, then washed with water (2×100 mL), 5% sodium bucarbonate (2×100 mL), water (100 mL), 20% citric acid (2×200 mL), and water (3×100 mL), respectively, and dried over sodium sulfate to provide a 6th solution. The sodium sulfate was filtered and washed with ethyl acetate to provide a 7th solution. The 6th solution and the 7th solution were combined and concentrated to about 200 mL (an 8th solution). Into the 8th solution was added anisole (20 g), and then bubbled HCl gas (20 g) to form precipitation. The precipitated solid was collected and washed with ethyl acetate to yield 4-(2-piperidine-4-carboxamido)ethyl)-1,2,-phenylene bis(2-ethylbutanoate) hydrochloride.

Example 7

Preparation of 4-(2-((((-octahydro-1H-quinolizin-3-yl)oxy)carbonyl)amino)ethyl)-1,2,-phenylene bis(2-ethylbutanoate)acetate

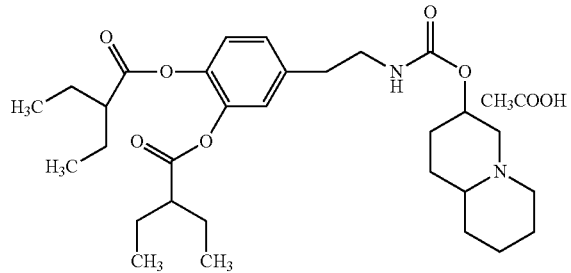

4-(2-((((octahydro-1H-quinolizin-3-yl)oxy)carbonyl)amino)ethyl)-1,2-phenylene bis(2-ethylbutanoate) acetate In this example, a dopamine.HCl solution was prepared by adding dopamine.HCl (19 g) into acetone (200 mL). Water (200 mL) and sodium bicarbonate (R0090, 50 g) were added into the dopamine.HCl solution to provide a 1st mixture. Then di-tert-butyl dicarbonate (22 g) was added to the 1st mixture to provide a 2nd mixture. The 2nd mixture was stirred at RT overnight, and added ethyl acetate (R0061, 500 mL) for extraction. The organic layer was separated, and washed with water (2×100 mL), 20% citric acid (2×200 mL), and water (3×100 mL), respectively, and dried over sodium sulfate to provide a 3rd solution. Then the sodium sulfate was filtered and washed with ethyl acetate to provide a 4th mixture. The 3rd solution and the 4th mixture were combined, and added first with pyridine (R0081, 30 mL), and then with 2-ethylbutyryl chloride (28 g) drop by drop to provide a 5th mixture. The 5th mixture was stirred at RT for 2 hours, then washed with water (2×100 mL), 5% sodium bucarbonate (2×100 mL), water (100 mL), 20% citric acid (2×200 mL), and water (3×100 mL), respectively, and dried over sodium sulfate to provide a 6th solution. The sodium sulfate was filtered and washed with ethyl acetate to provide a 7th solution. The 6th solution and the 7th solution were combined and concentrated to about 200 mL (an 8th solution). Into the 8th solution was added anisole (20 g), and then bubbled HCl gas (20 g) to form precipitation. The precipitated solid was collected and washed with ethyl acetate to yield 4-(2-((((-octahydro-1H-quinolizin-3-yl)oxy)carbonyl)amino)ethyl)-1,2,-phenylene bis(2-ethylbutanoate) hydrochloride salt.

The solid was suspended in ethyl acetate (200 mL) to provide a 9th mixture. Into the 9th mixture was first added triethylamine (25 mL), and then drop by drop with octahydro-1H-quinolizin-3-yl carbonochloride hydrochloride (22 g) in ethyl acetate (50 mL) to provide a 10th mixture. The 10th mixture was stirred for 2 hours at RT, washed with 5% sodium bicarbonate and water to provide a 11th mixture. Acetic acid (6 g) was added into the 11th mixture, followed by addition of hexane (200 mL) to provide precipitation. The precipitated solid was collected by filtration and washed with ethyl acetate/hexanes to yield 4-(2-((((-octahydro-1H-quinolizin-3-yl)oxy)carbonyl)amino)ethyl)-1,2,-phenylene bis(2-ethylbutanoate)acetate.

Example 8

Preparation of 1-(((2-(4-amino-2,5-dioxo-2,3,4,5-tetrahydrobenzo[b][1,4]dioxocin-8-yl)ethyl)carbamoyl)oxy)ethyl isobutyrate hydrofluoride and 1-(((2-(3-amino-2,5-dioxo-2,3,4,5-tetrahydrobenzo[b][1,4]dioxocin-8-yl)ethyl)carbamoyl)oxy)ethyl isobutyrate hydrofluoride

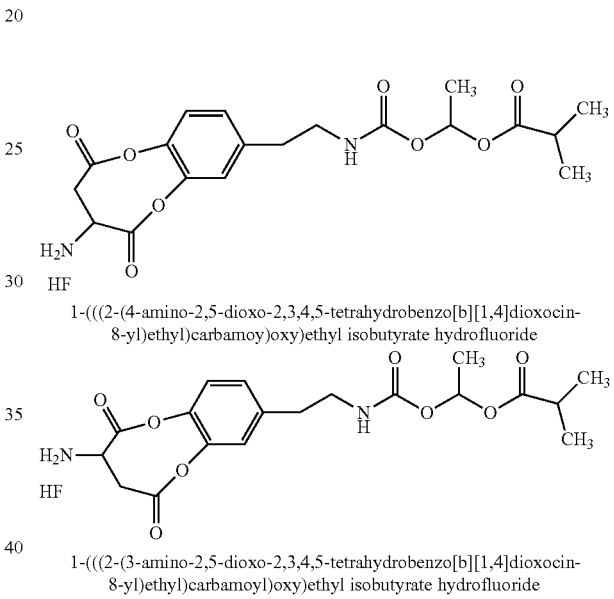

1-(((2-(4-amino-2,5-dioxo-2,3,4,5-tetrahydrobenzo[b][1,4]dioxocin-8-yl)ethyl)carbamoy)oxy)ethyl isobutyrate hydrofluoride 1-(((2-(3-amino-2,5-dioxo-2,3,4,5-tetrahydrobenzo[b][1,4]dioxocin-8-yl)ethyl)carbamoyl)oxy)ethyl isobutyrate hydrofluoride In this example, a dopamine.HCl solution was prepared by adding dopamine.HCl (19 g) into acetone (200 mL). Water (200 mL) and sodium bicarbonate (R0090, 50 g) were added into the dopamine.HCl solution to provide a 1st mixture. Then Nα-(benzyloxycarbonyloxy)succinimide (25 g) was added to the 1st mixture to provide a 2nd mixture. The 2nd mixture was stirred at RT overnight, and added ethyl acetate (R0061, 500 mL) for extraction. The organic layer was separated, and washed with water (2×100 mL), 20% citric acid (2×200 mL), and water (3×100 mL), respectively, and dried over sodium sulfate to provide a 3rd solution. Then the sodium sulfate was filtered and washed with ethyl acetate to provide a 4th mixture. The 3rd solution and the 4th mixture were combined, and evaporated to dryness. The obtained residue and Boc-L-aspartic acid (24 g) were dissolved in acetone (300 mL) to provide a 5th mixture. 1-Ethyl-(3-dimethylaminopropyl)carbodiimide hydrochloride (40 g) and 4-dimethylaminopyridine (22 g) were added into the 5th mixture to provide a 6th mixture. The 6th mixture was stirred overnight at RT and evaporated to dryness. Ethyl acetate (500 ml) was added into the residue to provide a 7th mixture, which was washed with water (2×100 mL), 5% sodium bucarbonate (3×100 mL), water (100 mL), 20% citric acid (2×200 mL), and water (3×100 mL), respectively, and dried over sodium sulfate to provide a 8th solution. The sodium sulfate was filtered and washed with ethyl acetate to provide a 9th solution. The 8th solution and the 9th solution were combined and evaporated to dryness. The residue was dissolved in methanol (R0084, 300 mL) to provide a 10th mixture. To the 10th mixture was added first palladium on activated charcoal (10 g, 10%) under nitrogen, and then bubbled with hydrogen gas to remove benzyloxycarbonyl group at RT. The obtained mixture (11th mixture) was filtered to remove the palladium on activated charcoal, and evaporated to dryness.

The residue was suspended in DCM (200 mL) to provide a 12th mixture. Sodium bicarbonate (20 g) and tetrabutylammonium hydrogen sulfate (11 g) were added into the 12th mixture to provide a 13th mixture. Then 1-chloroethyl chloroformate (16 g) was added into the 13th mixture to provide an 14th mixture. The 14th mixture was stirred at RT overnight. Then the organic layer of the 14th mixture was collected and washed with water (3×200 mL), and dried over anhydrous sodium sulfate to provide a 15th solution. The sodium sulfate was removed by filtration and washed with DCM to provide a 16th solution. The 15th solution and the 16th solution were combined and evaporated to dryness. The residue was dissolved in isobutyric acid (100 mL) to provide a 17th mixture. A mixture of diisopropylethylamine (60 mL) and isobutyric acid (36 mL) was prepared first and then added into the 17th mixture to provide a 18th mixture. The 18th mixture was stirred at 55° C. for 48 hours, and added ethyl acetate (500 mL) with stirring. The obtained organic layer was collected and washed with 5% sodium bicarbonate (3×100 mL) and water (3×100 mL), respectively, and dried over anhydrous sodium sulfate to provide a 19th solution. The sodium sulfate was filtered and washed with ethyl acetate to provide a 20th solution. The 19th solution and the 20th solution were combined and concentrated to 300 mL. Into the concentrated solution was added anisole (20 g) and then bubbled HF gas (20 g) to provide precipitation. The precipitated solid was collected and washed with ethyl acetate to yield 1-(((2-(4-amino-2,5-dioxo-2,3,4,5-tetrahydrobenzo[b][1,4]dioxocin-8-yl)ethyl)carbamoyl)oxy)ethyl isobutyrate hydrofluoride and 1-(((2-(3-amino-2,5-dioxo-2,3,4,5-tetrahydrobenzo[b][1,4]dioxocin-8-yl)ethyl)carbamoyl)oxy)ethyl isobutyrate hydrofluoride.

Example 9

Preparation of 4-(2-((ethoxycarbonyl)amino)ethyl)-2-(2-methylamino)acetoxy)phenyl benzoate hydrochloride and 5-(2-((ethoxycarbonyl)amino)ethyl)-2-(2-methylamino)acetoxy)phenyl benzoate hydrochloride

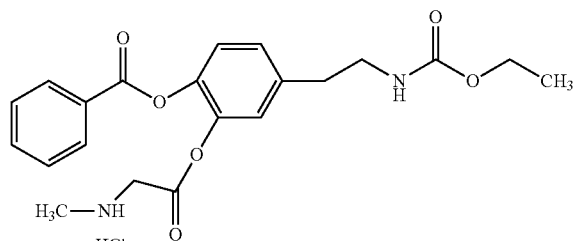

4-(2-((ethoxycarbonyl)amino)ethyl)-2-(2-(methylamino)acetoxy)phenyl benzoate hydrochloride

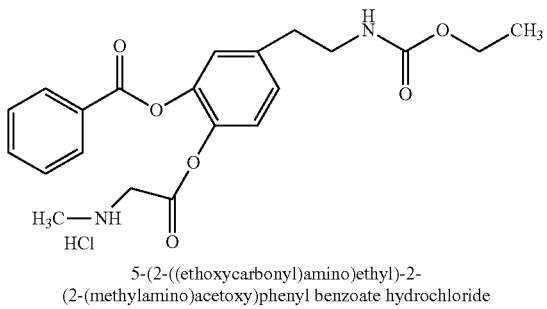

5-(2-((ethoxycarbonyl)amino)ethyl)-2-(2-(methylamino)acetoxy)phenyl benzoate hydrochloride In this example, a dopamine.HCl solution was prepared by adding dopamine.HCl (19 g) into acetone (200 mL). Pyridine (40 ml) was added into the dopamine.HCl solution to provide a 1st mixture. Then N-(ethoxycarbonyloxy)succinimide (18 g) was added to the 1st mixture to provide a 2nd mixture. The 2nd mixture was stirred at RT overnight, and added ethyl acetate (R0061, 500 mL) for extraction. The organic layer was separated, and washed with water (2×100 mL), 20% citric acid (2×200 mL), and water (3×100 mL), respectively, and dried over sodium sulfate to provide a 3rd solution. Then the sodium sulfate was filtered and washed with ethyl acetate to provide a 4th mixture. The 3rd solution and the 4th mixture were combined, and evaporated to dryness. The obtained residue and Trt-sarcocine (36 g) were dissolved in acetone (300 mL) to provide a 5th mixture. 1-Ethyl-(3-dimethylaminopropyl)carbodiimide hydrochloride (20 g) and 4-dimethylaminopyridine (12 g) were added into the 5th mixture to provide a 6th mixture. The 6th mixture was stirred overnight at RT and evaporated to dryness. Ethyl acetate (500 ml) was added into the residue to provide a 7th mixture, which was washed with water (2×100 mL), 5% sodium bucarbonate (3×100 mL), water (100 mL), 20% citric acid (2×200 mL), and water (3×100 mL), respectively, and dried over sodium sulfate to provide a 8th solution. The sodium sulfate was filtered and washed with ethyl acetate to provide a 9th solution. To the combined 8th solution and the 9th solution were added pyridine (20 mL) and then drop by drop added benzoyl chloride (15 g) to provide a 10th mixture.

The 10th mixture was stirred at RT for 4 hours, and washed with water (2×100 mL), 5% sodium bucarbonate (2×100 mL), water (100 mL), 20% citric acid (2×200 mL), and water (3×100 mL), respectively, and dried over sodium sulfate to provide a 11th solution. The sodium sulfate was filtered and washed with ethyl acetate to provide a 12th solution.

Into the combined 11th and 12th solutions was added anisole (20 g) and then bubbled HCl gas (20 g) to provide precipitation. The precipitated solid was collected and washed with ethyl acetate to yield 4-(2-((ethoxycarbonyl)amino)ethyl)-2-(2-methylamino)acetoxy)phenyl benzoate hydrochloride and 5-(2-((ethoxycarbonyl)amino)ethyl)-2-(2-methylamino)acetoxy)phenyl benzoate.

Example 10

Preparation of 4-(2-aminoethyl)-1,2-phenylene dibenzoate hydrochloride

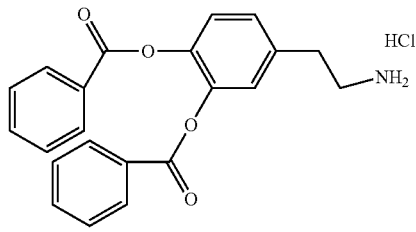

4-(2-aminoethyl)-1,2-phenylene dibenzoate hydrochloride

In this example, a dopamine.HCl solution was prepared by adding dopamine.HCl (19 g) into acetone (200 mL). Water (200 mL) and sodium bicarbonate (R0090, 50 g) were added into the dopamine.HCl solution to provide a 1st mixture. Then di-tert-butyl dicarbonate (22 g) was added to the 1st mixture to provide a 2nd mixture. The 2nd mixture was stirred at RT overnight, and added ethyl acetate (R0061, 500 mL) for extraction. The organic layer was separated, and washed with water (2×100 mL), 20% citric acid (2×200 mL), and water (3×100 mL), respectively, and dried over sodium sulfate to provide a 3rd solution. Then the sodium sulfate was filtered and washed with ethyl acetate to provide a 4th mixture. The 3rd solution and the 4th mixture were combined, and added first with pyridine (R0081, 30 mL), and then with benzoyl chloride (R0488, 30 g) drop by drop to provide a 5th mixture. The 5th mixture was stirred at RT for 2 hours, then washed with water (2×100 mL), 5% sodium bucarbonate (3×100 mL), water (100 mL), 20% citric acid (2×200 mL), and water (3×100 mL), respectively, and dried over sodium sulfate to provide a 6th solution. The sodium sulfate was filtered and washed with ethyl acetate to provide a 7th solution. The 6th solution and the 7th solution were combined and concentrated to about 300 mL (an 8th solution). Into the 8th solution was added anisole (20 g), and then bubbled HCl gas (60 g) to form precipitation. The precipitated solid was collected and washed with ethyl acetate to yield 4-(2-aminoethyl)-1,2-phenylene dibenzoate hydrochloride.

Example 11

Preparation of (S)-4-(2-amino-3-isopropoxy-3-oxopropyl)-1,2-phenylene dibenzoate hydrochloride

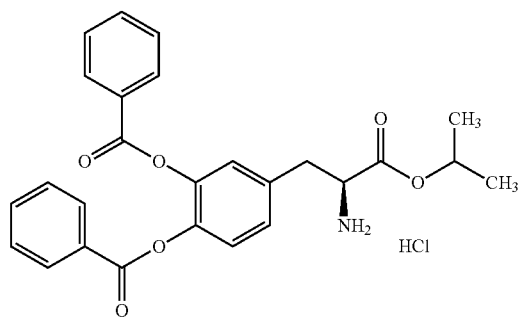

(S)-4-(2-amino-3-isopropoxy-3-oxopropyl)-1,2-phenylene dibenzoate hydrochloride

In this example, (S)-2-amino-3-(3,4-dihydroxyphenyl) propanoic acid (20 g) was added into isopropanol (200 mL) to provide a 1st mixture. HCl gas (20 g) was bubbled into the 1st mixture to provide a 2nd mixture. The 2nd mixture was stirred for 2 days at 60° C., and then added with isopropyl acetate (200 mL) to provide precipitation. The precipitated solid was collected and washed with isopropayl acetate to provide isopropyl (S)-2-amino-3-(3,4-dihydroxyphenyl) propanoate hydrochloride.

Isopropyl (S)-2-amino-3-(3,4-dihydroxyphenyl)propanoate hydrochloride (28 g) was added into acetone (200 mL) to provide a 3rd mixture. Into the 3rd mixture was added water (200 mL) and sodium bicarbonate (50 g), and then di-tert-butyl dicarbonate (22 g) to provide a 4th mixture. The 4th mixture was stirred for overnight at RT, and added ethyl acetate (500 mL). The organic layer (5th mixture) was washed with water (2×100 mL), 20% citric acid (2×200 mL), and water (3×100 mL), respectively, and dried over anhydrous sodium sulfate to provide a 6th solution. Then the sodium sulfate was filtered and washed with ethyl acetate to provide a 7th mixture. The 6th solution and the 7th mixture were combined, and added first with pyridine (R0081, 30 mL), and then with benzoyl chloride (R0488, 30 g) drop by drop to provide an 8th mixture. The 8th mixture was stirred at RT for 2 hours, then washed with water (2×100 mL), 5% sodium bucarbonate (3×100 mL), water (100 mL), 20% citric acid (2×200 mL), and water (3×100 mL), respectively, and dried over sodium sulfate to provide a 9th solution. The sodium sulfate was filtered and washed with ethyl acetate to provide a 10th solution. The 9th solution and the 10th solution were combined and concentrated to about 300 mL (an 11th solution). Into the 11th solution was added anisole (20 g), and then bubbled HCl gas (20 g) to form precipitation. The precipitated solid was collected and washed with ethyl acetate to yield (S)-4-(2-amino-3-isopropoxy-3-oxopropyl)-1,2-phenylene dibenzoate hydrochloride.

Example 12

Preparation of (S)-4-(2-amino-3-(heptan-4-yloxy)-3-oxopropyl)-1,2-phenylene dibenzoate hydrochloride

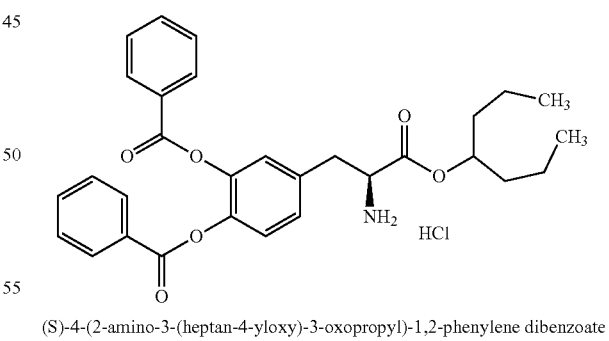

(S)-4-(2-amino-3-(heptan-4-yloxy)-3-oxopropyl)-1,2-phenylene dibenzoate

In this example, (S)-2-amino-3-(3,4-dihydroxyphenyl) propanoic acid (20 g) was added into 4-heptanol (200 mL) to provide a 1st mixture. HCl gas (20 g) was bubbled into the 1st mixture to provide a 2nd mixture. The 2nd mixture was stirred for 2 days at 60° C., and then added with isopropyl acetate (200 mL) to provide precipitation. The precipitated solid was collected and washed with isopropayl acetate to provide 4-heptyl (S)-2-amino-3-(3,4-dihydroxyphenyl)propanoate hydrochloride.

4-Heptyl (S)-2-amino-3-(3,4-dihydroxyphenyl)propanoate hydrochloride (28 g) was added into acetone (200 mL) to provide a 3rd mixture. Into the 3rd mixture was added water (200 mL) and sodium bicarbonate (50 g), and then di-tert-butyl dicarbonate (22 g) to provide a 4th mixture. The 4th mixture was stirred for overnight at RT, and added ethyl acetate (500 mL). The organic layer (5th mixture) was washed with water (2×100 mL), 20% citric acid (2×200 mL), and water (3×100 mL), respectively, and dried over anhydrous sodium sulfate to provide a 6th solution. Then the sodium sulfate was filtered and washed with ethyl acetate to provide a 7th mixture. The 6th solution and the 7th mixture were combined, and added first with pyridine (R0081, 30 mL), and then with benzoyl chloride (R0488, 30 g) drop by drop to provide an 8th mixture. The 8th mixture was stirred at RT for 2 hours, then washed with water (2×100 mL), 5% sodium bucarbonate (3×100 mL), water (100 mL), 20% citric acid (2×200 mL), and water (3×100 mL), respectively, and dried over sodium sulfate to provide a 9th solution. The sodium sulfate was filtered and washed with ethyl acetate to provide a 10th solution. The 9th solution and the 10th solution were combined and concentrated to about 300 mL (an 11th solution). Into the 11th solution was added anisole (20 g), and then bubbled HCl gas (20 g) to form precipitation. The precipitated solid was collected and washed with ethyl acetate to yield (S)-4-(2-amino-3-(heptan-4-yloxy)-3-oxopropyl)-1,2-phenylene dibenzoate hydrochloride.

Example 13

Preparation of (S)-4-(2-amino-3-isopropoxy-3-oxopropyl)-1,2-phenylene dipentanoate hydrochloride

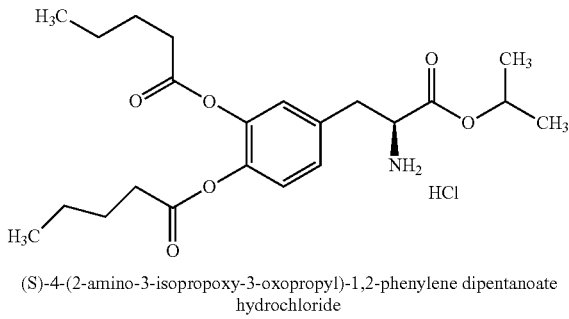 [SMILES: CCCCC(=O)Oc1ccc(C[C@H](N)C(=O)OC(C)C)cc1OC(=O)CCCC ; Cl]

(S)-4-(2-amino-3-isopropoxy-3-oxopropyl)-1,2-phenylene dipentanoate hydrochloride In this example, (S)-2-amino-3-(3,4-dihydroxyphenyl)propanoic acid (20 g) was added into isopropanol (200 mL) to provide a 1st mixture. HCl gas (20 g) was bubbled into the 1st mixture to provide a 2nd mixture. The 2nd mixture was stirred for 2 days at 60° C., and then added with isopropyl acetate (200 mL) to provide precipitation. The precipitated solid was collected and washed with isopropayl acetate to provide isopropyl (S)-2-amino-3-(3,4-dihydroxyphenyl)propanoate hydrochloride.

Isopropyl (S)-2-amino-3-(3,4-dihydroxyphenyl)propanoate hydrochloride (28 g) was added into acetone (200 mL) to provide a 3rd mixture. Into the 3rd mixture was added water (200 mL) and sodium bicarbonate (50 g), and then di-tert-butyl dicarbonate (22 g) to provide a 4th mixture. The 4th mixture was stirred for overnight at RT, and added ethyl acetate (500 mL). The organic layer (5th mixture) was washed with water (2×100 mL), 20% citric acid (2×200 mL), and water (3×100 mL), respectively, and dried over anhydrous sodium sulfate to provide a 6th solution. Then the sodium sulfate was filtered and washed with ethyl acetate to provide a 7th mixture. The 6th solution and the 7th mixture were combined, and added first with pyridine (R0081, 30 mL), and then with pentanoyl chloride (24 g) drop by drop to provide an 8th mixture. The 8th mixture was stirred at RT for 2 hours, then washed with water (2×100 mL), 5% sodium bucarbonate (3×100 mL), water (100 mL), 20% citric acid (2×200 mL), and water (3×100 mL), respectively, and dried over sodium sulfate to provide a 9th solution. The sodium sulfate was filtered and washed with ethyl acetate to provide a 10th solution. The 9th solution and the 10th solution were combined and concentrated to about 300 mL (an 11th solution). Into the 11th solution was added anisole (20 g), and then bubbled HCl gas (20 g) to form precipitation. The precipitated solid was collected and washed with ethyl acetate to yield (S)-4-(2-amino-3-isopropoxy-3-oxopropyl)-1,2-phenylene dipentanoate hydrochloride.

Example 14

Preparation of (S)-4-(2-amino-3-ethoxy-3-oxopropyl)-1,2-phenylene diacetate hydrochloride

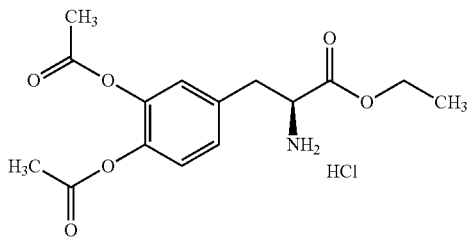

(S)-4-(2-amino-3-ethoxy-3-oxopropyl)-1,2-phenylene dicacetate hydrochloride

In this example, (S)-2-amino-3-(3,4-dihydroxyphenyl)propanoic acid (20 g) was added into ethanol (200 mL) to provide a 1st mixture. HCl gas (20 g) was bubbled into the 1st mixture to provide a 2nd mixture. The 2nd mixture was stirred for 2 days at 60° C., and then added with isopropyl acetate (200 mL) to provide precipitation. The precipitated solid was collected and washed with isopropayl acetate to provide ethyl (S)-2-amino-3-(3,4-dihydroxyphenyl)propanoate hydrochloride.

Ethyl (S)-2-amino-3-(3,4-dihydroxyphenyl)propanoate hydrochloride (26 g) was added into acetone (200 mL) to provide a 3rd mixture. Into the 3rd mixture was added water (200 mL) and sodium bicarbonate (50 g), and then di-tert-butyl dicarbonate (22 g) to provide a 4th mixture. The 4th mixture was stirred for overnight at RT, and added ethyl acetate (500 mL). The organic layer (5th mixture) was washed with water (2×100 mL), 20% citric acid (2×200 mL), and water (3×100 mL), respectively, and dried over anhydrous sodium sulfate to provide a 6th solution. Then the sodium sulfate was filtered and washed with ethyl acetate to provide a 7th mixture. The 6th solution and the 7th mixture were combined, and added first with pyridine (R0081, 30 mL), and then with acetyl chloride (18 g) drop by drop to provide an 8th mixture. The 8th mixture was stirred at RT for 2 hours, then washed with water (2×100 mL), 5% sodium bucarbonate (3×100 mL), water (100 mL), 20% citric acid (2×200 mL), and water (3×100 mL), respectively, and dried over sodium sulfate to provide a 9th solution. The sodium sulfate was filtered and washed with ethyl acetate to provide a 10th solution. The 9th solution and the 10th solution were combined and concentrated to about 300 mL (an 11th solution). Into the 11th solution was added anisole (20 g), and then bubbled HCl gas (20 g) to form precipitation. The precipitated solid was collected and washed with ethyl acetate to yield (S)-4-(2-amino-3-ethoxy-3-oxopropyl)-1,2-phenylene diacetate hydrochloride.

Example 15

Preparation of (S)-4-(2-amino-3-oxo-3-(pentan-3-yloxy)propyl)-1,2-phenylene bis(2-methylpropanoate) hydrobromide

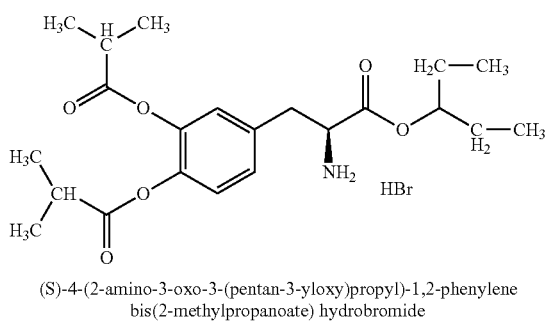 [SMILES: CCC(CC)OC(=O)[C@@H](N)Cc1ccc(OC(=O)C(C)C)c(OC(=O)C(C)C)c1 ; Br]

(S)-4-(2-amino-3-oxo-3-(pentan-3-yloxy)propyl)-1,2-phenylene bis(2-methylpropanoate) hydrobromide In this example, (S)-2-amino-3-(3,4-dihydroxyphenyl)propanoic acid (20 g) was added into 3-pentanol (200 mL) to provide a 1st mixture. HCl gas (20 g) was bubbled into the 1st mixture to provide a 2nd mixture. The 2nd mixture was stirred for 2 days at 60° C., and then added with isopropyl acetate (200 mL) to provide precipitation. The precipitated solid was collected and washed with isopropayl acetate to provide isopropyl (S)-2-amino-3-(3,4-dihydroxyphenyl)propanoate hydrochloride.

3-Pentyl (S)-2-amino-3-(3,4-dihydroxyphenyl)propanoate hydrochloride (28 g) was added into acetone (200 mL) to provide a 3rd mixture. Into the 3rd mixture was added water (200 mL) and sodium bicarbonate (50 g), and then di-tert-butyl dicarbonate (22 g) to provide a 4th mixture. The 4th mixture was stirred for overnight at RT, and added ethyl acetate (500 mL). The organic layer (5th mixture) was washed with water (2×100 mL), 20% citric acid (2×200 mL), and water (3×100 mL), respectively, and dried over anhydrous sodium sulfate to provide a 6th solution. Then the sodium sulfate was filtered and washed with ethyl acetate to provide a 7th mixture. The 6th solution and the 7th mixture were combined, and added first with pyridine (R0081, 30 mL), and then with isobutyryl chloride (22 g) drop by drop to provide an 8th mixture. The 8th mixture was stirred at RT for 2 hours, then washed with water (2×100 mL), 5% sodium bucarbonate (3×100 mL), water (100 mL), 20% citric acid (2×200 mL), and water (3×100 mL), respectively, and dried over sodium sulfate to provide a 9th solution. The sodium sulfate was filtered and washed with ethyl acetate to provide a 10th solution. The 9th solution and the 10th solution were combined and concentrated to about 300 mL (an 11th solution). Into the 11th solution was added anisole (20 g), and then bubbled HCl gas (20 g) to form precipitation. The precipitated solid was collected and washed with ethyl acetate to yield (S)-4-(2-amino-3-ethoxy-3-oxopropyl)-1,2-phenylene diacetate hydrochloride.

Example 16

Preparation of (S)-4-(2-aminoacetamido)-3-isopropoxy-3-oxopropyl)-1,2-phenylene dibenzoate hydrochloride

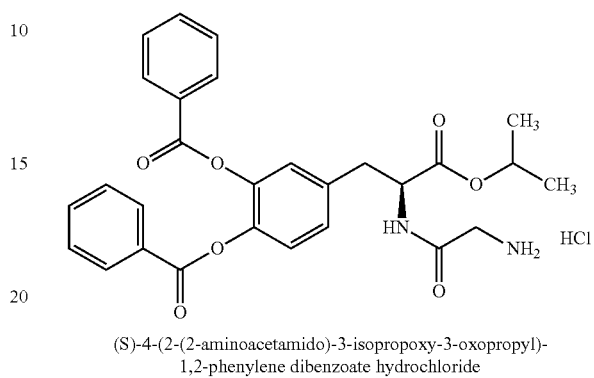

(S)-4-(2-(2-aminoacetamido)-3-isopropoxy-3-oxopropyl)-1,2-phenylene dibenzoate hydrochloride In this example, (S)-2-amino-3-(3,4-dihydroxyphenyl) propanoic acid (20 g) was added into isopropanol (200 mL) to provide a 1st mixture. HCl gas (20 g) was bubbled into the 1st mixture to provide a 2nd mixture. The 2nd mixture was stirred for 2 days at 60° C., and then added with isopropyl acetate (200 mL) to provide precipitation. The precipitated solid was collected and washed with isopropayl acetate to provide isopropyl (S)-2-amino-3-(3,4-dihydroxyphenyl) propanoate hydrochloride.

Isopropyl (S)-2-amino-3-(3,4-dihydroxyphenyl)propanoate hydrochloride (28 g) was added into acetone (200 mL) to provide a 3rd mixture. Into the 3rd mixture was added water (200 mL) and sodium bicarbonate (50 g), and then N-(tert-Butoxycarbonyl-glycine N-hydroxysuccinimide ester (27 g) to provide a 4th mixture. The 4th mixture was stirred for overnight at RT, and added ethyl acetate (500 mL). The organic layer (5th mixture) was washed with water (2×100 mL), 20% citric acid (2×200 mL), and water (3×100 mL), respectively, and dried over anhydrous sodium sulfate to provide a 6th solution. Then the sodium sulfate was filtered and washed with ethyl acetate to provide a 7th mixture. The 6th solution and the 7th mixture were combined, and added first with pyridine (R0081, 30 mL), and then with benzoyl chloride (30 g) drop by drop to provide an 8th mixture. The 8th mixture was stirred at RT for 2 hours, then washed with water (2×100 mL), 5% sodium bucarbonate (3×100 mL), water (100 mL), 20% citric acid (2×200 mL), and water (3×100 mL), respectively, and dried over sodium sulfate to provide a 9th solution. The sodium sulfate was filtered and washed with ethyl acetate to provide a 10th solution. The 9th solution and the 10th solution were combined and concentrated to about 300 mL (an 11th solution). Into the 11th solution was added anisole (20 g), and then bubbled HCl gas (20 g) to form precipitation. The precipitated solid was collected and washed with ethyl acetate to yield (S)-4-(2-aminoacetamido)-3-isopropoxy-3-oxopropyl)-1,2-phenylene dibenzoate hydrochloride.

Example 17

Preparation of 4-((2S)-3-oxo-3-(pentan-3-yloxy)-2-(pyrrolidine-2-carboxamido)propyl)-1,2-phenylene dibenzoate hydrofluoride

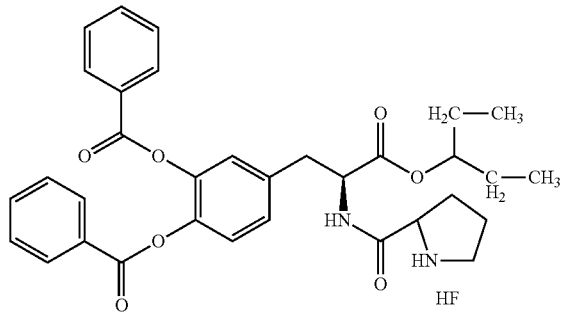

4-((2S)-3-oxo-3-(pentan-3-yloxy)-2-(pyrrolidine-2-carboxamido)propyl)-1,2-phenylene dibenzoate hydrofluoride In this example, (S)-2-amino-3-(3,4-dihydroxyphenyl) propanoic acid (20 g) was added into 3-pentanol (200 mL) to provide a 1st mixture. HCl gas (20 g) was bubbled into the 1st mixture to provide a 2nd mixture. The 2nd mixture was stirred for 2 days at 60° C., and then added with isopropyl acetate (200 mL) to provide precipitation. The precipitated solid was collected and washed with isopropayl acetate to provide isopropyl (S)-2-amino-3-(3,4-dihydroxyphenyl) propanoate hydrochloride.

3-Pentyl (S)-2-amino-3-(3,4-dihydroxyphenyl)propanoate hydrochloride (28 g) was added into acetone (200 mL) to provide a 3rd mixture. Into the 3rd mixture was added water (200 mL) and sodium bicarbonate (50 g), and then N-(tert-Butoxycarbonyl-proline N-hydroxysuccinimide ester (32 g) to provide a 4th mixture. The 4th mixture was stirred for overnight at RT, and added ethyl acetate (500 mL). The organic layer (5th mixture) was washed with water (2×100 mL), 20% citric acid (2×200 mL), and water (3×100 mL), respectively, and dried over anhydrous sodium sulfate to provide a 6th solution. Then the sodium sulfate was filtered and washed with ethyl acetate to provide a 7th mixture. The 6th solution and the 7th mixture were combined, and added first with pyridine (R0081, 30 mL), and then with benzoyl chloride (22 g) drop by drop to provide an 8th mixture. The 8th mixture was stirred at RT for 2 hours, then washed with water (2×100 mL), 5% sodium bucarbonate (3×100 mL), water (100 mL), 20% citric acid (2×200 mL), and water (3×100 mL), respectively, and dried over sodium sulfate to provide a 9th solution. The sodium sulfate was filtered and washed with ethyl acetate to provide a 10th solution. The 9th solution and the 10th solution were combined and concentrated to about 300 mL (an 11th solution). Into the 11th solution was added anisole (20 g), and then bubbled HF gas (20 g) to form precipitation. The precipitated solid was collected and washed with ethyl acetate to yield 4-((2S)-3-oxo-3-(pentan-3-yloxy)-2-(pyrrolidine-2-carboxamido)propyl)-1,2-phenylene dibenzoate hydrofluoride.

Example 18

Preparation of (S)-4-(3-isopropoxy-3-oxo-2-(piperidine-4-carboxamido)propyl)-1,2-phenylene dibenzoate hydrofluoride

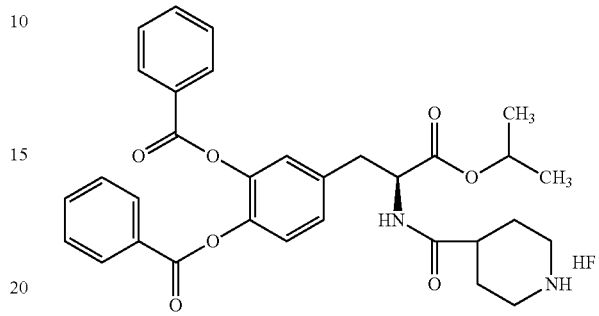

(S)-4-(3-isopropoxy-3-oxo-2-(piperidine-4-carboxamido)propyl)-1,2-phenylene dibenzoate hydrofluoride In this example, (S)-2-amino-3-(3,4-dihydroxyphenyl) propanoic acid (20 g) was added into isopropanol (200 mL) to provide a 1st mixture. HCl gas (20 g) was bubbled into the 1st mixture to provide a 2nd mixture. The 2nd mixture was stirred for 2 days at 60° C., and then added with isopropyl acetate (200 mL) to provide precipitation. The precipitated solid was collected and washed with isopropayl acetate to provide isopropyl (S)-2-amino-3-(3,4-dihydroxyphenyl) propanoate hydrochloride.

Isopropyl (S)-2-amino-3-(3,4-dihydroxyphenyl)propanoate hydrochloride (28 g) was added into acetone (200 mL) to provide a 3rd mixture. Into the 3rd mixture was added water (200 mL) and sodium bicarbonate (50 g), and then Boc-piperidine-4-carboxylic acid N-hydroxysuccinimide ester (Boc-Inp-OSu, 33 g) to provide a 4th mixture. The 4th mixture was stirred for overnight at RT, and added ethyl acetate (500 mL). The organic layer (5th mixture) was washed with water (2×100 mL), 20% citric acid (2×200 mL), and water (3×100 mL), respectively, and dried over anhydrous sodium sulfate to provide a 6th solution. Then the sodium sulfate was filtered and washed with ethyl acetate to provide a 7th mixture. The 6th solution and the 7th mixture were combined, and added first with pyridine (R0081, 30 mL), and then with benzoyl chloride (30 g) drop by drop to provide an 8th mixture. The 8th mixture was stirred at RT for 2 hours, then washed with water (2×100 mL), 5% sodium bucarbonate (3×100 mL), water (100 mL), 20% citric acid (2×200 mL), and water (3×100 mL), respectively, and dried over sodium sulfate to provide a 9th solution. The sodium sulfate was filtered and washed with ethyl acetate to provide a 10th solution. The 9th solution and the 10th solution were combined and concentrated to about 300 mL (an 11th solution). Into the 11th solution was added anisole (20 g), and then bubbled HF gas (20 g) to form precipitation. The precipitated solid was collected and washed with ethyl acetate to yield (S)-4-(3-isopropoxy-3-oxo-2-(piperidine-4-carboxamido)propyl)-1,2-phenylene dibenzoate hydrofluoride.

Example 19

Preparation of 4-((2S)-3-isopropoxy-3-2-(octahydro-1H-quinolizine-2-carboxamido)-3-oxopropyl)-1,2-phenylene bis(2-methylpropanoate) hydrochloride

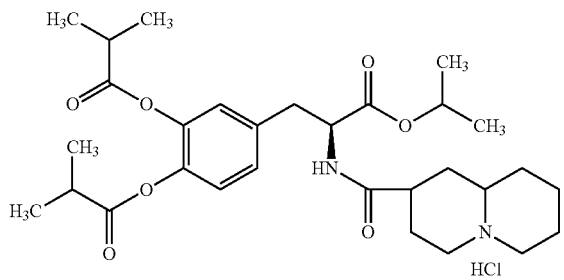

4-((2S)-3-isopropoxy-2-(octahydro-1H-quinolizine-2-carboxamido)-3-oxopropyl)-1,2-phenylene bis(2-methylpropanoate) hydrochloride In this example, (S)-2-amino-3-(3,4-dihydroxyphenyl)propanoic acid (20 g) was added into isopropanol (200 mL) to provide a 1st mixture. HCl gas (20 g) was bubbled into the 1st mixture to provide a 2nd mixture. The 2nd mixture was stirred for 2 days at 60° C., and then added with isopropyl acetate (200 mL) to provide precipitation. The precipitated solid was collected and washed with isopropayl acetate to provide isopropyl (S)-2-amino-3-(3,4-dihydroxyphenyl)propanoate hydrochloride.

Isopropyl (S)-2-amino-3-(3,4-dihydroxyphenyl)propanoate hydrochloride (28 g) was added into acetone (200 mL) to provide a 3rd mixture. Into the 3rd mixture was added water (200 mL) and sodium bicarbonate (50 g), and then octahydro-1H-quinolizine-2-carboxylic acid N-hydroxysuccinimide ester (28 g) to provide a 4th mixture. The 4th mixture was stirred for overnight at RT, and added ethyl acetate (500 mL). The organic layer (5th mixture) was washed with water (2×100 mL), 20% citric acid (2×200 mL), and water (3×100 mL), respectively, and dried over anhydrous sodium sulfate to provide a 6th solution. Then the sodium sulfate was filtered and washed with ethyl acetate to provide a 7th mixture. The 6th solution and the 7th mixture were combined, and added first with pyridine (R0081, 30 mL), and then with isobutyryl chloride (22 g) drop by drop to provide an 8th mixture. The 8th mixture was stirred at RT for 2 hours, then washed with water (2×100 mL), 5% sodium bucarbonate (3×100 mL), water (100 mL), 20% citric acid (2×200 mL), and water (3×100 mL), respectively, and dried over sodium sulfate to provide a 9th solution. The sodium sulfate was filtered and washed with ethyl acetate to provide a 10th solution. The 9th solution and the 10th solution were combined and concentrated to about 100 mL (an 11th solution). Into the 11th solution was added hexane (200 mL), and then acetic acid (6 g) to form precipitation. The precipitated solid was collected and washed with ethyl acetate/hexane to 4-((2S)-3-isopropoxy-3-2-(octahydro-1H-quinolizine-2-carboxamido)-3-oxopropyl)-1,2-phenylene bis(2-methylpropanoate) hydrochloride.

Example 20

Preparation of (2S)-isopropyl 3-(3-amino-2,5-dioxo-2,3,4,5-tetrahydrobenzo[b][1,4]dioxocin-8-yl)-2-(((1-(isobutyryloxy)ethoxy)carbonyl)amino)propanoate hydrobromide and (2S)-isopropyl 3-(4-amino-2,5-dioxo-2,3,4,5-tetrahydrobenzo[b][1,4]dioxocin-8-yl)-2-(((1-(isobutyryloxy)ethoxy)carbonyl)amino)propanoate hydrobromide

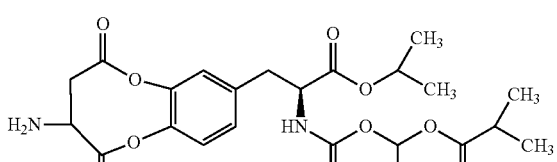

(2S)-isopropyl 3-(3-amino-2,5-dioxo-2,3,4,5-tetrahydrobenzo[b][1,4]dioxocin-8-yl)-2-(((1-(isobutyryloxy)ethoxy)carbonyl)amino)propanoate hydrobromide

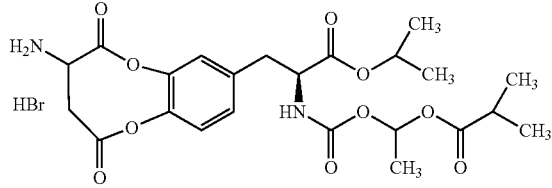

(2S)-isopropyl 3-(4-amino-2,5-dioxo-2,3,4,5-tetrahydrobenzo[b][1,4]dioxocin-8-yl)-2-(((1-(isobutyryloxy)ethoxy)carbonyl)amino)propanoate hydrobromide In this example, (S)-2-amino-3-(3,4-dihydroxyphenyl)propanoic acid (20 g) was added into isopropanol (200 mL) to provide a 1st mixture. HCl gas (20 g) was bubbled into the 1st mixture to provide a 2nd mixture. The 2nd mixture was stirred for 2 days at 60° C., and then added with isopropyl acetate (200 mL) to provide precipitation. The precipitated solid was collected and washed with isopropayl acetate to provide isopropyl (S)-2-amino-3-(3,4-dihydroxyphenyl)propanoate hydrochloride.

An isopropyl (S)-2-amino-3-(3,4-dihydroxyphenyl)propanoate hydrochloride solution was prepared by adding isopropyl (S)-2-amino-3-(3,4-dihydroxyphenyl)propanoate hydrochloride (28 g) into acetone (200 mL). Water (200 mL) and sodium bicarbonate (R0090, 50 g) were added into the dopamine.HCl solution to provide a 3rd mixture. Then Nα-(benzyloxycarbonyloxy)succinimide (25 g) was added to the 3rd mixture to provide a 4th mixture. The 4th mixture was stirred at RT overnight, and added ethyl acetate (R0061, 500 mL) for extraction. The organic layer was separated, and washed with water (2×100 mL), 20% citric acid (2×200 mL), and water (3×100 mL), respectively, and dried over sodium sulfate to provide a 5th solution. Then the sodium sulfate was filtered and washed with ethyl acetate to provide a 6th solution. The 5th solution and the 6th mixture were combined, and evaporated to dryness. The obtained residue and Boc-L-aspartic acid (24 g) were dissolved in acetone (300 mL) to provide a 7th mixture. 1-Ethyl-(3-dimethylaminopropyl)carbodiimide hydrochloride (40 g) and 4-dimethylaminopyridine (22 g) were added into the 7th mixture to provide an 8th mixture. The 8th mixture was stirred overnight at RT and evaporated to dryness. Ethyl acetate (500 ml) was added into the residue to provide a 9th mixture, which was washed with water (2×100 mL), 5% sodium bucarbonate (3×100 mL), water (100 mL), 20% citric acid (2×200 mL), and water (3×100 mL), respectively, and dried over sodium sulfate to provide a 10th solution. The sodium sulfate was filtered and washed with ethyl acetate to provide an 11th solution. The 10th solution and the 11th solution were combined and evaporated to dryness. The residue was dissolved in methanol (R0084, 300 mL) to provide a 12th mixture. To the 12th mixture was added first palladium on activated charcoal (10 g, 10%) under nitrogen, and then bubbled with hydrogen gas to remove benzyloxycarbonyl group at RT. The obtained mixture (13th mixture) was filtered to remove the palladium on activated charcoal, and evaporated to dryness.

The residue was suspended in DCM (200 mL) to provide a 14th mixture. Sodium bicarbonate (15 g) and tetrabutylammonium hydrogen sulfate (11 g) were added into the 14th mixture to provide a 15th mixture. Then 1-chloroethyl chloroformate (16 g) was added into the 15th mixture to provide a 16th mixture. The 16th mixture was stirred at RT overnight. Then the organic layer of the 16th mixture was collected and washed with water (3×200 mL), and dried over anhydrous sodium sulfate to provide a 17th solution. The sodium sulfate was removed by filtration and washed with DCM to provide a 18th solution. The 17th solution and the 18th solution were combined and evaporated to dryness. The residue was dissolved in isobutyric acid (100 mL) to provide a 19th mixture. A mixture of diisopropylethylamine (60 mL) and isobutyric acid (36 mL) was prepared first and then added into the 19th mixture to provide a 20th mixture. The 20th mixture was stirred at 55° C. for 48 hours, and added ethyl acetate (500 mL) with stirring. The obtained organic layer was collected and washed with 5% sodium bicarbonate (3×100 mL) and water (3×100 mL), respectively, and dried over anhydrous sodium sulfate to provide a 21st solution. The sodium sulfate was filtered and washed with ethyl acetate to provide a 22nd solution. The 21st solution and the 22nd solution were combined and concentrated to 300 mL. Into the concentrated solution was added anisole (20 g) and then bubbled HBr gas (30 g) to provide precipitation. The precipitated solid was collected and washed with ethyl acetate to yield (2S)-isopropyl 3-(3-amino-2,5-dioxo-2,3,4,5-tetrahydrobenzo[b][1,4]dioxocin-8-yl)-2-(((1-(isobutyryloxy)ethoxy)carbonyl)amino)propanoate hydrobromide and (2S)-isopropyl 3-(4-amino-2,5-dioxo-2,3,4,5-tetrahydrobenzo[b][1,4]dioxocin-8-yl)-2-(((1-(isobutyryloxy)ethoxy)carbonyl)amino)propanoate hydrobromide.

Example 21

Preparation of 5-((2S)-2-(((1-(isobutyryloxy)ethoxy)carbonyl)amino-3-isopropoxy-3-oxopropyl)-2-(2-(methylamino)acetoxy)phenyl benzoate hydrochloride and 4-((2S)-2-(((1-(isobutyryloxy)ethoxy)carbonyl)amino-3-isopropoxy-3-oxopropyl)-2-(2-(methylamino)acetoxy)phenyl benzoate hydrochloride

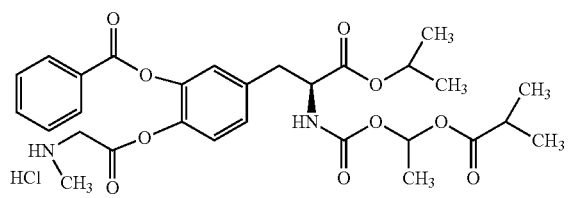

5-((2S)-2-(((1-(isobutyryloxy)ethoxy(carbonyl)amino)-3-isopropoxy-3-oxoproplyl)-2-(2-(methylamino)acetoxy)phenyl benzoate hydrochloride

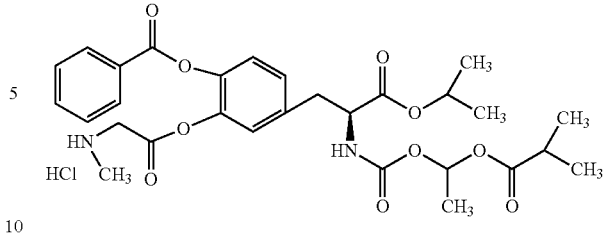

4-((2S)-2-(((1-(isobutyryloxy)ethoxy(carbonyl)amino)-3-isopropoxy-3-oxoproplyl)-2-(2-(methylamino)acetoxy)phenyl benzoate hydrochloride In this example, (S)-2-amino-3-(3,4-dihydroxyphenyl) propanoic acid (20 g) was added into isopropanol (200 mL) to provide a 1st mixture. HCl gas (20 g) was bubbled into the 1st mixture to provide a 2nd mixture. The 2nd mixture was stirred for 2 days at 60° C. and then added with isopropyl acetate (200 mL) to provide precipitation. The precipitated solid was collected and washed with isopropayl acetate to provide isopropyl (S)-2-amino-3-(3,4-dihydroxyphenyl) propanoate hydrochloride.

An isopropyl (S)-2-amino-3-(3,4-dihydroxyphenyl)propanoate hydrochloride solution was prepared by adding isopropyl (S)-2-amino-3-(3,4-dihydroxyphenyl)propanoate hydrochloride (28 g) into acetone (200 mL). Water (200 mL1) and sodium bicarbonate (R0090, 50 g) were added into the dopamine.HCl solution to provide a 3rd mixture. Then Nα-(benzyloxycarbonyloxy)succinimide (25 g) was added to the 3rd mixture to provide a 4th mixture. The 4th mixture was stirred at RT overnight, and added ethyl acetate (R0061, 500 mL) for extraction. The organic layer was separated, and washed with water (2×100 mL), 20% citric acid (2×200 mL), and water (3×100 mL), respectively, and dried over sodium sulfate to provide a 5th solution. Then the sodium sulfate was filtered and washed with ethyl acetate to provide a 6th solution. The 5th solution and the 6th mixture were combined, and evaporated to dryness.

The obtained residue and Trt-sarcocine (36 g) were dissolved in acetone (300 mL) to provide a 7th mixture. 1-Ethyl-(3-dimethylaminopropyl)carbodiimide hydrochloride (20 g) and 4-dimethylaminopyridine (12 g) were added into the 7th mixture to provide an 8th mixture. The 8th mixture was stirred overnight at RT and evaporated to dryness. Ethyl acetate (500 ml) was added into the residue to provide a 9th mixture, which was washed with water (2×100 mL), 5% sodium bucarbonate (3×100 mL), water (100 mL), 20% citric acid (2×200 mL), and water (3×100 mL), respectively, and dried over sodium sulfate to provide a 10th solution. The sodium sulfate was filtered and washed with ethyl acetate to provide an 11th solution. Pyridine (20 ml) was added into the 11th solution to provide a 12th mixture, and benzoyl chloride (15 g) was added into the 12th mixture drop by drop to provide a 13th. mixture. The 13th. mixture was stirred for 4 hours at RT and the obtained mixture was washed with water (2×100 ml), 5% sodium bucarbonate (2×100 ml), water (100 ml), 20% citric acid (2×200 ml), and water (3×100 ml), respectively, and dried over anhydrous sodium sulfate to provide a 14th solution. The sodium sulfate was removed by filtration and washed with ethyl acetate to provide a 15th solution. The 14th and the 15th solutions were combined and evaporated to dryness.

The obtained residue was dissolved in methanol (300 mL) to provide a 16th mixture. 10% Palladium on activated charcoal (10 g) was added into the 16th mixture under nitrogen, and hydrogen gas was bubbled into the obtained mixture until the benzyloxycarbonyl group was removed substantially completely at RT. The palladium on activated charcoal was removed by filtration, and the obtained solution was evaporated to dryness.

The obtained residue was suspended in DCM (200 mL). Sodium bicarbonate (15 g) and tetrabutylammonium hydrogen sulfate (11 g) were added into the DCM suspension. 1-chloroethyl chloroformate (16 g) was added into the obtained reaction mixture. Then the reaction mixture was stirred for overnight at RT. The organic layer was collected and washed with water (3×200 mL). The solution was dried over anhydrous sodium sulfate. Sodium sulfate is removed by filtration and washed with DCM. The DCM solution is evaporated to dryness.

The residue was dissolved in isobutyric acid (100 mL). A mixture of [diisopropylethylamine (60 ml) and isobutyric acid (R0874, 36 mL) which is mixed before addition] is added into the reaction solution. The mixture is stirred for 48 h at 55 C. Ethyl acetate (500 ml) is added into the reaction mixture with stirring. The organic solution is collected and washed with 5% sodium bicarbonate (3×100 ml) and water (3×100 ml). The solution is dried over anhydrous sodium sulfate. Sodium sulfate is removed by filtration and washed with ethyl acetate (3×). The solution is concentrated to 300 ml. Anisole (20 g) is added into the ethyl acetate solution. Then HCl gas (30 g) is bubbled into the ethyl acetate solution. The solid is collected and washed with ethyl acetate.

Example 22

Preparation of 4-((2S)-3-isopropoxy-2-(((((octahydroindolizin-1-yl)oxy)carbonyl)amino)-3-oxopropyl)-1,2-phenylene dibenzoate acetate

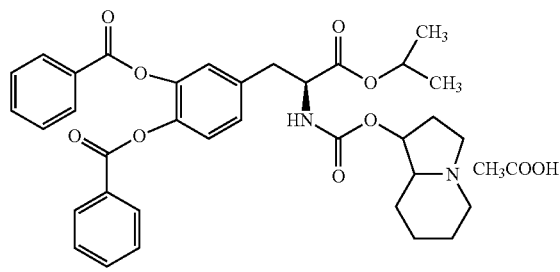

4-((2S)-3-isopropoxy-2-(((((octahydroindolizin-1-yl)oxy)carbonyl)amino)-3-oxopropyl)-1,2-phenylene dibenzoate acetate In this example, (S)-2-amino-3-(3,4-dihydroxyphenyl)propanoic acid (20 g) was added into isopropanol (200 mL). HCl gas (20 g) was bubbled into the mixture. The mixture was stirred for 2 days at 60° C. Isopropyl acetate (200 mL) was added into the mixture. The solid was collected and washed with isopropayl acetate.

Isopropyl (S)-2-amino-3-(3,4-dihydroxyphenyl)propanoate hydrochloride (28 g) was added into acetone (200 mL). Water (200 mL) and sodium bicarbonate (50 g) were added into the reaction mixture. Di-tert-butyl dicarbonate (22 g) was added into the reaction mixture. The mixture was stirred for overnight at RT. Ethyl acetate (500 mL) was added into the mixture. The mixture was washed with water (2×100 mL), 20% citric acid (2×200 mL), and water (3×100 mL). The solution was dried over sodium sulfate. Sodium sulfate was removed by filtration and washed with ethyl acetate. Pyridine (30 mL) was added into the ethyl acetate solution. Benzoyl chloride (30 g) was added into the reaction mixture drop by drop. The solution was stirred for 2 hours at RT. The solution was washed with water (2×100 mL), 5% sodium bicarbonate (2×100 mL), water (100 mL), 20% citric acid (2×200 mL), and water (3×100 mL). The solution was dried over anhydrous sodium sulfate. Sodium sulfate was removed by filtration and washed with ethyl acetate. The solution was concentrated to 200 mL. Anisole (20 g) was added into the ethyl acetate solution. Then HCl gas (20 g) was bubbled into the ethyl acetate solution. The solid was collected and washed with ethyl acetate.

The solid was suspended in ethyl acetate (200 mL), triethylamine (25 mL) was added into the mixture. Octahydroindolizin-1-yl carbonochloridate hydrochloride (22 g) in ethyl acetate (50 mL) was added into the reaction mixture drop by drop. The mixture was stirred for 2 hours at RT. The mixture was washed with 5% sodium bicarbonate and water (3×). Acetic acid (6 g) was added into the mixture. Hexanes (200 mL) was added into the mixture. The solid was collected by filtration and washed with ethyl acetate/hexanes.

Example 23

Preparation of 2-(diethylamino)ethyl 2-[(2,6-dichloro-3-methylphenyl)amino]benzoate.acetate

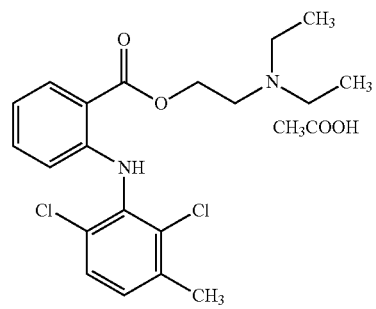

2-(diethylamino)ethyl 2-((2,6-dichloro-3-methylphenyl(amino)benzoate acetate 29.6 g (0.1 mol) of 2-[(2,6-dichloro-3-methylphenyl)amino]benzoic acid was dissolved in 300 mL of chloroform. 20.6 g of N,N'-Dicyclohexylcarbodiimide was added into the reaction mixture. 11.7 g of diethylaminoethylamine was added into the reaction mixture. The mixture was stirred for 3 hours at RT. The solid was removed by filtration. The chloroform solution was washed with 5% NaHCO$_3$ (2×100 mL) and water (3×100 mL). The organic solution was dried over anhydrous sodium sulfate. Sodium sulfate was removed by filtration. 6 g of acetic acid was added into the reaction mixture with stirring. Hexane (200 ml) was added. The solid product was collected by filtration.

Example 24

Preparation of (Z)-2-(diethylaminoethyl)ethyl 2-(5-fluoro-2-methyl-1-(4-methylsulfinyl)benzylidene)-1H-inden-1-yl)acetate.AcOH

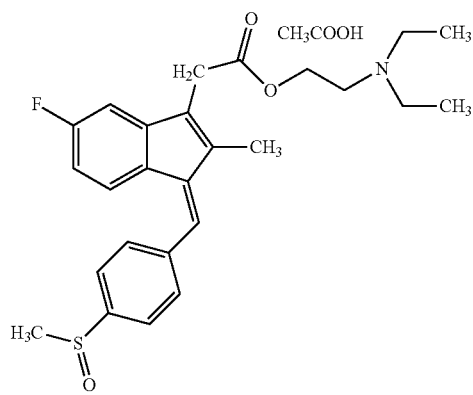

(Z)-2-(diethylamino)ethyl 2-(5-fluoro-2-methyl-1-(4-(methylsulfinyl)benzylidene)-1H-inden-3-yl)acetate acetate 11.7 g (0.1 mol) of diethylaminoethanol was dissolved in 10% sodium bicarbonate (200 mL) and acetone (100 mL). 37.5 g (0.1 mol) of (Z)-5-fluoro-2-methyl-1-[(4-methylsulfinyl)phenylmethylene]-1H-indene-3-acetyl chloride was added into the reaction mixture. The mixture was stirred for 3 hours at RT. The solvents were evaporated off. The residue was suspended in ethyl acetate (500 mL). 5% sodium bicarbonate (200 mL) was added into the reaction mixture with stirring. Ethyl acetate layer was collected and washed with water (3×500 mL). The ethyl acetate solution was dried over anhydrous sodium sulfate. Sodium sulfate was removed by filtration. 6 g of acetic acid was added into the reaction mixture with stirring. The organic solution was evaporated off.

Example 25

Preparation of 2-(dimethylamino)ethyl 2-(3-phenoxyphenyl) propionate.hydrochloride

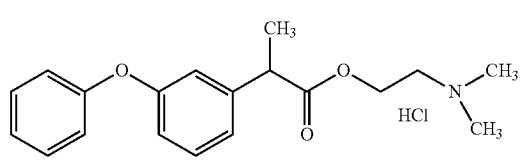

2-(dimethylamino)ethyl 2-(3-phenoxyphenyl)propionate hydrochloride 26.1 g (0.1 mol) of 2-(3-phenoxyphenyl) propionyl chloride was dissolved in 300 ml of ethyl acetate. The mixture was cooled to 0° C. 8.9 g of dimethylaminoethanol were added into the reaction mixture. Sodium bicarbonate (30 g) was added into the mixture. The mixture was stirred for 5 hours at RT. The mixture was washed with water (3×200 mL). The ethyl acetate solution was dried over anhydrous sodium sulfate. HCl gas (5 g) was bubbled into the mixture. The solid was collected by filtration and washed with ethyl acetate.

Example 26

Preparation of S-(2-(dimethylamino)ethyl 2-(3-phenoxyphenyl) propanethioate hydrochloride

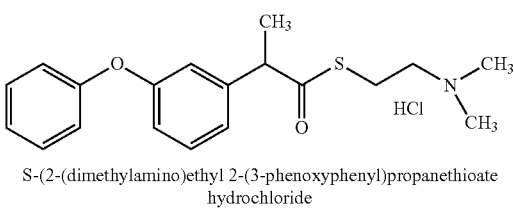 [SMILES: CC(C(=O)SCCN(C)C)c1cccc(Oc2ccccc2)c1 ; Cl]

S-(2-(dimethylamino)ethyl 2-(3-phenoxyphenyl)propanethioate hydrochloride 10.4 g (0.1 mol) of dimethylaminoethyl mercaptan was dissolved in 10% sodium bicarbonate (200 mL) and acetone (100 mL). 27.3 g (0.1 mol) of 2-(3-phenoxyphenyl) propionyl chloride was added into the reaction mixture. The mixture was stirred for 3 hours at RT. The solvents were evaporated off. The residue was suspended in ethyl acetate (500 mL). 5% sodium bicarbonate (200 mL) was added into the reaction mixture with stirring. Ethyl acetate layer was collected and washed with water (3×500 mL). The ethyl acetate solution was dried over anhydrous sodium sulfate. Sodium sulfate was removed by filtration. Anhydrous HCl gas (5 g) was bubbled into the reaction mixture with stirring. The solid was collected and washed with ethyl acetate.

Example 27

Preparation of 2-(dipropylamino)ethyl 4-acetoxy-2',4'-difluoro-[1,1'-biphenyl]-3-carboxylate hydrochloride[2-(dipropylamino)ethyl 5-(2,4-difluorophenyl) acetylsalicylate hydrochloride]

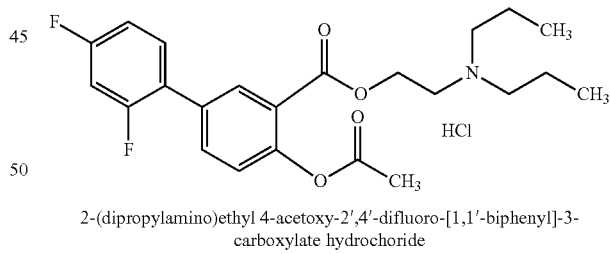

2-(dipropylamino)ethyl 4-acetoxy-2',4'-difluoro-[1,1'-biphenyl]-3-carboxylate hydrochoride 31.1 g (0.1 mol) of 5-(2,4-difluorophenyl) acetylsalicyl chloride was dissolved in 300 mL of ethyl acetate. The mixture was cooled to 0° C. 11.7 g (0.1 mol) of diethylaminoethanol were added into the reaction mixture. The sodium bicarbonate (30 g) was added into the reaction mixture. The mixture was stirred for 3 hours at RT. Then water (200 mL) was added into the mixture. The ethyl acetate layer was collected and washed with water (3×). The solution was dried over anhydrous sodium sulfate. Anhydrous HCl gas was bubbled into the reaction mixture with stirring. The solid was collected and washed with ethyl acetate.

Example 28

Preparation of 2-(diethylamino)ethyl 2-(4-isobutylphenyl)propionate hydrochloride

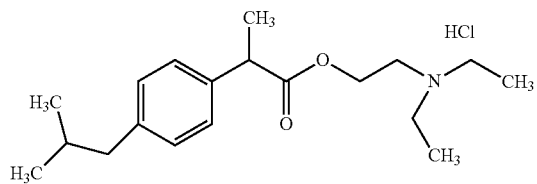

2-(diethylamino)ethyl 2-(4-isobutylpheny)propionate hydrochloride 41 g of ibuprofen was dissolved in 200 ml of ethyl acetate. 16 mL of thionyl chloride was added into the mixture. The mixture was refluxed for 2 h. The mixture was evaporated to dryness completely. 500 mL of ethyl acetate was added into the residue and evaporated off. 500 mL of ethyl acetate was added into the reaction mixture. The solution was cooled to 5° C. with ice-water bath. 23 g of N,N-diethylaminoethanol was added into the reaction mixture drop by drop. 40 g of $Na_2CO_3$ was added into the reaction mixture slowly. The mixture was stirred for overnight at RT. 200 mL of water was added into the mixture. The ethyl acetate solution was collected and washed with water (3×200 mL) and dried over anhydrous $Na_2SO_4$. Sodium sulfate was removed by filtration and washed with ethyl acetate (3×100 mL). Anhydrous HCl gas (10 g) was bubbled into the mixture. The solid was collected and washed with ethyl acetate.

Example 29

Preparation of 2-(diethylamino)ethyl 2-acetoxybenzoate hydrochloride (2-(diethylamino)ethyl acetylsalicylate hydrochloride)

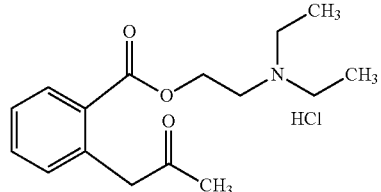

2-(diethylamino)ethyl 2-acetoxybenzoate hydrochloride 36 g of aspirin was dissolved in 100 mL of ethyl acetate. 16 mL of thionyl chloride was added into the mixture. The mixture was refluxed for 3 h. The mixture was evaporated to dryness completely. 100 mL of ethyl acetate was added into the residue and evaporated off. 500 mL of ethyl acetate was added into the reaction mixture. The solution was cooled to 5° C. with ice-water bath. 23 g of N-diethylaminoethanol was added into the reaction mixture drop by drop. 40 g of $NaHCO_3$ was added into the reaction mixture slowly. The mixture was stirred for overnight at RT. 200 mL of water was added into the mixture. The ethyl acetate solution was collected and washed with water (3×100 mL) and dried over anhydrous $Na_2SO_4$. Sodium sulfate was removed by filtration and washed with ethyl acetate (3×100 mL). Anhydrous HCl gas (10 g) was bubbled into the mixture. The solid was collected and washed with ethyl acetate.

Example 30

Measurements of Penetration Rates of HPPs

The penetrate rates of 4-(2-(2-(methylamino)acetamido)ethyl)-1,2,-phenylene dibenzoate hydrochloride (Compound-1), 4-(2-(2-(methylamino)acetamido)ethyl)-1,2,-phenylene dibenzoate acetic acid (Compound-2), 4-(6-methyl-4,8-dioxo-5,7-dioxa-2,9-diazadecan-11-yl)-1,2,-phenylene dibenzoate hydrobromide (Compound-3), 4-(2-(2-amino-3-phenylpropanamido)ethyl)-1,2,-phenylene dibenzoate hydrochloride (Compound-4), 4-(2-(((1-((pyrrolidine-2-carbonyl)oxy)ethoxy)amino)ethyl)-1,2,-phenylene dibenzoate hydrochloride (Compound-5), 4-(2-piperidine-4-carboxamido)ethyl)-1,2,-phenylene bis(2-ethylbutanoate) hydrochloride (Compound-6), 4-(2-((((-octahydro-1H-quinolizin-3-yl)oxy)carbonyl)amino)ethyl)-1,2,-phenylene bis(2-ethylbutanoate)acetate (Compound-7), 1-(((2-(4-amino-2,5-dioxo-2,3,4,5-tetrahydrobenzo[b][1,4]dioxocin-8-yl)ethyl)carbamoyl)oxy)ethyl isobutyrate hydrofluoride (Compound-8a), 1-(((2-(3-amino-2,5-dioxo-2,3,4,5-tetrahydrobenzo[b][1,4]dioxocin-8-yl)ethyl)carbamoyl)oxy)ethyl isobutyrate hydrofluoride (Compound-8b), (5-(2-((ethoxycarbonyl)amino)ethyl)-2-(2-methylamino)acetoxy)phenyl benzoate hydrochloride (Compound-9a), 5-(2-((ethoxycarbonyl)amino)ethyl)-2-(2-methylamino)acetoxy)phenyl benzoate hydrochloride (Compound-9b), 4-(2-aminoethyl)-1,2-phenylene dibenzoate hydrochloride (Compound-10), (S)-4-(2-amino-3-isopropoxy-3-oxopropyl)-1,2-phenylene dibenzoate hydrochloride (Compound-11), (S)-4-(2-amino-3-(heptan-4-yloxy)-3-oxopropyl)-1,2-phenylene dibenzoate hydrochloride (Compound-12), (S)-4-(2-amino-3-isopropoxy-3-oxopropyl)-1,2-phenylene dipentanoate hydrochloride (Compound-13), (S)-4-(2-amino-3-ethoxy-3-oxopropyl)-1,2-phenylene diacetate hydrochloride (Compound-14), (S)-4-(2-amino-3-oxo-3-(pentan-3-yloxy)propyl)-1,2-phenylene bis(2-methylpropanoate) hydrobromide (Compound-15), (S)-4-(2-aminoacetamido)-3-isopropoxy-3-oxopropyl)-1,2-phenylene dibenzoate hydrochloride (Compound-16), 4-((2S)-3-oxo-3-(pentan-3-yloxy)-2-(pyrrolidine-2-carboxamido)propyl)-1,2-phenylene dibenzoate hydrofluoride (Compound-17), (S)-4-(3-isopropoxy-3-oxo-2-(piperidine-4-carboxamido)propyl)-1,2-phenylene dibenzoate hydrochloride (Compound-18), 4-((2S)-3-isopropoxy-3-2-(octahydro-1H-quinolizine-2-carboxamido)-3-oxopropyl)-1,2-phenylene bis(2-methylpropanoate) hydrochloride (Compound-19), (2S)-isopropyl 3-(3-amino-2,5-dioxo-2,3,4,5-tetrahydrobenzo[b][1,4]dioxocin-8-yl)-2-(((1-(isobutyryloxy)ethoxy)carbonyl)amino)propanoate hydrobromide (Compound-20a), (2S)-isopropyl 3-(4-amino-2,5-dioxo-2,3,4,5-tetrahydrobenzo[b][1,4]dioxocin-8-yl)-2-(((1-(isobutyryloxy)ethoxy)carbonyl)amino)propanoate hydrobromide (Compound-20b), 5-((2S)-2-(((1-(isobutyryloxy)ethoxy)carbonyl)amino-3-isopropoxy-3-oxopropyl)-2-(2-(methylamino)acetoxy)phenyl benzoate hydrochloride (Compound-21a), 4-((2S)-2-(((1-(isobutyryloxy)ethoxy)carbonyl)amino-3-isopropoxy-3-oxopropyl)-2-(2-(methylamino)acetoxy)phenyl benzoate hydrochloride (Compound-21b), 4-((2S)-3-isopropoxy-2-((((octahydroindolizin-1-yl)oxy)carbonyl)amino)-3-oxopropyl)-1,2-phenylene dibenzoate acetate (Compound-22), 2-(diethylamino)ethyl 2-[(2,6-dichloro-3-methylphenyl)amino]benzoate.acetate (Compound-23), (Z)-2-(diethylaminoethyl)ethyl 2-(5-fluoro-2-methyl-1-(4- methylsulfinyl)benzylidene)-1H-inden-1-yl)acetate.AcOH (Compound-24), 2-(dimethylamino)ethyl 2-(3-phenoxyphenyl) propionate.hydrochloride (Compound-25), S-(2-(dimethylamino)ethyl 2-(3-phenoxyphenyl) propanethioate hydrochloride (Compound-26), 2-(dipropylamino)ethyl 4-acetoxy-2',4'-difluoro-[1,1'-biphenyl]-3-carboxylate hydrochloride (Compound-27), 2-(diethylamino)ethyl 2-(4-isobutylphenyl)propionate hydrochloride (Compound-28), 2-(diethylamino)ethyl 2-acetoxybenzoate hydrochloride (Compound-29), 4-(2-aminoethyl)benzene-1,2-diol hydrochloride (Compound 30), 2-amino-3-(3,4-dihydroxyphenyl) propanoic acid (L-Dopa, Compound 31), acetylsalicylic acid (Compound 32), 2-(ρ-isobutylphenyl)propionic acid (ibuprofen, Compound 33), and 2-(3-phenoxyphenyl) propionic acid (Compound 34) through human skin were measured in vitro by using modified Franz cells, which were isolated from human skin tissue (360-400 μm thick) of the anterior and posterior thigh areas. The receiving fluid consisted of 10 mL of pH 7.4 phosphate buffer (0.2 M) are shown in Table 1. The results suggested that the positive charge on the amino group has a very important role in the passage of the drug across the membrane and skin barrier.

TABLE 1

The Cumulative amounts of Pro-drugs of dopamine, L-Dopa, and NSAIDs in a period of 8 hours.

| | The cumulative amount of test compounds | | | |
|---|---|---|---|---|
| | 1 h | 2 h | 4 h | 8 h |
| Compound-1 | 0.67 mg | 1.33 mg | 2.67 mg | 5.25 mg |
| Compound-2 | 0.65 mg | 1.29 mg | 2.63 mg | 5.23 mg |
| Compound-3 | 0.61 mg | 1.23 mg | 2.49 mg | 5.01 mg |
| Compound-4 | 0.59 mg | 1.21 mg | 2.45 mg | 4.93 mg |
| Compound-5 | 0.60 mg | 1.19 mg | 2.37 mg | 4.79 mg |
| Compound-6 | 0.63 mg | 1.25 mg | 2.53 mg | 5.03 mg |
| Compound-7 | 0.64 mg | 1.27 mg | 2.57 mg | 5.05 mg |
| Compound-8a | 0.63 mg | 1.22 mg | 2.43 mg | 4.83 mg |
| Compound-8b | 0.62 mg | 1.24 mg | 2.47 mg | 4.85 mg |
| Compound-9a | 0.61 mg | 1.23 mg | 2.45 mg | 4.87 mg |
| Compound-9b | 0.62 mg | 1.26 mg | 2.48 mg | 4.95 mg |
| Compound-10 | 0.68 mg | 1.35 mg | 2.74 mg | 5.55 mg |
| Compound-11 | 0.58 mg | 1.15 mg | 2.33 mg | 4.71 mg |
| Compound-12 | 0.53 mg | 1.07 mg | 2.13 mg | 4.29 mg |
| Compound-13 | 0.52 mg | 1.05 mg | 2.10 mg | 4.23 mg |
| Compound-14 | 0.60 mg | 1.21 mg | 2.44 mg | 4.82 mg |
| Compound-15 | 0.55 mg | 1.08 mg | 2.23 mg | 4.41 mg |
| Compound-16 | 0.56 mg | 1.13 mg | 2.23 mg | 4.49 mg |
| Compound-17 | 0.58 mg | 1.15 mg | 2.33 mg | 4.71 mg |
| Compound-18 | 0.52 mg | 1.03 mg | 2.10 mg | 4.19 mg |
| Compound-19 | 0.48 mg | 0.98 mg | 2.02 mg | 4.09 mg |
| Compound-20(a) | 0.42 mg | 0.88 mg | 1.75 mg | 3.49 mg |
| Compound-20(b) | 0.43 mg | 0.85 mg | 1.78 mg | 3.52 mg |
| Compound-21(a) | 0.52 mg | 1.08 mg | 2.17 mg | 4.37 mg |
| Compound-21(b) | 0.51 mg | 1.05 mg | 2.08 mg | 4.19 mg |
| Compound-22 | 0.45 mg | 0.89 mg | 1.78 mg | 3.61 mg |
| Compound-23 | 0.85 mg | 1.69 mg | 3.38 mg | 6.85 mg |
| Compound-24 | 0.87 mg | 1.79 mg | 3.53 mg | 7.15 mg |
| Compound-25 | 1.15 mg | 2.31 mg | 4.58 mg | 9.22 mg |
| Compound-26 | 1.17 mg | 2.33 mg | 4.65 mg | 9.31 mg |
| Compound-27 | 1.01 mg | 2.03 mg | 4.11 mg | 8.25 mg |
| Compound-28 | 1.15 mg | 2.28 mg | 4.57 mg | 9.19 mg |
| Compound-29 | 1.08 mg | 2.13 mg | 4.27 mg | 8.48 mg |
| Compound-30 | 0.12 mg | 0.25 mg | 0.52 mg | 1.05 mg |
| Compound-31 | 0.001 mg | 0.001 mg | 0.002 mg | 0.003 mg |
| Compound-32 | 0.001 mg | 0.001 mg | 0.002 mg | 0.003 mg |
| Compound-33 | 0.001 mg | 0.001 mg | 0.002 mg | 0.003 mg |
| Compound-34 | 0.001 mg | 0.001 mg | 0.002 mg | 0.003 mg |

Example 31

The Efficacy of (S)-4-(2-amino-3-isopropoxy-3-oxopropyl)-1,2-phenylene dibenzoate hydrochloride (Drug A) and 2-(diethylamino)ethyl 2-acetoxybenzoate hydrochloride (Drug B), on Improvement of Motor Function Deficits and Reduction of Nigro-Striatal Neurodegeneration Induced by 6-OHDA in Parkinson's Disease (PD) Model at HDB Test subjects (Sprague-Dawley rats) were prepared, grouped, and tested following the protocol below:
1. 200 Sprague-Dawley rats (male, 200-230 g) underwent brain stereotaxic surgery after 1 week acclamation in animal facility;
2. After anesthesia, a bur hole (1 mm in diameter) was made on skull on the left side with a motor drill based on the coordinates: AP+0.5 mm, ML −2.8 mm, DV 6.0 mm relative to Bregma;
3. 6-OHDA (20 μg at 5 mg/mL) or sterile saline was injected into the left striatum with a microsyringe fitted with a 26-gauge steel cannula. The chemical caused the retrograde neurodegeneration in the distal substantia nigra and impairs dopamine transmission in the nigro-striatal pathway, which eventually led to functional disturbance of motor activities;
4. Apomorphine and classic rotation test was carried out to screen animals at the end of week 3 post 6-OHDA treatment. Animals that matched lesion type and apomorphine-induced rotational scores were allotted to 11 groups; and
5. Rats were divided into 11 groups (n=12), each group was applied with the drug(s) at the doses specified in Table 2:

TABLE 2

Doses and Drug(s) Applied to the Test Animals

| Group No. | Group Name | Drug(s) Applied | Parent drug | Dosage (mg/kg) | Administration Method |
|---|---|---|---|---|---|
| 1 | Positive Control | L-DOPA | N/A | 6 | Oral |
| 2 | Negative Control/ Vehicle | 30% ethanol(v/v) (Vehicle) | N/A | 1286 (μL/kg) | Transdermal |
| 3 | Low dose | Drug A | L-DOPA | 0.67 | Transdermal |
| 4 | Moderate dose | | | 2 | Transdermal |
| 5 | High dose | | | 6 | Transdermal |
| 6 | N/A | Drug A | L-DOPA | 0.67 | Transdermal |
| | | Drug B | Aspirin | 30 | Transdermal |
| 7 | N/A | Drug A | L-DOPA | 2 | Transdermal |
| | | Drug B | Aspirin | 30 | Transdermal |
| 8 | N/A | Drug B | Aspirin | 30 | Transdermal |
| 9 | N/A | Drug A | L-DOPA | 0.67 | Transdermal |
| | | Drug B | Aspirin | 90 | Transdermal |
| 10 | N/A | Drug A | L-DOPA | 2 | Transdermal |
| | | Drug B | Aspirin | 90 | Transdermal |
| 11 | N/A | Drug B | Aspirin | 90 | Transdermal |

Figure 2:
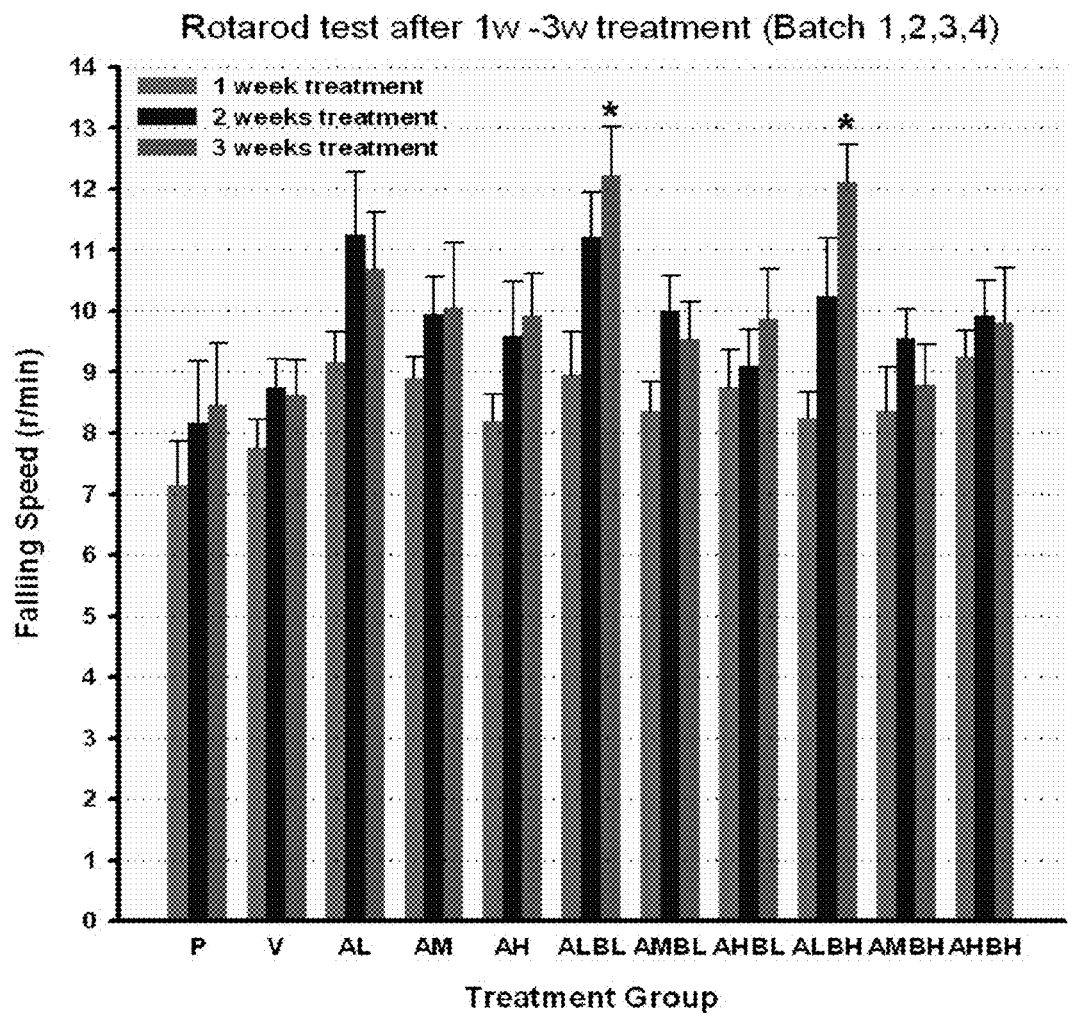
FIG. 2. The falling speed results in Totarod test after 1-3 week treatment (n=12) (Example 31).

6. Dose Formulations
   (1) L-DOPA in water (3 mg/mL) was the positive control solution for group 1 (orally for group 1, transdermally for groups 2-11). The volume of administration was 2 mL/kg. Vehicle solution (negative control solution for group 2) was 30% ethanol (v/v). The volume of administration was 1286 μL/kg. Other test solutions (groups 3-11) were freshly prepared every day.
   (2) Preparation method of test solutions for groups 3-5: 50.33 mg of Drug A was dissolved in 10 mL of 30% ethanol (v/v). This solution was the stock solution [(2)a].

a. The test solution for group 5 (high dose group) of Drug A: The stock solution [(2)a] was the test solution for Group 5. The volume of administration was 1286 µL/kg.
b. The test solution for group 4 (moderate dose group) of Drug A: 3.00 mL of the stock solution [(2)a] was diluted to final volume 9.00 mL with 30% ethanol (v/v). This solution was the test solution for Group 4. The volume of administration was 1286 µL/kg.
c. The test solution for group 3 (low dose group) of Drug A: 1.00 mL of the stock solution [(2)a]) was diluted to final volume 9.00 mL with 30% ethanol (v/v). This solution was the test solution for Group 4. The volume of administration was 1286 µL/kg.
(3) Preparation method of test solutions for group 6: 5.67 mg of Drug A and 264 mg of Drug B were dissolved in 10 mL of 30% ethanol (v/v). This solution was the test solution for groups 6.
(4) Preparation method of test solutions for groups 7: 16.67 mg of Drug A and 264 mg of Drug B were dissolved in 10 mL of 30% ethanol (v/v). This solution was the test solution for groups 7.
(5) Preparation method of test solutions for groups 8: 264 mg of Drug B was dissolved in 10 mL of 30% ethanol (v/v). This solution was the test solution for groups 8.
(6) Preparation method of test solutions for group 9: 5.67 mg of Drug A and 791 mg of Drug B were dissolved in 10 mL of 30% ethanol (v/v). This solution was the test solution for groups 9.
(7) Preparation method of test solutions for groups 10: 16.67 mg of Drug A and 791 mg of Drug B were dissolved in 10 mL of 30% ethanol (v/v). This solution was the test solution for groups 10.
(8) Preparation method of test solutions for groups 11: 791 mg of Drug A was dissolved in 10 mL of 30% ethanol (v/v). This solution was the test solution for groups 11.
7. On the day prior to the scheduled dosing, the hair (all rat including the positive control group rats with L-DOPA due to the double-blinded fashion) was removed from the up back (around the neck and shoulder) of the animal using a small animal clipper. The animals were re-clipped as necessary throughout the course of the study to keep the epidermis exposed. On the day of dosing, an aliquot (643 µL/kg) of the dosing formulation was administered to a 3 cm by 3 cm square section of the animal (around the neck and shoulder) at around 9 am and repeat it at around 4 µm.
8. At week 4 post lesion, the groups started to receive treatment.
9. Rotarod tests were performed every week after treatment.
FIG. 1 showed the staying time results in the Totarod test described above after 1-3 week treatment (n=12). FIG. 2 showed the falling speed results in Totarod test described above after 1-3 week treatment (n=12).

The improvement of performance in PD animals were supposed to stay longer on the road and endure a higher speed of the rotating (if no side effect of the test drug(s) was involved).

By pooling all batches data together (12 animals/group), the positive group (Group 1, L-DOPA, 6 mg/kg, orally) did not exhibit efficacy comparing to Vehicle group after three-week treatment. However, all test drug treatment groups (Groups 2~11) exhibited stronger efficacy comparing to Vehicle group after three-week treatment. Levodopa contributed to the development of motor complications in PD. Levodopa caused nausea, vomiting, gastrointestinal bleeding, dyskinesia at peak dose, and end-of-dose deterioration of function, so the positive group (Group 1, L-DOPA, 6 mg/kg, orally) did not exhibit efficacy comparing to Vehicle group. However, the transdermally administrated pro-drug of L-Dopa (Drug A) avoided dyskinesia at peak dose, and end-of-dose deterioration of function. The efficacy of the low dose of Drug A (a pro-drug of L-Dopa, 0.67 mg/kg, group 3) was much higher than that of the moderate and high dose groups of Drug A (2 mg and 6 mg/kg, groups 4 and 5). Such result showed that the dose of transdermal administrated pro-drug of L-dopa was much less than that of the oral administrated L-dopa (9 times less). 30 mg and 90 mg/kg of Drug B (a pro-drug of aspirin) exhibited good efficacy comparing to vehicle group and positive control group after three-week treatment. 30 mg of Drug B (group 8) exhibited similar efficacy as 90 mg of Drug B (group 11). This result showed that 30 mg/kg dose might have been sufficient for Drug B and higher dose was not necessary. Applying a combination of Drug A and Drug B (group 6 and group 9) to the subjects worked much better than applying either Drug B (groups 8 and 11) or Drug A (group 3) alone.

When applying a combination of a plurality of drugs (e.g. one or more HPPs and/or other drug(s)) to a subject, each drug could be applied separately, or one or more of the drugs could be applied at substantially the same time as separate drugs (e.g. spraying two or more drugs at substantially the same time without mixing the drugs before spraying), or one or more drugs could be mixed together before applying to the subject, or any combination of the above application methods. The drugs could be applied in any order possible.

Example 32

The Efficacy of Drug A (Transdermally), Drug B (Transdermally), and Carbidopa Orally on Improvement of Motor Function Deficits and Reduction of Nigro-Striatal Neurodegeneration Induced by 6-OHDA in Parkinson's Disease (PD) Model at HDB Test subjects (Sprague-Dawley rats) were prepared as described in Example 31, and grouped and tested following the protocol below:
1. Rats were divided into 11 groups (n=12), each group was applied with the drug(s) at the doses specified in Table 3:

TABLE 3

Doses and Drug(s) Applied to the Test Animals

| Group No. | Group Name | Drug(s) Applied | Parent drug | Dosage (mg/kg) | Administration Method |
|---|---|---|---|---|---|
| 1 | Positive Control | L-DOPA | N/A | 6 | Oral |
|   |   | Carbidopa | N/A | 1.5 | Oral |
| 2 | Negative Control | 30% ethanol(v/v) (Vehicle) | N/A | 1,286 (µL/kg) | Transdermal |
|   |   | Carbidopa | N/A | 1.5 | Oral |
| 3 | Low dose | Drug A | L-DOPA | 0.67 | Transdermal |
|   |   | Carbidopa | N/A | 1.5 | Oral |
| 4 | Moderate dose | Drug A | L-DOPA | 2 | Transdermal |
|   |   | Carbidopa | N/A | 1.5 | Oral |
| 5 | High dose | Drug A | L-DOPA | 6 | Transdermal |
|   |   | Carbidopa | N/A | 1.5 | Oral |
| 6 |   | Drug A | L-DOPA | 0.67 | Transdermal |
|   |   | Drug B | Aspirin | 30 | Transdermal |
|   |   | Carbidopa | N/A | 1.5 | Oral |
| 7 |   | Drug A | L-DOPA | 2 | Transdermal |
|   |   | Drug B | Aspirin | 30 | Transdermal |
|   |   | Carbidopa | N/A | 1.5 | Oral |

TABLE 3-continued

Doses and Drug(s) Applied to the Test Animals

| Group No. | Group Name | Drug(s) Applied | Parent drug | Dosage (mg/kg) | Administration Method |
|---|---|---|---|---|---|
| 8 | | Drug B | Aspirin | 30 | Transdermal |
| | | Carbidopa | N/A | 1.5 | Oral |
| 9 | | Drug A | L-DOPA | 0.67 | Transdermal |
| | | Drug B | Aspirin | 90 | Transdermal |
| | | Carbidopa | N/A | 1.5 | Oral |
| 10 | | Drug A | L-DOPA | 2 | Transdermal |
| | | Drug B | Aspirin | 90 | Transdermal |
| | | Carbidopa | N/A | 1.5 | Oral |
| 11 | | Drug B | Aspirin | 90 | Transdermal |
| | | Carbidopa | N/A | 1.5 | Oral |

2. Dose Formulations (1) Both L-DOPA (3 mg/ml) and carbidopa (1.5 mg/mL) in water were used as the positive control solution for group 1 (orally), the volume of administration was 2 mL/kg. Carbidopa in water (3 mg/mL) was as an aromatic-L-amino-acid decarboxylase inhibitor for groups 2-11 (orally), the volume of administration was 2 mL/kg. Vehicle solution (negative control solution for group 2) was 30% ethanol (v/v), the volume of administration was 1,286 μL/kg. Other test solutions (transdermally, groups 3-11) were freshly prepared every day.

(2) Preparation method of test solutions for groups 3-5: 50.33 mg of Drug A was dissolved in 10 mL of 30% ethanol (v/v). This solution was the stock solution (2).

(a) The stock solution (2) was the test solution for Group 5 (high dose group) of Drug A. The volume of administration was 1,286 μL/kg;

(b) The test solution for group 4 (moderate dose group) of Drug A: 3.00 mL of the stock solution (2) was diluted to final volume 9.00 mL with 30% ethanol (v/v). This solution was the test solution for Group 4. The volume of administration was 1,286 μL/kg;

(c) The test solution for group 3 (low dose group) of Drug A: 1.00 mL of the stock solution (2) was diluted to final volume 9.00 mL with 30% ethanol (v/v). This solution was the test solution for Group 3. The volume of administration was 1,286 μL/kg.

(3) Preparation method of test solutions for group 6: 5.67 mg of Drug A and 264 mg of Drug B were dissolved in 10 mL of 30% ethanol (v/v). This solution was the test solution for groups 6;

(4) Preparation method of test solutions for group 7: 16.67 mg of Drug A and 264 mg of Drug B were dissolved in 10 mL of 30% ethanol (v/v). This solution was the test solution for groups 7;

(5) Preparation method of test solutions for groups 8: 264 mg of Drug B was dissolved in 10 mL of 30% ethanol (v/v). This solution was the test solution for groups 8;

(6) Preparation method of test solutions for group 9: 5.67 mg of Drug A and 791 mg of Drug B were dissolved in 10 mL of 30% ethanol (v/v). This solution was the test solution for groups 9;

(7) Preparation method of test solutions for groups 10: 16.67 mg of Drug A and 791 mg of Drug B were dissolved in 10 mL of 30% ethanol (v/v). This solution was the test solution for groups 10;

(8) Preparation method of test solutions for groups 11: 791 mg of Drug B was dissolved in 10 mL of 30% ethanol (v/v). This solution was the test solution for groups 11.

3. On the day prior to the scheduled dosing, the hair (all rat including the positive control group rats with L-DOPA due to the double-blinded fashion) was removed from the up back (around the neck and shoulder) of the animal using a small animal clipper. The animals were re-clipped as necessary throughout the course of the study to keep the epidermis exposed. On the day of dosing, an aliquot (643 μL/kg) of the dosing formulation was administered to a 3 cm by 3 cm square section of the animal (around the neck and shoulder) at around 9 am and repeat it at around 4 μm.

4. At week 4 post lesion, the groups started to receive treatment.

5. Rotarod test were performed 4 weeks after treatment.

Figure 3:
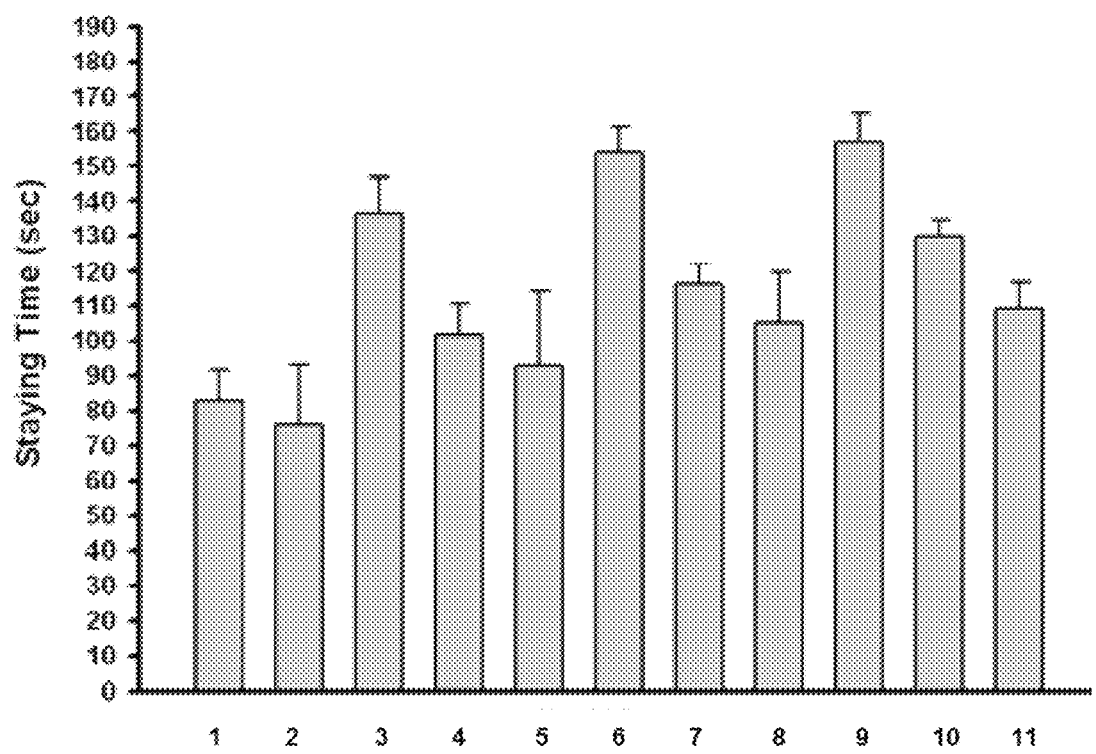
FIG. 3. The staying time results in Totarod test after 4 weeks treatment (n=12) (Example 32).
Figure 4:
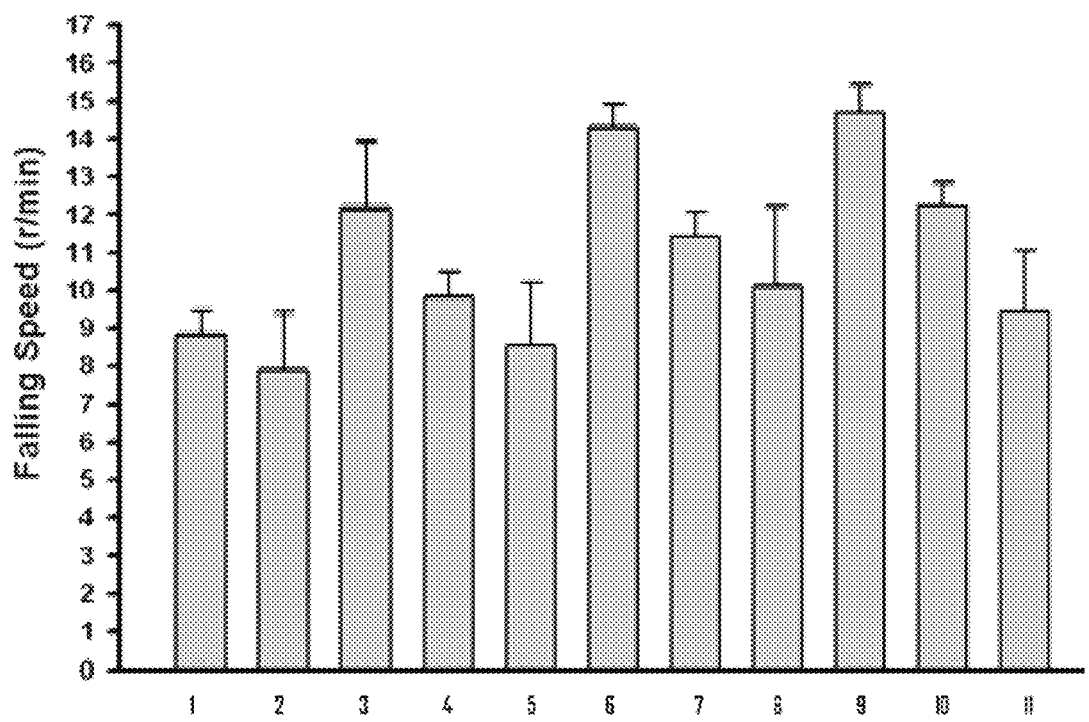
FIG. 4. The falling speed results in Totarod test after 4 weeks treatment (n=12) (Example 32).

FIG. 3 showed the staying time results in Totarod test described above after 4 weeks treatment (n=12). FIG. 4 showed the falling speed results in Totarod test described above after 4 weeks treatment (n=12).

Carbidopa can decrease peripheral DDC conversion of levodopa before it crosses the blood-brain barrier, then reduced the side effects of L-Dopa. The results show that carbidopa increased efficacy of all L-Dopa and the pro-drug of L-Dopa (Drug A) treated groups (groups 1, 3, 4, 5, 6, 7, 9, 10), but did not change the efficacy of vehicle group and pro-drug of aspirin treated groups (Drug B) (groups 2, 8 and 11).

When applying a combination of a plurality of drugs (e.g. one or more HPPs and/or other drug(s)) to a subject, each drug could be applied separately, or one or more of the drugs could be applied at substantially the same time as separate drugs (e.g. spraying two or more drugs at substantially the same time without mixing the drugs before spraying), or one or more drugs could be mixed together before applying to the subject, or any combination of the above application methods. The drugs could be applied in any order possible.

Example 33

The Efficacy of Pro-Drugs of L-Dopa and Ibuprofen on Improvement of Motor Function Deficits and Reduction of Nigro-Striatal Neurodegeneration Induced by 6-OHDA in Parkinson's Disease (PD) Model at HDB Test subjects (Sprague-Dawley rats) were prepared as described in Example 31, and grouped and tested following the protocol below:

1. Rats were divided into 11 groups (n=12), each group was applied with the drug(s) at the doses specified in Table 4, Drug C was (S)-4-(2-amino-3-oxo-3-(pentan-3-yloxy)propyl)-1,2-phenylene bis(2-methylpropanoate) hydrobromide, and Drug D was 2-(diethylamino)ethyl 2-(4-isobutylphenyl)propionate acetic acid salt:

TABLE 4

Doses and Drug(s) Applied to the Test Animals

| Group No. | Group Name | Drug(s) Applied | Parent drug | Dosage (mg/kg) | Administration Method |
|---|---|---|---|---|---|
| 1 | Positive Control | L-DOPA | N/A | 6 | Oral |
| 2 | Negative Control | 30% ethanol(v/v) (Vehicle) | N/A | 1286 (μL/kg) | Transdermal |
| 3 | Low dose | Drug C | L-DOPA | 0.67 | Transdermal |
| 4 | Moderate | | | 2 | Transdermal |

TABLE 4-continued

Doses and Drug(s) Applied to the Test Animals

| Group No. | Group Name | Drug(s) Applied | Parent drug | Dosage (mg/kg) | Administration Method |
|---|---|---|---|---|---|
| | dose | | | | |
| 5 | High dose | | | 6 | Transdermal |
| 6 | | Drug C | L-DOPA | 0.67 | Transdermal |
| | | Drug D | Ibuprofen | 15 | Transdermal |
| 7 | | Drug C | L-DOPA | 2 | Transdermal |
| | | Drug D | Ibuprofen | 15 | Transdermal |
| 8 | | Drug D | Ibuprofen | 15 | Transdermal |
| 9 | | Drug C | L-DOPA | 0.67 | Transdermal |
| | | Drug D | Ibuprofen | 45 | Transdermal |
| 10 | | Drug C | L-DOPA | 2 | Transdermal |
| | | Drug D | Ibuprofen | 45 | Transdermal |
| 11 | | Drug D | Ibuprofen | 45 | Transdermal |

Figure 5:
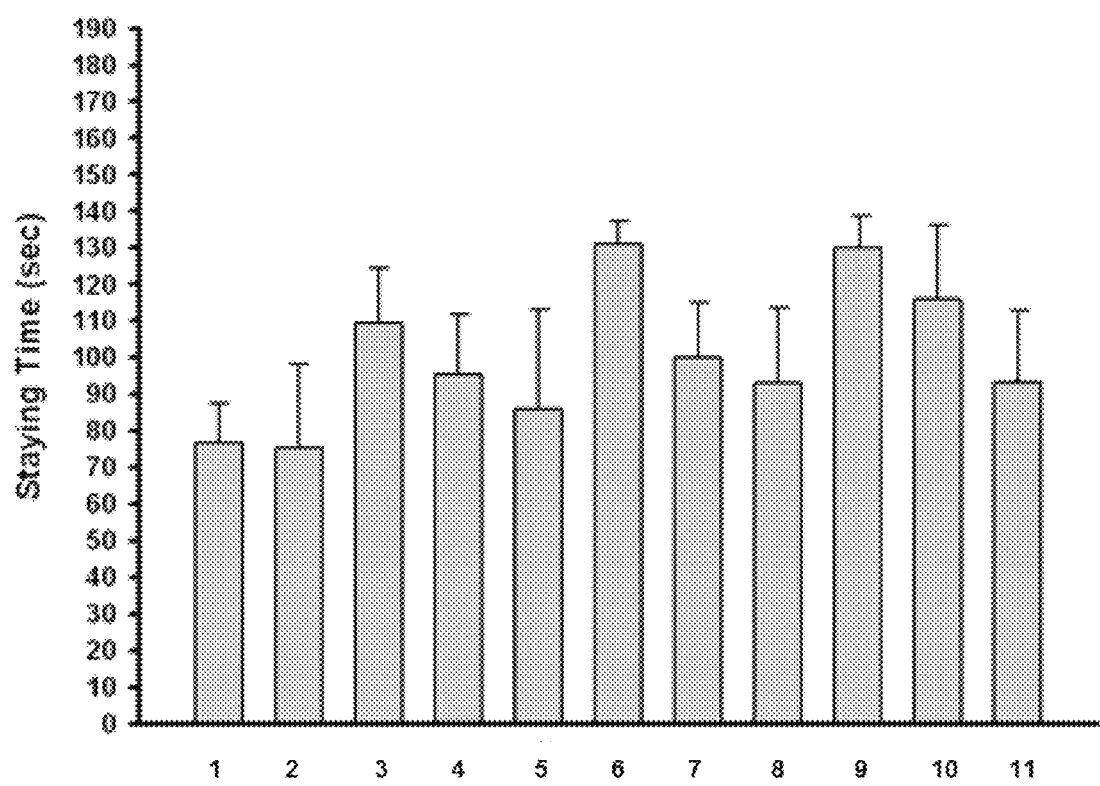
FIG. 5. The staying time results in Totarod test after 4 weeks treatment (n=12) (Example 33).
Figure 6:
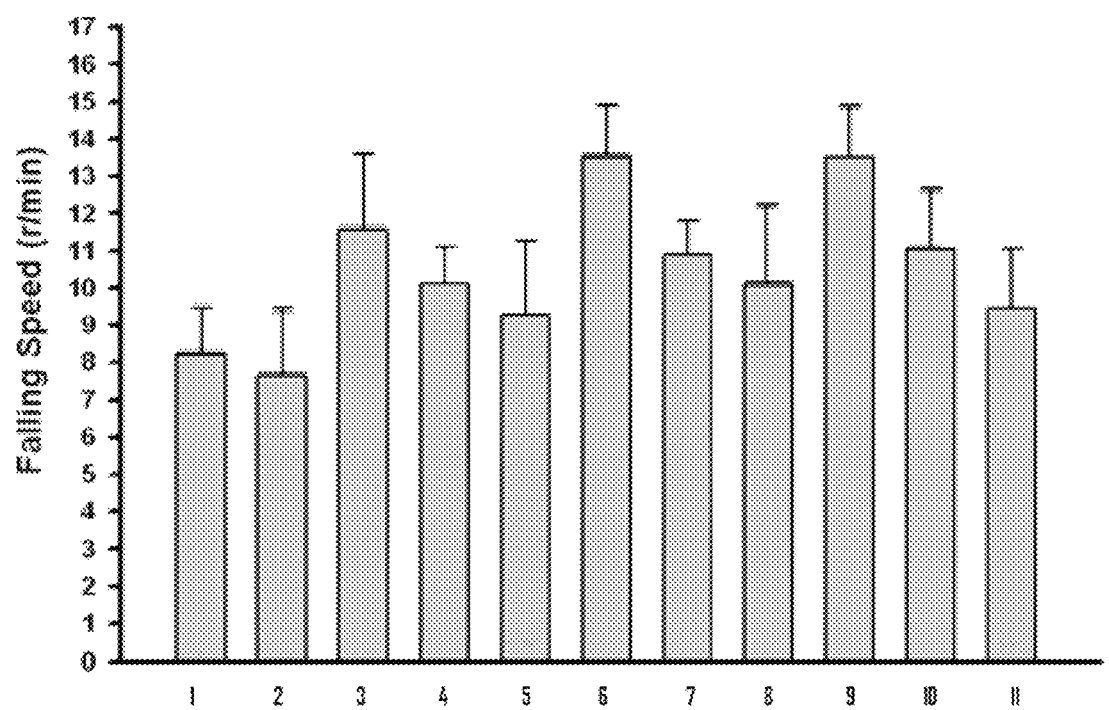
FIG. 6. The falling speed results in Totarod test after 4 weeks treatment (n=12) (Example 33).

2. Dose Formulations
(1) L-DOPA in water (3 mg/mL) was the positive control solution for group 1 (orally), the volume of administration was 2 mL/kg. Vehicle solution (negative control solution for group 2) was 30% ethanol (v/v), the volume of administration was 1286 µL/kg. Other test solutions (groups 3-11) were freshly prepared every day.
(2) Preparation method of test solutions for groups 3-5: 50.33 mg of Drug C was dissolved in 10 mL of 30% ethanol (v/v). This solution was the stock solution (2).
  a) The test solution for group 5 (high dose group) of Drug C: The stock solution (2) was the test solution for group 5. The volume of administration was 1,286 µL/kg;
  b) The test solution for group 4 (moderate dose group) of Drug C: 3.00 mL of the stock solution (2) was diluted to final volume 9.00 mL with 30% ethanol (v/v). This solution was the test solution for group 4. The volume of administration was 1,286 µL/kg;
  c) The test solution for group 3 (low dose group) of Drug C: 1.00 mL of the stock solution (2) was diluted to final volume 9.00 mL with 30% ethanol (v/v). This solution was the test solution for group 3. The volume of administration was 1,286 µL/kg.
(3) Preparation method of test solutions for group 6: 5.67 mg of Drug C and 132 mg of Drug D were dissolved in 10 mL of 30% ethanol (v/v). This solution was the test solution for group 6.
(4) Preparation method of test solutions for groups 7: 16.67 mg of Drug C and 132 mg of Drug D were dissolved in 10 mL of 30% ethanol (v/v). This solution was the test solution for group 7.
(5) Preparation method of test solutions for groups 8: 132 mg of Drug D was dissolved in 10 mL of 30% ethanol (v/v). This solution was the test solution for group 8.
(6) Preparation method of test solutions for group 9: 5.67 mg of Drug C and 395.5 mg of Drug D were dissolved in 10 mL of 30% ethanol (v/v). This solution was the test solution for group 9.
(7) Preparation method of test solutions for groups 10: 16.67 mg of Drug C and 395.5 mg of Drug D were dissolved in 10 mL of 30% ethanol (v/v). This solution was the test solution for group 10.
(8) Preparation method of test solutions for groups 11: 395.5 mg of Drug D was dissolved in 10 mL of 30% ethanol (v/v). This solution was the test solution for groups 11.
3. On the day prior to the scheduled dosing, the hair (all rat including the positive control group rats with L-DOPA due to the double-blinded fashion) was removed from the up back (around the neck and shoulder) of the animal using a small animal clipper. The animals were re-clipped as necessary throughout the course of the study to keep the epidermis exposed. On the day of dosing, an aliquot (643 µL/kg) of the dosing formulation was administered to a 3 cm by 3 cm square section of the animal (around the neck and shoulder) at around 9 am and repeat it at around 4 µm.
4. At week 4 post lesion, the groups started to receive treatment.
5. Rotarod test will be performed 4 weeks after treatment.
FIG. 5 showed the staying time results in Totarod test described above after 4 weeks treatment (n=12). FIG. 6 showed the falling speed results in Totarod test described above after 4 weeks treatment (n=12).

By pooling all batches data together (12 animals/group), the positive group (L-DOPA, 6 mg/kg, orally) did not exhibit efficacy comparing to the negative control group after four-week treatment, however, all test drug(s) treated groups exhibited stronger efficacy comparing to vehicle group after four-week treatment. Levodopa caused nausea, vomiting, gastrointestinal bleeding, dyskinesia at peak dose, and end-of-dose deterioration of function, so the positive group (L-DOPA, 6 mg/kg, orally) did not exhibit efficacy comparing to Vehicle group. However, the transdermally administrated pro-drug of L-Dopa (Compound C) avoided dyskinesia at peak dose, and end-of-dose deterioration of function. The efficacy of the low dose of Drug C (the pro-drug of L-Dopa, 0.67 mg/kg, group 3) was much higher than that of the moderate and high dose groups of Drug C (2 mg and 6 mg/kg, groups 4 and 5) and this result showed that the dose of transdermally administrated pro-drug of L-dopa was much less than that of orally administrated L-dopa. 15 mg and 45 mg/kg of Drug D (the pro-drug of ibuprofen) exhibited good efficacy comparing to vehicle group and positive control group after four-week treatment. 15 mg of Drug D (group 8) exhibited similar efficacy as 45 mg of Drug D (group 11), so 15 mg/kg dose was enough and higher dose was not necessary. Applying a combination of Drug C and Drug D (group 6 and group 9) worked much better than applying either Drug D (group 8, and 11) or Drug C (group 3) alone.

Example 34

The Efficacy of Pro-Drugs of L-Dopa and Ibuprofen and 1.5 Mg/Kg of Carbidopa on Improvement of Motor Function Deficits and Reduction of Nigro-Striatal Neurodegeneration Induced by 6-OHDA in Parkinson's Disease (PD) Model at HDB Test subjects (Sprague-Dawley rats) were prepared as described in Example 31, and grouped and tested following the protocol below:
1. Rats were divided into 11 groups (n=12), each group was applied with the drug(s) at the doses specified in Table 5:

TABLE 5

Doses and Drug(s) Applied to the Test Animals

| Group No. | Group Name | Drug(s) Applied | Parent drug | Dosage (mg/kg) | Administration Method |
|---|---|---|---|---|---|
| 1 | Positive Control | L-DOPA | N/A | 6 | Oral |
| | | Carbidopa | N/A | 1.5 | Oral |
| 2 | Negative Control | 30% ethanol(v/v) (Vehicle) | N/A | 1,286 (µL/kg) | Transdermal |
| | | Carbidopa | N/A | 1.5 | Oral |

TABLE 5-continued

Doses and Drug(s) Applied to the Test Animals

| Group No. | Group Name | Drug(s) Applied | Parent drug | Dosage (mg/kg) | Administration Method |
|---|---|---|---|---|---|
| 3 | Low dose | Drug C | L-DOPA | 0.67 | Transdermal |
| | | Carbidopa | N/A | 1.5 | Oral |
| 4 | Moderate dose | Drug C | L-DOPA | 2 | Transdermal |
| | | Carbidopa | N/A | 1.5 | Oral |
| 5 | High dose | Drug C | L-DOPA | 6 | Transdermal |
| | | Carbidopa | N/A | 1.5 | Oral |
| 6 | | Drug C | L-DOPA | 0.67 | Transdermal |
| | | Drug D | Ibuprofen | 15 | Transdermal |
| | | Carbidopa | N/A | 1.5 | Oral |
| 7 | | Drug C | L-DOPA | 2 | Transdermal |
| | | Drug D | Ibuprofen | 15 | Transdermal |
| | | Carbidopa | N/A | 1.5 | Oral |
| 8 | | Drug D | Ibuprofen | 15 | Transdermal |
| | | Carbidopa | N/A | 1.5 | Oral |
| 9 | | Drug C | L-DOPA | 0.67 | Transdermal |
| | | Drug D | Ibuprofen | 45 | Transdermal |
| | | Carbidopa | N/A | 1.5 | Oral |
| 10 | | Drug C | L-DOPA | 2 | Transdermal |
| | | Drug D | Ibuprofen | 45 | Transdermal |
| | | Carbidopa | N/A | 1.5 | Oral |
| 11 | | Drug D | Ibuprofen | 45 | Transdermal |
| | | Carbidopa | N/A | 1.5 | Oral |

2. Dose Formulations (1) Both L-DOPA (3 mg/ml) and carbidopa (1.5 mg/mL) in water was used as the positive control solution for group 1 (orally). The volume of administration was 2 mL/kg. Carbidopa in water (1.5 mg/mL) as an aromatic-L-amino-acid decarboxylase inhibitor was applied to groups 2-11 (orally), the volume of administration was 2 mL/kg. Vehicle solution (negative control solution for group 2) was 30% ethanol (v/v), the volume of administration was 1,286 µL/kg. Other test solutions (transdermally, groups 3-11) were freshly prepared every day.

(2) Preparation method of test solutions for groups 3-5: 50.33 mg of Drug C was dissolved in 10 mL of 30% ethanol (v/v). This solution was the stock solution (2).
   a. Preparation of Drug C solution as the test solution for group 5 (high dose group). The stock solution (2) was the test solution for Group 5. The volume of administration was 1,286 µL/kg;
   b. Preparation of Drug C solution as the test solution for group 4 (moderate dose group): 3.00 mL of the stock solution (2) was diluted to final volume 9.00 mL with 30% ethanol (v/v). This solution was the test solution for Group 4. The volume of administration was 1,286 µL/kg;
   c. Preparation of Drug C solution as the test solution for group 3 (low dose group): 1.00 mL of the stock solution (2) was diluted to final volume 9.00 mL with 30% ethanol (v/v). This solution was the test solution for Group 4. The volume of administration was 1,286 µL/kg.

(3) Preparation method of test solutions for group 6: 5.67 mg of Drug C and 132 mg of Drug D were dissolved in 10 mL of 30% ethanol (v/v). This solution was the test solution for groups 6.

(4) Preparation method of test solutions for groups 7: 16.67 mg of Drug C and 132 mg of Drug D were dissolved in 10 mL of 30% ethanol (v/v). This solution was the test solution for groups 7.

(5) Preparation method of test solutions for groups 8: 132 mg of Drug D was dissolved in 10 mL of 30% ethanol (v/v). This solution was the test solution for groups 8.

(6) Preparation method of test solutions for group 9: 5.67 mg of Drug C and 395.5 mg of Drug D were dissolved in 10 mL of 30% ethanol (v/v). This solution was the test solution for groups 9.

(7) Preparation method of test solutions for groups 10: 16.67 mg of Drug C and 395.5 mg of Drug D were dissolved in 10 mL of 30% ethanol (v/v). This solution was the test solution for groups 10.

(8) Preparation method of test solutions for groups 11: 395.5 mg of Drug D was dissolved in 10 mL of 30% ethanol (v/v). This solution was the test solution for groups 11.

3. On the day prior to the scheduled dosing, the hair (all rat including the positive control group rats with L-DOPA due to the double-blinded fashion) was removed from the up back (around the neck and shoulder) of the animal using a small animal clipper. The animals were re-clipped as necessary throughout the course of the study to keep the epidermis exposed. On the day of dosing, an aliquot (643 µL/kg) of the dosing formulation was administered to a 3 cm by 3 cm square section of the animal (around the neck and shoulder) at around 9 am and repeat it at around 4 pm.

4. At week 4 post lesion, the groups started to receive treatment.

5. Rotarod test was performed 4 weeks after treatment.

Figure 7:
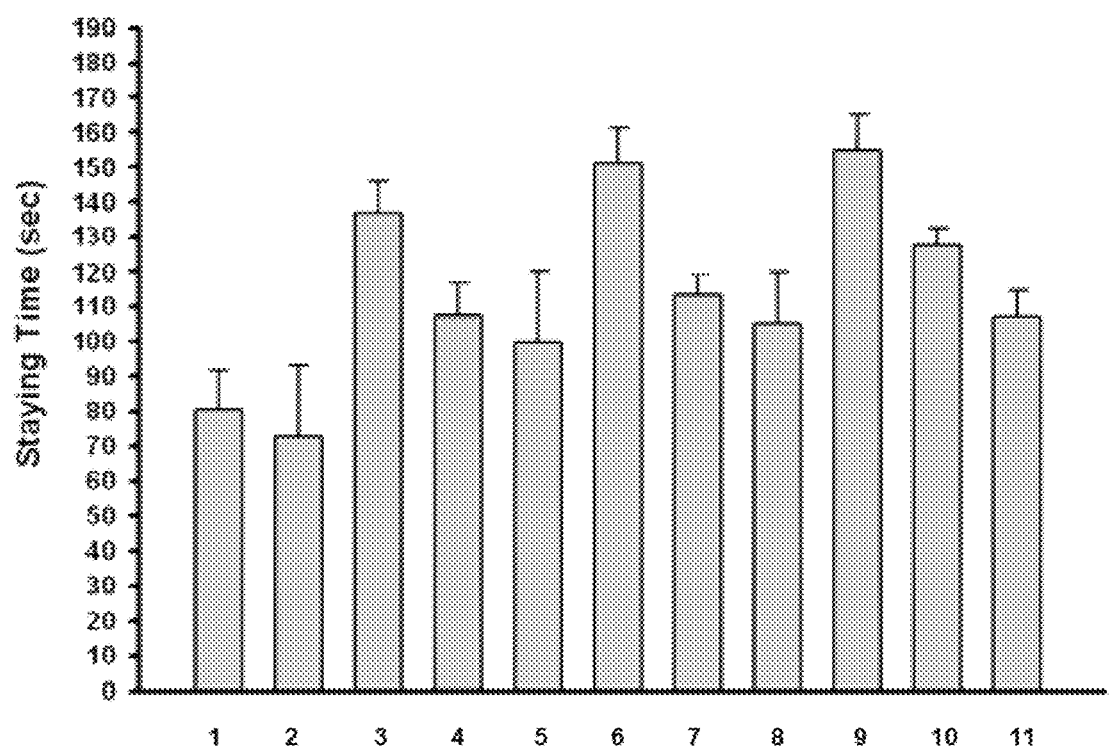
FIG. 7. The staying time results in Totarod test after 4 weeks treatment (n=12) (Example 34).
Figure 8:
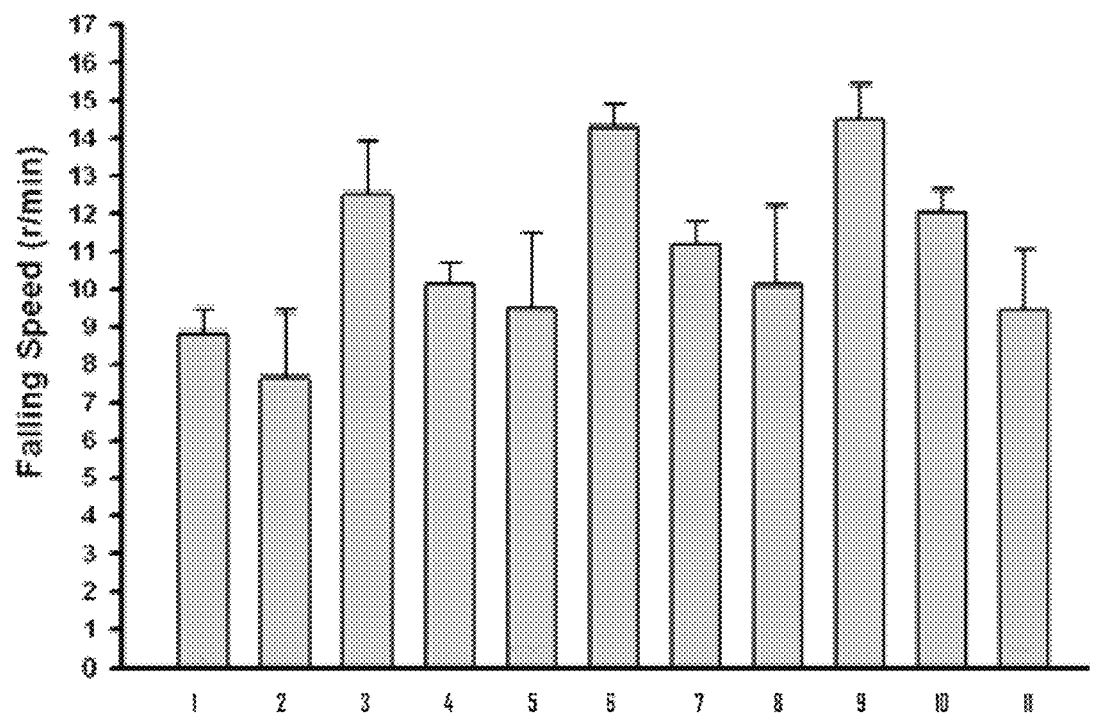
FIG. 8. The falling speed results in Totarod test after 4 weeks treatment (n=12) (Example 34).

FIG. 7 showed the staying time results in Totarod test described above after 4 weeks treatment (n=12). FIG. 8 showed the falling speed results in Totarod test described above after 4 weeks treatment (n=12).

Carbidopa can decrease peripheral DDC conversion of levodopa before it crosses the blood-brain barrier, then reduced the side effects of L-Dopa. The results show that carbidopa increased efficacy of all L-Dopa and the pro-drug of L-Dopa treated groups (groups 1, 3, 4, 5, 6, 7, 9, 10), but did not change the efficacy of vehicle group and pro-drug of ibuprofen treated groups (groups 2, 8 and 11).

Example 35

The Efficacy of 4-(2-(((1-((pyrrolidine-2-carbonyl)oxy)ethoxy)amino)ethyl)-1,2,-phenylene dibenzoate hydrochloride (Drug E) and 4-(dimethylamino)butyl 2-(3-phenoxyphenyl) propionate hydrochloride (Drug F) on Improvement of Motor Function Deficits and Reduction of Nigro-Striatal Neurodegeneration Induced by 6-OHDA in Parkinson's Disease (PD) Model at HDB Test subjects (Sprague-Dawley rats) were prepared as described in Example 31, and grouped and tested following the protocol below:

1. Rats were divided into 11 groups (n=12), each group was applied with the drug(s) at the doses specified in Table 6:

TABLE 6

Doses and Drug(s) Applied to the Test Animals

| Group No. | Group Name | Drug(s) Applied | Parent drug | Dosage (mg/kg) | Administration Method |
|---|---|---|---|---|---|
| 1 | Positive Control | L-DOPA | N/A | 6 | Oral |
| 2 | Negative Control | 30% ethanol(v/v) (Vehicle) | N/A | 1,286 (µL/kg) | Transdermal |
| 3 | Low dose | Drug E | Dopamine | 0.5 | Transdermal |

TABLE 6-continued

Doses and Drug(s) Applied to the Test Animals

| Group No. | Group Name | Drug(s) Applied | Parent drug | Dosage (mg/kg) | Administration Method |
|---|---|---|---|---|---|
| 4 | Moderate dose | | | 1.5 | Transdermal |
| 5 | High dose | | | 4.5 | Transdermal |
| 6 | | Drug E | Dopamine | 0.5 | Transdermal |
| | | Drug F | Fenoprofen | 20 | Transdermal |
| 7 | | Drug E | Dopamine | 1.5 | Transdermal |
| | | Drug F | Fenoprofen | 20 | Transdermal |
| 8 | | Drug F | Fenoprofen | 20 | Transdermal |
| 9 | | Drug E | Dopamine | 0.5 | Transdermal |
| | | Drug F | Fenoprofen | 60 | Transdermal |
| 10 | | Drug E | Dopamine | 1.5 | Transdermal |
| | | Drug F | Fenoprofen | 60 | Transdermal |
| 11 | | Drug F | Fenoprofen | 60 | Transdermal |

2. Dose Formulations
(1) L-DOPA in water (3 mg/mL) was the positive control solution for group 1 (orally for group 1). The volume of administration was 2 mL/kg. Vehicle solution (negative control solution for group 2) was 30% ethanol (v/v). The volume of administration was 1286 μL/kg. Other test solutions (groups 3-11) were freshly prepared every day.
(2) Preparation method of test solutions for groups 3-5: 37.75 mg of Drug E was dissolved in 10 mL of 30% ethanol (v/v). This solution was the stock solution (2).
   a. The test solution for group 5 (high dose group) of Drug E: The stock solution (2) was the test solution for Group 5. The volume of administration was 1,286 μL/kg;
   b. The test solution for group 4 (moderate dose group) of Drug E: 3.00 mL of the stock solution (2) was diluted to final volume 9.00 mL with 30% ethanol (v/v). This solution was the test solution for Group 4. The volume of administration was 1286 μL/kg;
   c. The test solution for group 3 (low dose group) of Drug E: 1.00 mL of the stock solution (2) was diluted to final volume 9.00 mL with 30% ethanol (v/v). This solution was the test solution for Group 3. The volume of administration was 1286 μL/kg.
(3) Preparation method of test solutions for group 6: 4.25 mg of Drug E and 176 mg of Drug E were dissolved in 10 mL of 30% ethanol (v/v). This solution was the test solution for groups 6.
(4) Preparation method of test solutions for groups 7: 12.5 mg of Drug E and 176 mg of Drug E were dissolved in 10 mL of 30% ethanol (v/v). This solution was the test solution for groups 7.
(5) Preparation method of test solutions for groups 8: 176 mg of Drug E was dissolved in 10 mL of 30% ethanol (v/v). This solution was the test solution for groups 8.
(6) Preparation method of test solutions for group 9: 4.25 mg of (Drug E and 527 mg of Drug E were dissolved in 10 mL of 30% ethanol (v/v). This solution was the test solution for groups 9.
(7) Preparation method of test solutions groups 10: 12.5 mg of Drug E and 527 mg of Drug E were dissolved in 10 mL of 30% ethanol (v/v). This solution was the test solution for groups 10.
(8) Preparation method of test solutions for groups 11: 527 mg of 4 Drug E was dissolved in 10 mL of 30% ethanol (v/v). This solution was the test solution for groups 11.
3. On the day prior to the scheduled dosing, the hair (all rat including the positive control group rats with L-DOPA due to the double-blinded fashion) was removed from the up back (around the neck and shoulder) of the animal using a small animal clipper. The animals were re-clipped as necessary throughout the course of the study to keep the epidermis exposed. On the day of dosing, an aliquot (643 μL/kg) of the dosing formulation was administered to a 3 cm by 3 cm square section of the animal (around the neck and shoulder) at around 9 am and repeat it at around 4 μm.
4. At week 4 post lesion, the groups started to receive treatment.
5. Rotarod test was performed 4 weeks after treatment.

Figure 9:
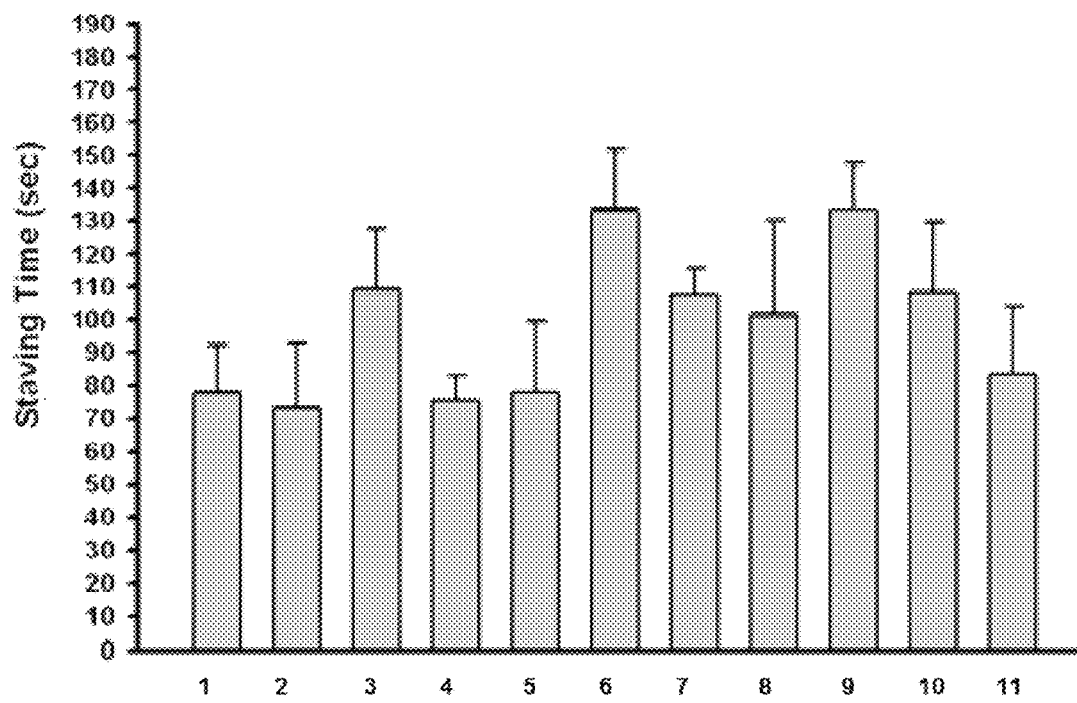
FIG. 9. The falling speed results in Totarod test after 4 weeks treatment (n=12) (Example 35).
Figure 10:
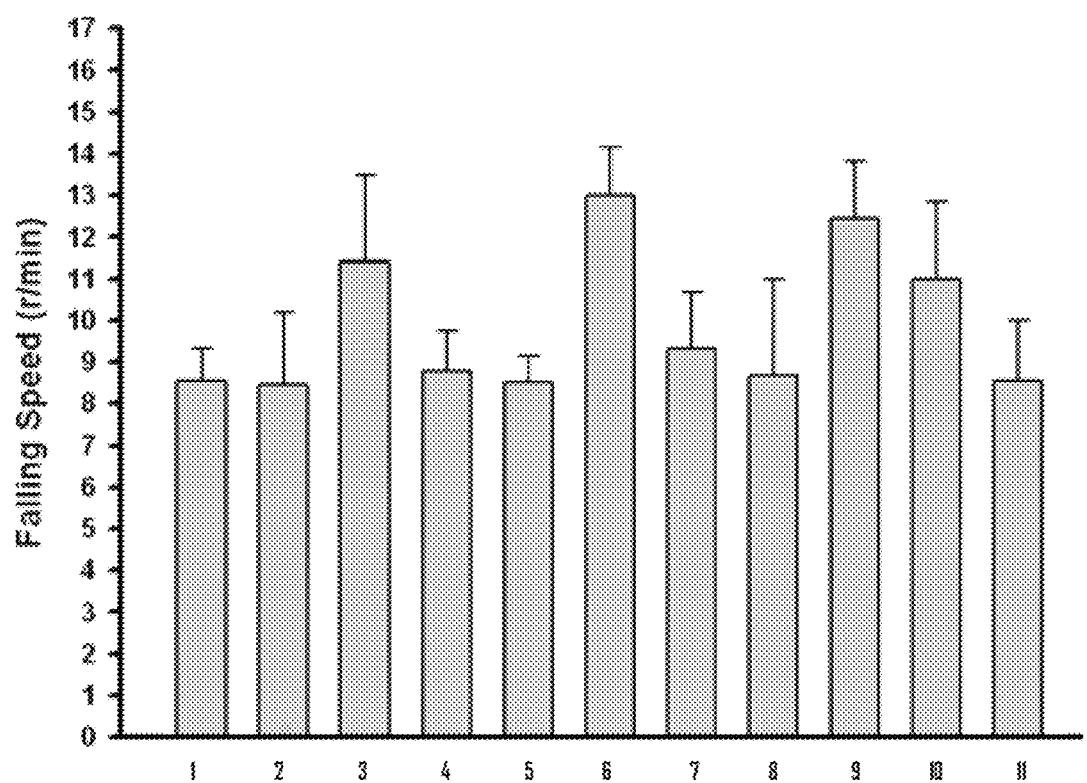
FIG. 10. The falling speed results in Totarod test after 4 weeks treatment (n=12) (Example 35).

FIG. 9 showed the staying time results in Totarod test described above after 4 weeks treatment (n=12). FIG. 10 showed the falling speed results in Totarod test described above after 4 weeks treatment (n=12).

By pooling all batches data together (12 animals/group), the positive group (L-DOPA, 6 mg/kg, orally) did not exhibit efficacy comparing to Vehicle group after four-week treatment. However, all test drug(s) treated groups exhibited stronger efficacy comparing to vehicle group after four-week treatment. Levodopa and dopamine caused nausea, vomiting, gastrointestinal bleeding, dyskinesia at peak dose, and end-of-dose deterioration of function, so the positive group (L-DOPA, 6 mg/kg, orally) did not exhibit efficacy comparing to vehicle group. However, the transdermally administrated pro-drug of dopamine avoided dyskinesia at peak dose, and end-of-dose deterioration of function. The efficacy of the low dose of Drug E (the pro-drug of dopamine, 0.5 mg/kg, group 3) was much higher than that of the moderate and high dose groups of Drug E (1.5 mg and 4.5 mg/kg, group 4 and 5), so higher dose of Drug E may have caused more side effects as L-Dopa did. 20 mg and 60 mg/kg of Drug F exhibited good efficacy comparing to vehicle group and positive control group after four-week treatment. 20 mg/Kg of Drug F (group 8) exhibited similar efficacy as 60 mg/Kg of Drug F (group 11). This result showed that 20 mg/kg dose was sufficient and higher dose was not necessary. Applying a combination of Drug E and Drug F (group 6 and group 9) worked much better than applying either Drug F (groups 8 and 11) or (Drug E (group 3) alone.

When applying a combination of a plurality of drugs (e.g. one or more HPPs and/or other drug(s)) to a subject, each drug could be applied separately, or one or more of the drugs could be applied at substantially the same time as separate drugs (e.g. spraying two or more drugs at substantially the same time without mixing the drugs before spraying), or one or more drugs could be mixed together before applying to the subject, or any combination of the above application methods. The drugs could be applied in any order possible.

Example 36

The Efficacy of Drug G ((S)-4-(2-amino-3-(heptan-4-yloxy)-3-oxopropyl)-1,2-phenylene dibenzoate hydrochloride) and Drug H (2-(dipropylamino)ethyl 4-acetoxy-2',4'-difluoro-[1,1'-biphenyl]-3-carboxylate hydrochloride) on Improvement of Motor Function Deficits and Reduction of Nigro-Striatal Neurodegeneration Induced by 6-OHDA in Parkinson's Disease (PD) Model at HDB Test subjects (Sprague-Dawley rats) were prepared as described in Example 31, and grouped and tested following the protocol below:
1. Rats were divided into 11 groups (n=12), each group was applied with the drug(s) at the doses specified in Table 7:

TABLE 7

Doses and Drug(s) Applied to the Test Animals

| Group No. | Group Name | Drug(s) Applied | Parent drug | Dosage (mg/kg) | Administration Method |
|---|---|---|---|---|---|
| 1 | Positive Control | L-DOPA | N/A | 6 | Oral |
| 2 | Negative Control | 30% ethanol(v/v) (Vehicle) | N/A | 1,286 (µL/kg) | Transdermal |
| 3 | Low dose | Drug G | L-DOPA | 0.67 | Transdermal |
| 4 | Moderate dose | | | 2 | Transdermal |
| 5 | High dose | | | 6 | Transdermal |
| 6 | | Drug G | L-DOPA | 0.67 | Transdermal |
|   | | Drug H | Diflunisal | 15 | Transdermal |
| 7 | | Drug G | L-DOPA | 0.67 | Transdermal |
|   | | Drug H | Diflunisal | 15 | Transdermal |
| 8 | | Drug H | Diflunisal | 15 | Transdermal |
| 9 | | Drug G | L-DOPA | 0.67 | Transdermal |
|   | | Drug H | Diflunisal | 45 | Transdermal |
| 10 | | Drug G | L-DOPA | 2 | Transdermal |
|    | | Drug H | Diflunisal | 45 | Transdermal |
| 11 | | Drug H | Diflunisal | 45 | Transdermal |

2. Dose Formulations (1) L-DOPA in water (3 mg/mL) was the positive control solution for group 1 (orally), the volume of administration was 2 mL/kg. Vehicle solution (negative control solution for group 2) was 30% ethanol (v/v), the volume of administration was 1,286 µL/kg. Other test solutions (groups 3-11) were freshly prepared every day.

(2) Preparation method of test solutions for groups 3-5: 50.33 mg of Drug G was dissolved in 10 mL of 30% ethanol (v/v). This solution was the stock solution (2).
  a. The test solution for group 5 (high dose group) of Drug G: The stock solution (2) was the test solution for Group 5. The volume of administration was 1286 µL/kg;
  b. The test solution for group 4 (moderate dose group) of Drug G: 3.00 mL of the stock solution (2) was diluted to final volume 9.00 mL with 30% ethanol (v/v). This solution was the test solution for Group 4. The volume of administration was 1286 µL/kg.
  c. The test solution for group 3 (low dose group) of Drug G: 1.00 mL of the stock solution (2) was diluted to final volume 9.00 mL with 30% ethanol (v/v). This solution was the test solution for Group 4. The volume of administration was 1286 µL/kg (3) Preparation method of test solutions for group 6: 5.67 mg of Drug G and 132 mg of Drug H were dissolved in 10 mL of 30% ethanol (v/v). This solution was the test solution for groups 6.

(4) Preparation method of test solutions for groups 7: 16.67 mg of Drug G and 132 mg of Drug H were dissolved in 10 mL of 30% ethanol (v/v). This solution was the test solution for groups 7.

(5) Preparation method of test solutions for groups 8: 132 mg of Drug H was dissolved in 10 mL of 30% ethanol (v/v). This solution was the test solution for groups 8.

(6) Preparation method of test solutions for group 9: 5.67 mg of Drug G and 395.5 mg of Drug H were dissolved in 10 mL of 30% ethanol (v/v). This solution was the test solution for groups 9.

(7) Preparation method of test solutions for groups 10: 16.67 mg of Drug G and 395.5 mg of Drug H were dissolved in 10 mL of 30% ethanol (v/v). This solution was the test solution for groups 10.

(8) Preparation method of test solutions for groups 11: 395.5 mg of Drug H was dissolved in 10 mL of 30% ethanol (v/v). This solution was the test solution for groups 11.

3. On the day prior to the scheduled dosing, the hair (all rat including the positive control group rats with L-DOPA due to the double-blinded fashion) was removed from the up back (around the neck and shoulder) of the animal using a small animal clipper. The animals were re-clipped as necessary throughout the course of the study to keep the epidermis exposed. On the day of dosing, an aliquot (643 µL/kg) of the dosing formulation was administered to a 3 cm by 3 cm square section of the animal (around the neck and shoulder) at around 9 am and repeat it at around 4 µm.

4. At week 4 post lesion, the groups started to receive treatment.

5. Rotarod test was performed four weeks after treatment.

Figure 11:
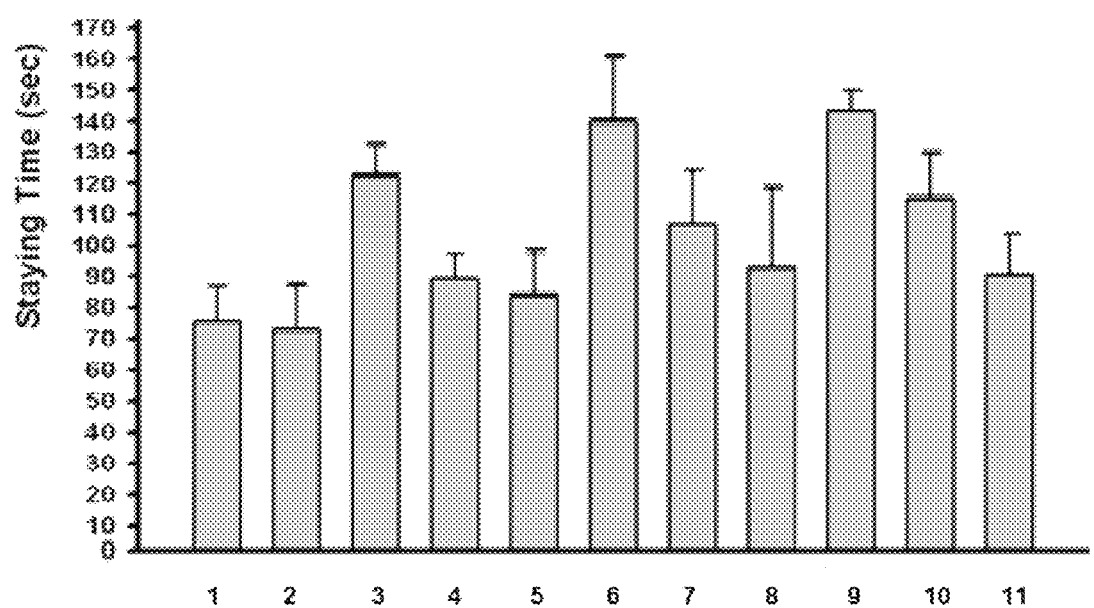
FIG. 11. The staying time results in Totarod test after 4 weeks treatment (n=12) (Example 36).
Figure 12:
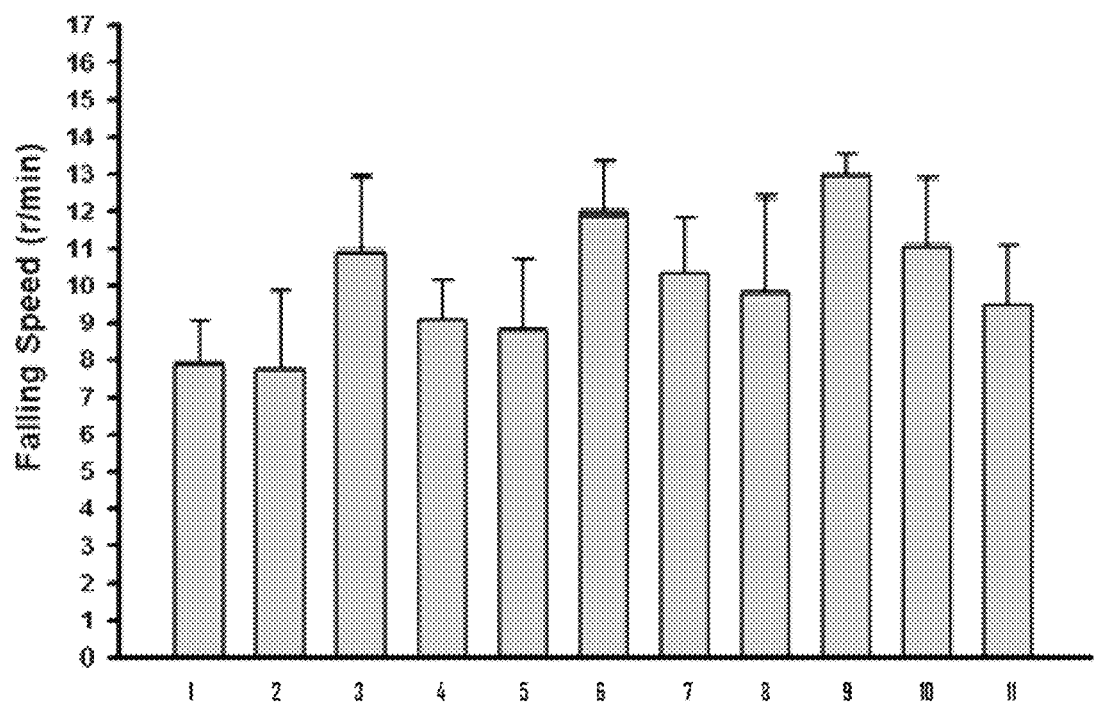
FIG. 12. The falling speed results in Totarod test after 4 weeks treatment (n=12) (Example 36).

FIG. 11 showed the staying time results in Totarod test described above after 4 weeks treatment (n=12). FIG. 12 showed the falling speed results in Totarod test described above after 4 weeks treatment (n=12).

By pooling all batches data together (12 animals/group), the positive group (L-DOPA, 6 mg/kg, orally) did not exhibit efficacy comparing to vehicle group after four-week treatment. However, all test drug(s) treatment groups exhibited stronger efficacy comparing to vehicle group after four-week treatment. Levodopa caused nausea, vomiting, gastrointestinal bleeding, dyskinesia at peak dose, and end-of-dose deterioration of function, so the positive group (L-DOPA, 6 mg/kg, orally) did not exhibit efficacy comparing to vehicle group. However, the transdermally administrated pro-drug of L-Dopa avoided dyskinesia at peak dose, and end-of-dose deterioration of function. The efficacy of the low dose of Drug G (the pro-drug of L-Dopa, 0.67 mg/kg, group 3) was much higher than that of the moderate and high dose groups of Drug G (2 mg and 6 mg/kg, groups 4 and 5). The higher dose may have caused side effects as L-dopa did. 15 mg and 45 mg/kg of Drug H exhibited good efficacy comparing to vehicle group and positive control group after four-week treatment. 15 mg of Drug H (group 8) exhibited similar efficacy as 45 mg of Drug H (group 11). This suggested 15 mg/kg dose was sufficient and higher dose was not necessary. Applying a combination of Drug G and Drug H (group 6 and group 9) worked much better than applying either Drug H (groups 8 and 11) or Drug G (groups 3) alone.

When applying a combination of a plurality of drugs (e.g. one or more HPPs and/or other drug(s)) to a subject, each drug could be applied separately, or one or more of the drugs could be applied at substantially the same time as separate drugs (e.g. spraying two or more drugs at substantially the same time without mixing the drugs before spraying), or one or more drugs could be mixed together before applying to the subject, or any combination of the above application methods. The drugs could be applied in any order possible.

Example 37

The Efficacy of Drug A (Transdermally), Drug B (Transdermally), and Entacapone (Orally) on Improvement of Motor Function Deficits and Reduction of Nigro-Striatal Neurodegeneration Induced by 6-OHDA in Parkinson's Disease (PD) Model at HDB Test subjects (Sprague-Dawley rats) were prepared as described in Example 31, and grouped and tested following the protocol below:

1. Rats were divided into 11 groups (n=12), each group was applied with the drug(s) at the doses specified in Table 8:

TABLE 8

Doses and Drug(s) Applied to the Test Animals

| Group No. | Group Name | Drug(s) Applied | Parent drug | Dosage (mg/kg) | Administration Method |
|---|---|---|---|---|---|
| 1 | Positive Control | L-DOPA | N/A | 6 | Oral |
|   |   | Entacapone | N/A | 25 | Oral |
| 2 | Negative Control | 30% ethanol(v/v) (Vehicle) | N/A | 1,286 (µL/kg) | Transdermal |
|   |   | Entacapone | N/A | 25 | Oral |
| 3 | Low dose | Drug A | L-DOPA | 0.67 | Transdermal |
|   |   | Entacapone | N/A | 25 | Oral |
| 4 | Moderate dose | Drug A | L-DOPA | 2 | Transdermal |
|   |   | Entacapone | N/A | 25 | Oral |
| 5 | High dose | Drug A | L-DOPA | 6 | Transdermal |
|   |   | Entacapone | N/A | 25 | Oral |
| 6 |   | Drug A | L-DOPA | 0.67 | Transdermal |
|   |   | Drug B | Aspirin | 30 | Transdermal |
|   |   | Entacapone | N/A | 25 | Oral |
| 7 |   | Drug A | L-DOPA | 2 | Transdermal |
|   |   | Drug B | Aspirin | 30 | Transdermal |
|   |   | Entacapone | N/A | 25 | Oral |
| 8 |   | Drug B | Aspirin | 30 | Transdermal |
|   |   | Entacapone | N/A | 25 | Oral |
| 9 |   | Drug A | L-DOPA | 0.67 | Transdermal |
|   |   | Drug B | Aspirin | 90 | Transdermal |
|   |   | Entacapone | N/A | 25 | Oral |
| 10 |   | Drug A | L-DOPA | 2 | Transdermal |
|   |   | Drug B | Aspirin | 90 | Transdermal |
|   |   | Entacapone | N/A | 25 | Oral |
| 11 |   | Drug B | Aspirin | 90 | Transdermal |
|   |   | Entacapone | N/A | 25 | Oral |

2. Dose Formulations
(1) Both L-DOPA (3 mg/ml) and entacapone (12.5 mg/mL) in 0.5% CMC-Na (carboxymethylcellulose sodium salt) was the positive control solution for group 1 (orally), the volume of administration was 2 mL/kg. Entacapone (12.5 mg/ml) as a catechol-O-methyl transferase inhibitor in 0.5% CMC-Na was applied to groups 2-11 (orally), the volume of administration was 2 mL/kg. Vehicle solution (negative control solution for group 2) was 30% ethanol (v/v), the volume of administration was 1,286 µL/kg. Other test solutions (transdermally, groups 3-11) were freshly prepared every day.
(2) Preparation method of test solutions for groups 3-5: 50.33 mg of Drug A was dissolved in 10 mL of 30% ethanol (v/v). This solution was the stock solution (2).
   a. The stock solution (2) was the test solution for Group 5 (high dose group) of Drug A. The volume of administration was 1,286 µL/kg;
   b. The test solution for group 4 (moderate dose group) of Drug A: 3.00 mL of the stock solution (2) was diluted to final volume 9.00 mL with 30% ethanol (v/v). This solution was the test solution for Group 4. The volume of administration was 1,286 µL/kg;
   c. The test solution for group 3 (low dose group) of Drug A: 1.00 mL of the stock solution (2) was diluted to final volume 9.00 mL with 30% ethanol (v/v). This solution was the test solution for Group 4. The volume of administration was 1286 µL/kg.
(3) Preparation method of test solutions for group 6: 5.67 mg of Drug A and 264 mg of Drug B were dissolved in 10 mL of 30% ethanol (v/v). This solution was the test solution for groups 6;
(4) Preparation method of test solutions for groups 7: 16.67 mg of Drug A and 264 mg of Drug B were dissolved in 10 mL of 30% ethanol (v/v). This solution was the test solution for groups 7;
(5) Preparation method of test solutions for groups 8: 264 mg of Drug B was dissolved in 10 mL of 30% ethanol (v/v). This solution was the test solution for groups 8;
(6) Preparation method of test solutions for group 9: 5.67 mg of Drug A and 791 mg of Drug B were dissolved in 10 mL of 30% ethanol (v/v). This solution was the test solution for groups 9;
(7) Preparation method of test solutions for groups 10: 16.67 mg of Drug A and 791 mg of Drug B were dissolved in 10 mL of 30% ethanol (v/v). This solution was the test solution for groups 10;
(8) Preparation method of test solutions for groups 11: 791 mg of Drug B was dissolved in 10 mL of 30% ethanol (v/v). This solution was the test solution for groups 11.
3. On the day prior to the scheduled dosing, the hair (all rat including the positive control group rats with L-DOPA due to the double-blinded fashion) was removed from the up back (around the neck and shoulder) of the animal using a small animal clipper. The animals were re-clipped as necessary throughout the course of the study to keep the epidermis exposed. On the day of dosing, an aliquot (643 µL/kg) of the dosing formulation was administered to a 3 cm by 3 cm square section of the animal (around the neck and shoulder) at around 9 am and repeat it at around 4 m.
4. At week 4 post lesion, the groups started to receive treatment.
5. Rotarod test was performed 4 weeks after treatment.

Figure 13:
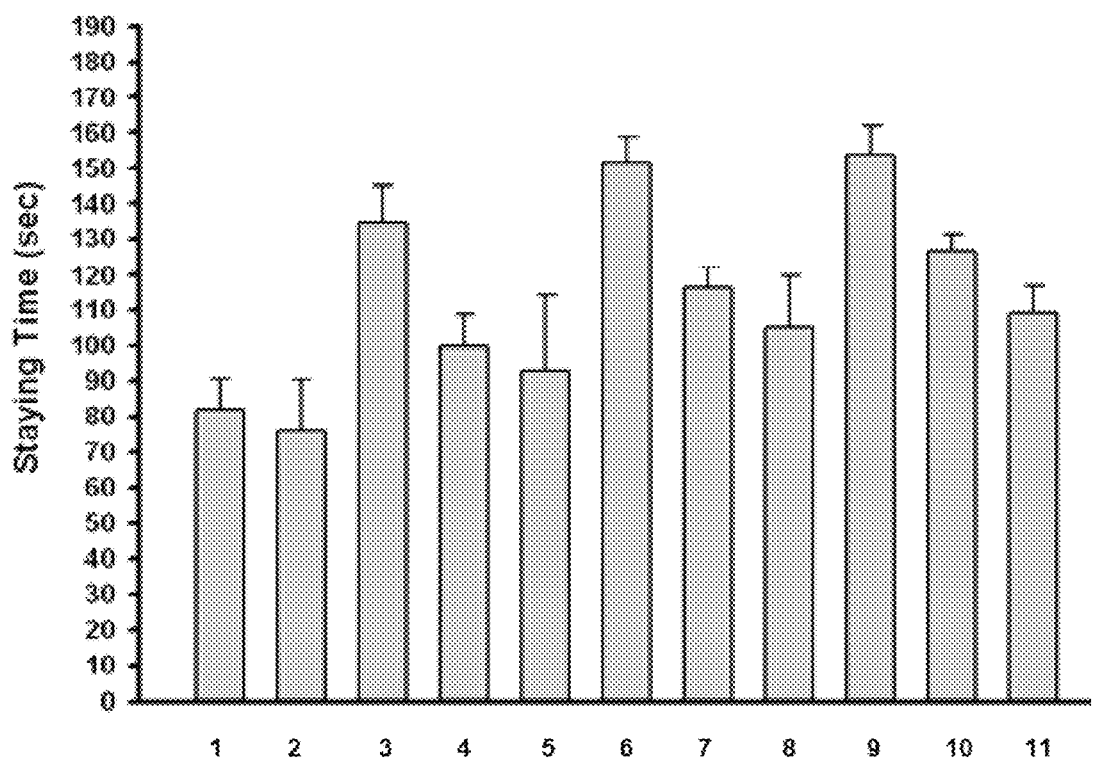
FIG. 13. The staying time results in Totarod test after 4 weeks treatment (n=12) (Example 37).
Figure 14:
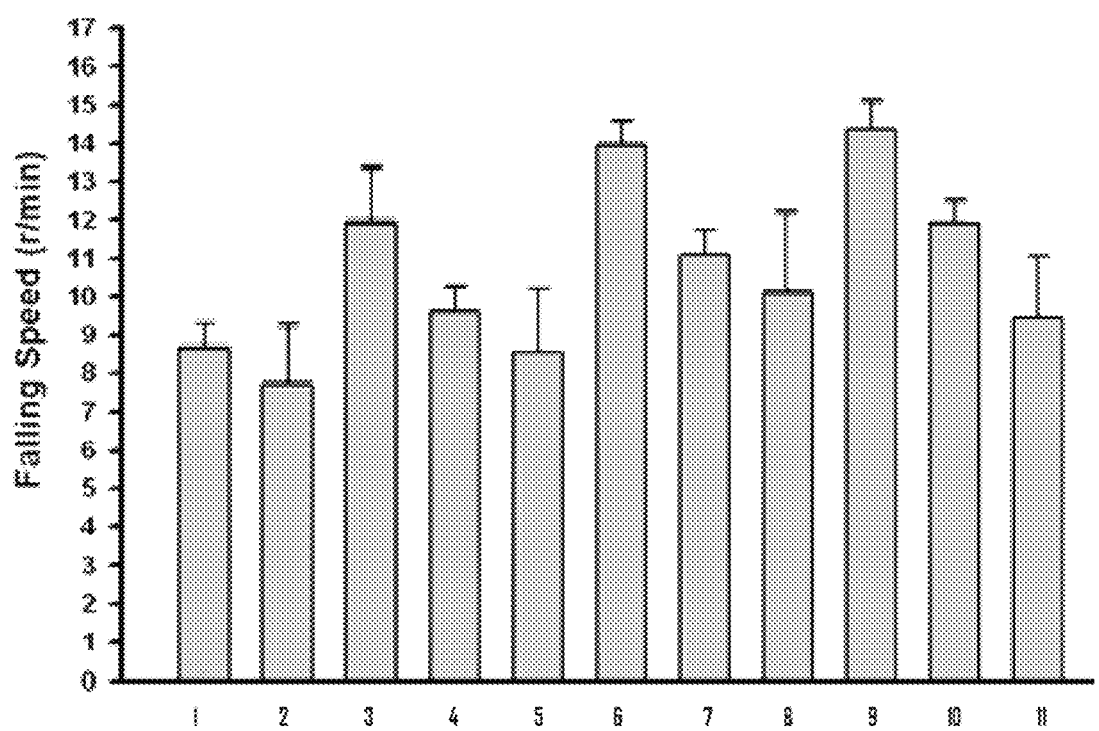
FIG. 14. The falling speed results in Totarod test after 4 weeks treatment (n=12) (Example 37).

FIG. 13 showed the staying time results in Totarod test described above after 4 weeks treatment (n=12). FIG. 14 showed the falling speed results in Totarod test described above after 4 weeks treatment (n=12).

Entacapone was Catechol-O-methyl transferase inhibitors and prevents COMT from metabolizing L-DOPA into 3-methoxy-4-hydroxy-L-phenylalanine in the periphery to avoid the undesirable effects of L-DOPA. The results showed that entacapone increased efficacy of all L-Dopa and the pro-drug of L-Dopa treated groups (groups 1, 3, 4, 5, 6, 7, 9, 10), but did not change the efficacy of vehicle group and pro-drug of aspirin treated groups (groups 2, 8 and 11).

When applying a combination of a plurality of drugs (e.g. one or more HPPs and/or other drug(s)) to a subject, each drug could be applied separately, or one or more of the drugs could be applied at substantially the same time as separate drugs (e.g. spraying two or more drugs at substantially the same time without mixing the drugs before spraying), or one or more drugs could be mixed together before applying to the subject, or any combination of the above application methods. The drugs could be applied in any order possible.

Example 38

The Efficacy of Drug A (Transdermally), Drug B (Transdermally), Entacapone (Orally) and Carbidopa Orally on Improvement of Motor Function Deficits and Reduction of Nigro-Striatal Neurodegeneration Induced by 6-OHDA in Parkinson's Disease (PD) Model at HDB Test subjects (Sprague-Dawley rats) were prepared as described in Example 31, and grouped and tested following the protocol below:
1. Rats were divided into 11 groups (n=12), each group was applied with the drug(s) at the doses specified in Table 9:

TABLE 9

Doses and Drug(s) Applied to the Test Animals

| Group No. | Group Name | Drug(s) Applied | Parent drug | Dosage (mg/kg) | Administration Method |
|---|---|---|---|---|---|
| 1 | Positive Control | L-DOPA | N/A | 6 | Oral |
| | | Entacapone | N/A | 25 | Oral |
| | | Carbidopa | N/A | 1.5 | Oral |
| 2 | Negative Control | 30% ethanol(v/v) (Vehicle) | N/A | 1,286 (µL/kg) | Transdermal |
| | | Entacapone | N/A | 25 | Oral |
| | | Carbidopa | N/A | 1.5 | Oral |
| 3 | Low dose | Drug A | L-DOPA | 0.67 | Transdermal |
| | | Entacapone | N/A | 25 | Oral |
| | | Carbidopa | N/A | 1.5 | Oral |
| 4 | Moderate dose | Drug A | L-DOPA | 2 | Transdermal |
| | | Entacapone | N/A | 25 | Oral |
| | | Carbidopa | N/A | 1.5 | Oral |
| 5 | High dose | Drug A | L-DOPA | 6 | Transdermal |
| | | Entacapone | N/A | 25 | Oral |
| | | Carbidopa | N/A | 1.5 | Oral |
| 6 | | Drug A | L-DOPA | 0.67 | Transdermal |
| | | Drug B | Aspirin | 30 | Transdermal |
| | | Entacapone | N/A | 25 | Oral |
| | | Carbidopa | N/A | 1.5 | Oral |
| 7 | | Drug A | L-DOPA | 2 | Transdermal |
| | | Drug B | Aspirin | 30 | Transdermal |
| | | Entacapone | N/A | 25 | Oral |
| | | Carbidopa | N/A | 1.5 | Oral |
| 8 | | Drug B | Aspirin | 30 | Transdermal |
| | | Entacapone | N/A | 25 | Oral |
| | | Carbidopa | N/A | 1.5 | Oral |
| 9 | | Drug A | L-DOPA | 0.67 | Transdermal |
| | | Drug B | Aspirin | 90 | Transdermal |
| | | Entacapone | N/A | 25 | Oral |
| | | Carbidopa | N/A | 1.5 | Oral |
| 10 | | Drug A | L-DOPA | 2 | Transdermal |
| | | Drug B | Aspirin | 90 | Transdermal |
| | | Entacapone | N/A | 25 | Oral |
| | | Carbidopa | N/A | 1.5 | Oral |
| 11 | | Drug B | Aspirin | 90 | Transdermal |
| | | Entacapone | N/A | 25 | Oral |
| | | Carbidopa | N/A | 1.5 | Oral |

2. Dose Formulations
(1) L-DOPA (3 mg/ml), entacapone (12.5 mg/ml), and carbidopa (1.5 mg/mL) in 0.5% CMC-Na was the positive control solution for group 1 (orally), the volume of administration was 2 mL/kg. Entacapone (12.5 mg/ml), and carbidopa (1.5 mg/mL) in 0.5% CMC-Na was the solution for groups 2-11 (orally), the volume of administration was 2 mL/kg. Vehicle solution (negative control solution for group 2) was 30% ethanol (v/v), the volume of administration was 1,286 µL/kg. Other test solutions (transdermally, groups 3-11) were freshly prepared every day.
(2) Preparation method of test solutions for groups 3-5: 50.33 mg of Drug A was dissolved in 10 mL of 30% ethanol (v/v). This solution was the stock solution (2).
  a. The stock solution (2) was the test solution for Group 5 (high dose group) of Drug A. The volume of administration was 1286 µL/kg;
  b. The test solution for group 4 (moderate dose group) of Drug A. 3.00 mL of the stock solution (2) was diluted to final volume 9.00 mL with 30% ethanol (v/v). This solution was the test solution for Group 4. The volume of administration was 1286 µL/kg;
  c. The test solution for group 3 (low dose group) of Drug A: 1.00 mL of the stock solution (2) was diluted to final volume 9.00 mL with 30% ethanol (v/v). This solution was the test solution for Group 4. The volume of administration was 1286 µL/kg.

Figure 15:
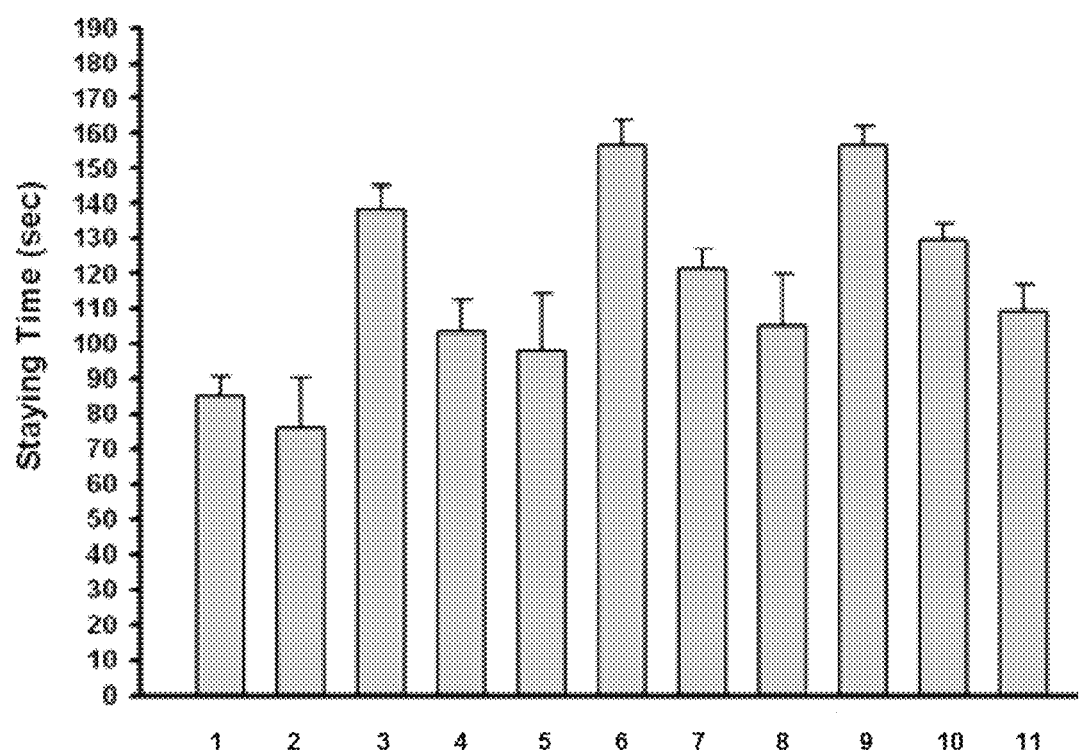
FIG. 15. The staying time results in Totarod test after 4 weeks treatment (n=12) (Example 38).
Figure 16:
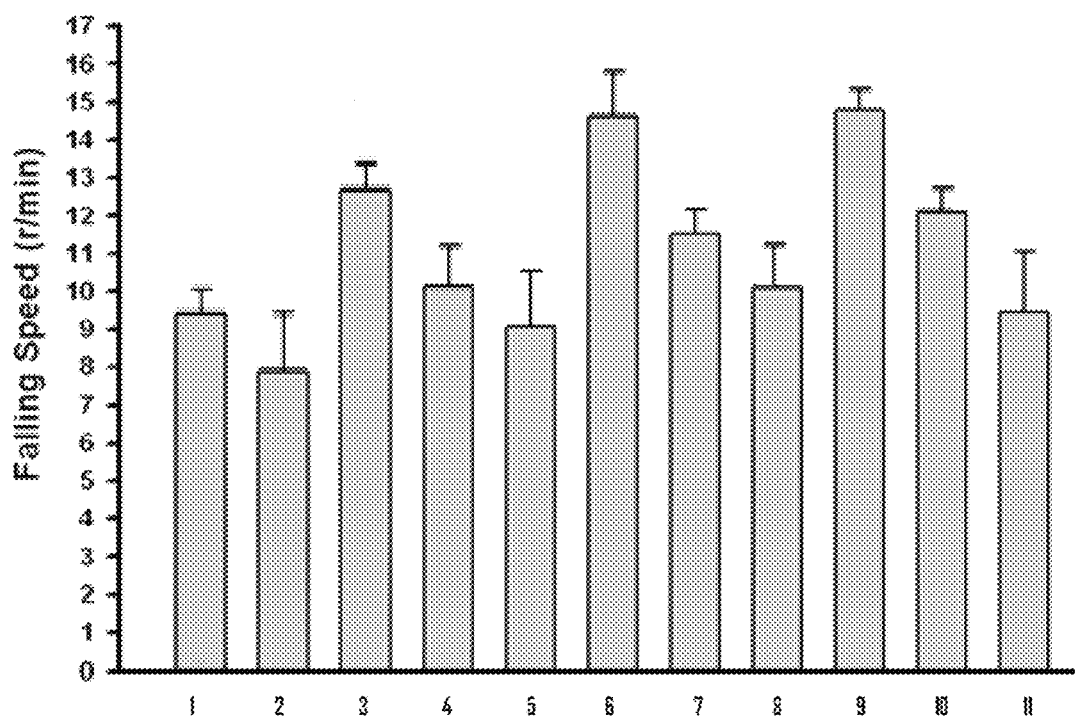
FIG. 16. The falling speed results in Totarod test after 4 weeks treatment (n=12) (Example 38).

(3) Preparation method of test solutions for group 6: 5.67 mg of Drug A and 264 mg of Drug B were dissolved in 10 mL of 30% ethanol (v/v). This solution was the test solution for groups 6;
(4) Preparation method of test solutions for groups 7: 16.67 mg of Drug A and 264 mg of Drug B were dissolved in 10 mL of 30% ethanol (v/v). This solution was the test solution for groups 7;
(5) Preparation method of test solutions for groups 8: 264 mg of Drug B was dissolved in 10 mL of 30% ethanol (v/v). This solution was the test solution for groups 8;
(6) Preparation method of test solutions for group 9: 5.67 mg of Drug A and 791 mg of Drug B were dissolved in 10 mL of 30% ethanol (v/v). This solution was the test solution for groups 9;
(7) Preparation method of test solutions for groups 10: 16.67 mg of Drug A and 791 mg of Drug B were dissolved in 10 mL of 30% ethanol (v/v). This solution was the test solution for groups 10;
(8) Preparation method of test solutions for groups 11: 791 mg of Drug B was dissolved in 10 mL of 30% ethanol (v/v). This solution was the test solution for groups 11.
3. On the day prior to the scheduled dosing, the hair (all rat including the positive control group rats with L-DOPA due to the double-blinded fashion) was removed from the up back (around the neck and shoulder) of the animal using a small animal clipper. The animals were re-clipped as necessary throughout the course of the study to keep the epidermis exposed. On the day of dosing, an aliquot (643 µL/kg) of the dosing formulation was administered to a 3 cm by 3 cm square section of the animal (around the neck and shoulder) at around 9 am and repeat it at around 4 pm.
4. At week 4 post lesion, the groups started to receive treatment.
5. Rotarod test was performed 4 weeks after treatment.
FIG. 15 showed the staying time results in Totarod test described above after 4 weeks treatment (n=12). FIG. 16 showed the falling speed results in Totarod test described above after 4 weeks treatment (n=12).

Applying a combination of carbidopa and entacapone worked better than applying either carbidopa or entacapone alone. The results showed that the combination of carbidopa and entacapone increased efficacy of all L-Dopa and the pro-drug of L-Dopa treated groups (groups 1, 3, 4, 5, 6, 7, 9, 10), but did not change the efficacy of vehicle group and pro-drug of aspirin treated groups (groups 2, 8 and 11).

When applying a combination of a plurality of drugs (e.g. one or more HPPs and/or other drug(s)) to a subject, each drug could be applied separately, or one or more of the drugs could be applied at substantially the same time as separate drugs (e.g. spraying two or more drugs at substantially the same time without mixing the drugs before spraying), or one or more drugs could be mixed together before applying to the subject, or any combination of the above application methods. The drugs could be applied in any order possible.

Example 39

Treatment of Parkinson's Disease and Related Conditions

A solution of 15 mg of Drug A and 30 mg of Drug B in 0.5 ml of water is applied (transdermally) to the skin on the neck, chest, back and any other parts of a subject every 3-10 hours as need.

Example 40

Treatment of Parkinson's Disease and Related Conditions

A solution of 10 mg of Drug A and 20 mg of Drug B in 0.5 ml of water is applied (transdermally) to the skin on the neck, chest, back and any other parts of a subject every 3-10 hours as need.

Example 41

Treatment of Parkinson's Disease and Related Conditions

A solution of 20 mg of Drug A and 40 mg of Drug B in 0.5 ml of water is applied (transdermally) to the skin on the neck, chest, back and any other parts of a subject every 3-10 hours as need.

Example 42

Treatment of Parkinson's Disease and Related Conditions

A solution of 30 mg of Drug A and 50 mg of Drug B in 0.5 ml of water is applied (transdermally) to the skin on the neck, chest, back and any other parts of a subject every 3-10 hours as need.

Example 43

Treatment of Parkinson's Disease and Related Conditions

A solution of 15 mg of Drug A and 30 mg of Drug B in 0.5 ml of water is applied (transdermally) to the skin on the neck, chest, back and/or any other parts of a subject every 3-10 hours as need. After or before applying the above solution, a tablet containing 10 mg of carbidopa and/or inactive ingredients, such as, cellulose, mannitol, croscarmellose sodium, vegetable oil, hydroxypropyl methylcellulose, is taken orally to increase the efficacy of the transdermally treatment.

Example 44

Treatment of Parkinson's Disease and Related Conditions

A solution of 20 mg of Drug A and 40 mg of Drug B in 0.5 ml of water is applied (transdermally) to the skin on the neck, chest, back and/or any other parts of a subject every 3-10 hours as need. After or before applying the above solution, a tablet containing 15 mg of carbidopa and/or inactive ingredients, such as, cellulose, mannitol, croscarmellose sodium, vegetable oil, hydroxypropyl methylcellulose, is taken orally to increase the efficacy of the transdermally treatment.

Example 45

Treatment of Parkinson's Disease and Related Conditions

A solution of 15 mg of Drug A and 30 mg of Drug B in 0.5 ml of water is applied (transdermally) to the skin on the neck, chest, back and/or any other parts of a subject every 3-10 hours. After or before applying the above solution, a tablet containing 15 mg of carbidopa, 70 mg of entacapone and/or inactive ingredients, such as, cellulose, mannitol, croscarmellose sodium, vegetable oil, hydroxypropyl methylcellulose, is taken orally to increase the efficacy of the transdermally treatment.

Example 46

Treatment of Parkinson's Disease and Related Conditions

A solution of 20 mg of Drug A and 40 mg of Drug B in 0.5 ml of water is applied (transdermally) to the skin on the neck, chest, back and/or any other parts of a subject every 3-10 hours. After or before applying the above solution, a tablet containing 15 mg of carbidopa, 100 mg of entacapone and/or inactive ingredients, such as, cellulose, mannitol, croscarmellose sodium, vegetable oil, hydroxypropyl methylcellulose, is taken orally to increase the efficacy of the transdermally treatment.

Example 47

Treatment of Parkinson's Disease and Related Conditions

A solution of 10 mg of Drug C and 15 mg of Drug D in 0.5 ml of water is applied (transdermally) to the skin on the neck, chest, back and/or any other parts of a subject every 3-10 hours.

Example 49

Treatment of Parkinson's Disease and Related Conditions

A solution of 30 mg of Drug C and 30 mg of Drug D in 0.5 ml of water is applied (transdermally) to the skin on the neck, chest, back and/or any other parts of a subject every 3-10 hours.

Example 50

Treatment of Parkinson's Disease and Related Conditions

A solution of 20 mg of Drug C and 15 mg of Drug D in 0.5 ml of water is applied (transdermally) to the skin on the neck, chest, back and/or any other parts of a subject every 3-10 hours. After or before applying the above solution, a tablet containing 15 mg of carbidopa and/or inactive ingredients, such as, cellulose, mannitol, croscarmellose sodium, vegetable oil, hydroxypropyl methylcellulose, is taken orally to increase the efficacy of the transdermally treatment.

Example 51

Treatment of Parkinson's Disease and Related Conditions

A solution of 10 mg of Drug C and 10 mg of Drug D in 0.5 ml of water is applied (transdermally) to the skin on the neck, chest, back and/or any other parts of a subject every 3-10 hours. After or before applying the above solution, a tablet containing 15 mg of carbidopa, 100 mg of entacapone and/or inactive ingredients, such as, cellulose, mannitol, croscarmellose sodium, vegetable oil, hydroxypropyl methylcellulose, is taken orally to increase the efficacy of the transdermally treatment.

Example 52

Treatment of Parkinson's Disease and Related Conditions

A solution of 30 mg of Drug C and 20 mg of Drug D in 0.5 ml of water is applied (transdermally) to the skin on the neck, chest, back and/or any other parts of a subject every 3-10 hours. After or before applying the above solution, a tablet containing 15 mg of carbidopa, 70 mg of entacapone and/or inactive ingredients, such as, cellulose, mannitol, croscarmellose sodium, vegetable oil, hydroxypropyl methylcellulose, is taken orally to increase the efficacy of the transdermally treatment.

Example 53

Treatment of Parkinson's Disease and Related Conditions

A solution of 30 mg of Drug C and 25 mg of Drug D in 0.5 ml of water is applied (transdermally) to the skin on the neck, chest, back and/or any other parts of a subject every 3-10 hours. After or before applying the above solution, a tablet containing 10 mg of carbidopa, 50 mg of entacapone and/or inactive ingredients, such as, cellulose, mannitol, croscarmellose sodium, vegetable oil, hydroxypropyl methylcellulose, is taken orally to increase the efficacy of the transdermally treatment.

Example 54

Treatment of Parkinson's Disease and Related Conditions

A solution of 10 mg of Drug E and 10 mg of Drug F in 0.5 ml of water is applied (transdermally) to the skin on the neck, chest, back and/or any other parts of a subject every 3-10 hours.

Example 55

Treatment of Parkinson's Disease and Related Conditions

A solution of 20 mg of Drug E and 20 mg of Drug F in 0.5 ml of water is applied (transdermally) to the skin on the neck, chest, back and/or any other parts of a subject every 3-10 hours.

Example 56

Treatment of Parkinson's Disease and Related Conditions

A solution of 5 mg of Drug E and 10 mg of Drug F in 0.5 ml of water is applied (transdermally) to the skin on the neck, chest, back and/or any other parts of a subject every 3-10 hours.

Example 57

Treatment of Parkinson's Disease and Related Conditions

A solution of 10 mg of Drug G and 10 mg of Drug H in 0.5 ml of water is applied (transdermally) to the skin on the neck, chest, back and/or any other parts of a subject every 3-10 hours.

Example 58

Treatment of Parkinson's Disease and Related Conditions

A solution of 15 mg of Drug G and 15 mg of Drug H in 0.5 ml of water is applied (transdermally) to the skin on the neck, chest, back and/or any other parts of a subject every 3-10 hours.

Example 59

Treatment of Parkinson's Disease and Related Conditions

A solution of 20 mg of Drug G and 15 mg of Drug H in 0.5 ml of water is applied (transdermally) to the skin on the neck, chest, back and/or any other parts of a subject every 3-10 hours.

Example 60

Treatment of Parkinson's Disease and Related Conditions

A solution of 20 mg of Drug G and 15 mg of Drug H in 0.5 ml of water is applied (transdermally) to the skin on the neck, chest, back and/or any other parts of a subject every 3-10 hours. After or before applying the above solution, a tablet containing 10 mg of carbidopa, 70 mg of entacapone and/or inactive ingredients, such as, cellulose, mannitol, croscarmellose sodium, vegetable oil, hydroxypropyl methylcellulose, is taken orally to increase the efficacy of the transdermally treatment.

Example 61

Treatment of Parkinson's Disease and Related Conditions

A solution of 10 mg of Drug G and 10 mg of Drug H in 0.5 ml of water is applied (transdermally) to the skin on the neck, chest, back and/or any other parts of a subject every 3-10 hours. After or before applying the above solution, a tablet containing 10 mg of carbidopa, 50 mg of entacapone and/or inactive ingredients, such as, cellulose, mannitol, croscarmellose sodium, vegetable oil, hydroxypropyl methylcellulose, is taken orally to increase the efficacy of the transdermally treatment.

Example 62

Treatment of Parkinson's Disease and Related Conditions

A solution of 20 mg of Drug G and 15 mg of Drug H in 0.5 ml of water is applied (transdermally) to the skin on the neck, chest, back and/or any other parts of a subject every 3-10 hours. After or before applying the above solution, a tablet containing 15 mg of carbidopa, 100 mg of entacapone and/or inactive ingredients, such as, cellulose, mannitol, croscarmellose sodium, vegetable oil, hydroxypropyl methylcellulose, is taken orally to increase the efficacy of the transdermally treatment.

What is claimed is:

1. A method for treating Parkinson disease in a subject comprising administering transdermally a pharmaceutical composition comprising one or more high penetration prodrugs selected from Structure Pro-L-Dopa-1, Structure Pro-L-Dopa-2, Structure Pro-L-Dopa-3, Structure Pro-L-Dopa-4, Structure Pro-L-Dopa-5, Structure Pro-dopamine-1, Structure Pro-dopamine-2, Structure Pro-dopamine-3, Structure Pro-dopamine-4, and Structure Pro-dopamine-5:

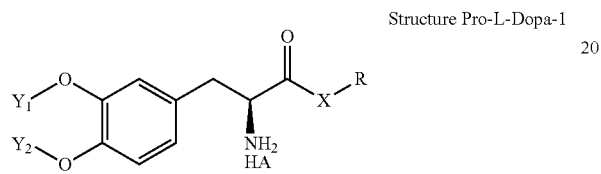

Structure Pro-L-Dopa-1

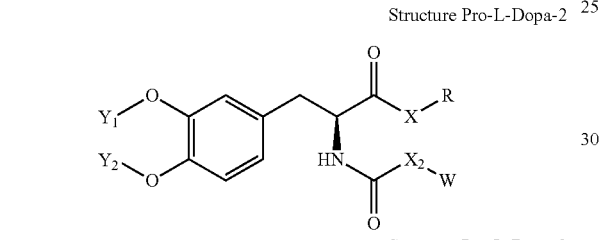

Structure Pro-L-Dopa-2

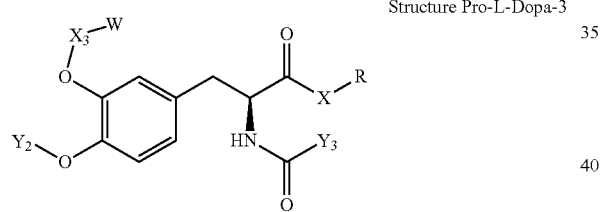

Structure Pro-L-Dopa-3

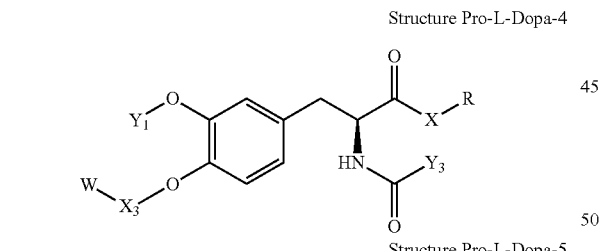

Structure Pro-L-Dopa-4

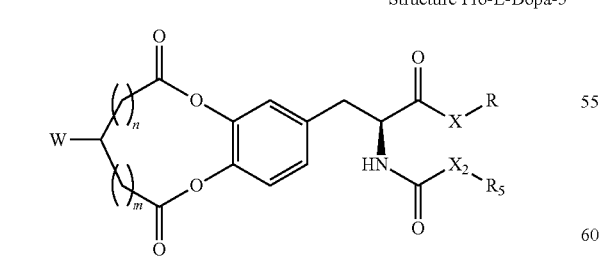

Structure Pro-L-Dopa-5

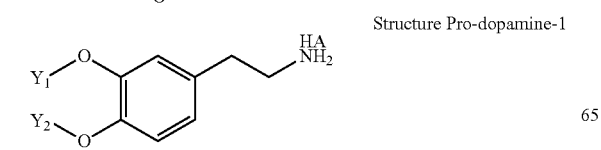

Structure Pro-dopamine-1

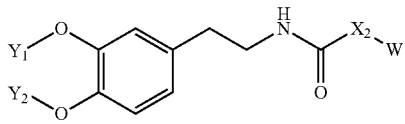

Structure Pro-dopamine-2

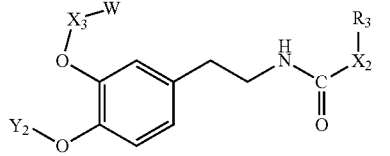

Structure Pro-dopamine-3

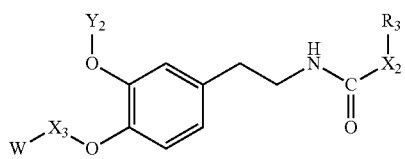

Structure Pro-dopamine-4

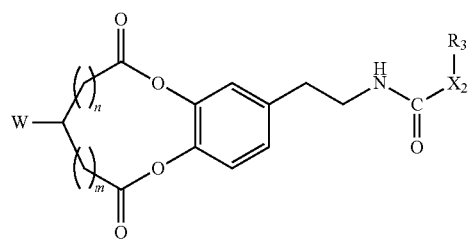

Structure Pro-dopamine-5 stereoisomers, and pharmaceutically acceptable salts thereof, wherein W is selected from H, substituted and unsubstituted alkyl, substituted and unsubstituted cycloalkyl, substituted and unsubstituted heterocycloalkyl, substituted and unsubstituted alkyloxy, substituted and unsubstituted alkenyl, substituted and unsubstituted alkynyl, substituted and unsubstituted aryl, substituted and unsubstituted heteroaryl, the protonatable amine group, pharmaceutically acceptable substituted and unsubstituted amine groups, Structure W-1, Structure W-2, Structure W-3, Structure W-4, Structure W-5, Structure W-6, Structure W-7, Structure W-8, Structure W-9, Structure W-10, Structure W-11, and Structure W-12:

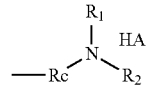

Structure W-1

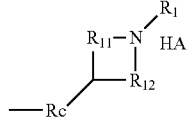

Structure W-2

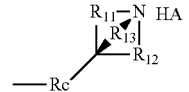

Structure W-3

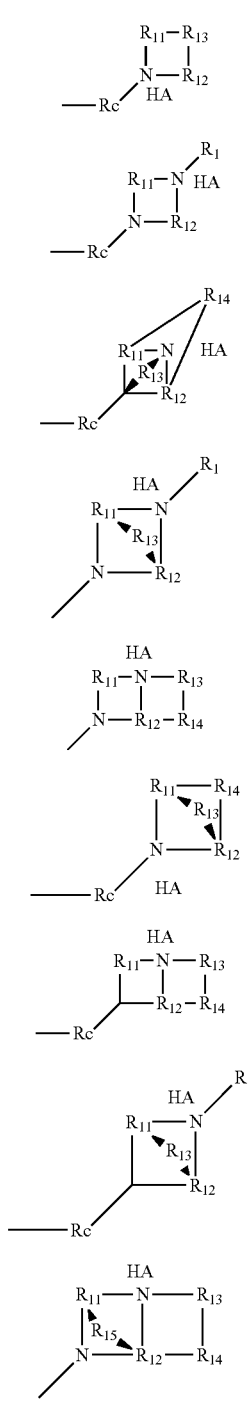

HA is selected from nothing and a pharmaceutically acceptable acid;
X is selected from O, S, and $NR_3$;
$X_2$ is selected from nothing, O, S, $NR_3$, $CHR_3$—O, $CHR_3$—S, $CHR_3$—O, O—$CHR_3$—O, O—$CHR_3$—S, S—$CHR_3$—O, and S—$CHR_3$—S;
$X_3$ is selected from nothing, C=O, C=S, C(=O)—O, O, S, $NR_3$, C(=O)—O—$CHR_3$—O, C(=O)—O—$CHR_3$—S, C(=O)—S—$CHR_3$—O, and C(=O)—S—$CHR_3$—S;
$Y_1$ is selected from $R_3C$(=O), $R_3O$—C(=O), and $R_3S$—C(=O);
$Y_2$ is selected from $R_3C$(=O), $R_3O$—C(=O), and $R_3S$—C(=O);
$Y_3$ is selected from $R_3$, $OR_3$, $SR_3$, $NR_3R_4$, O—$CHR_3$—$OR_4$, O—$CHR_3$—$SR_4$, S—$CHR_3$—$OR_4$;
n and m are independently selected from 0, 1, 2, 3, 4, 5, 6, 7, and 8;
Rc is selected from nothing, $CH_2C$(=O)$OR_6$, substituted and unsubstituted alkyl, substituted and unsubstituted cycloalkyl, substituted and unsubstituted heterocycloalkyl, substituted and unsubstituted alkoxyl, substituted and unsubstituted perfluoroalkyl, substituted and unsubstituted alkyl halide, substituted and unsubstituted alkenyl, substituted and unsubstituted alkynyl, substituted and unsubstituted aryl, and substituted and unsubstituted heteroaryl, wherein any $CH_2$ in R may be further replaced with O, S, P, $NR_6$, or any other pharmaceutically acceptable groups;
R is selected from nothing, $CH_2C$(=O)$OR_6$, substituted and unsubstituted alkyl, substituted and unsubstituted cycloalkyl, substituted and unsubstituted heterocycloalkyl, substituted and unsubstituted alkoxyl, substituted and unsubstituted perfluoroalkyl, substituted and unsubstituted alkyl halide, substituted and unsubstituted alkenyl, substituted and unsubstituted alkynyl, substituted and unsubstituted aryl, and substituted and unsubstituted heteroaryl, wherein any $CH_2$ in R may be further replaced with O, S, P, $NR_6$, or any other pharmaceutically acceptable groups;
$R_3$ is selected from nothing, $CH_2C$(=O)$OR_6$, substituted and unsubstituted alkyl, substituted and unsubstituted cycloalkyl, substituted and unsubstituted heterocycloalkyl, substituted and unsubstituted alkoxyl, substituted and unsubstituted perfluoroalkyl, substituted and unsubstituted alkyl halide, substituted and unsubstituted alkenyl, substituted and unsubstituted alkynyl, substituted and unsubstituted aryl, and substituted and unsubstituted heteroaryl, wherein any $CH_2$ in R may be further replaced with O, S, P, $NR_6$, or any other pharmaceutically acceptable groups;
each $R_6$ is independently selected from H, F, Cl, Br, I, $Na^+$, $K^+$, C(=O)$R_5$, 2-oxo-1-imidazolidinyl, phenyl, 5-indanyl, 2,3-dihydro-1H-inden-5-yl, 4-hydroxy-1,5-naphthyridin-3-yl, substituted and unsubstituted alkyl, substituted and unsubstituted cycloalkyl, substituted and unsubstituted heterocycloalkyl, substituted and unsubstituted alkenyl, substituted and unsubstituted alkynyl, substituted and unsubstituted alkyloxyl, substituted and unsubstituted cycloalkyloxyl, substituted and unsubstituted aryl, and substituted and unsubstituted heteroaryl;
each $R_5$ is independently selected from H, C(=O)$NH_2$, $CH_2CH_2N(CH_3)_2$, $CH_2CH_2N(CH_2CH_3)_2$, Cl, F, Br, I, substituted and unsubstituted alkyl, substituted and unsubstituted cycloalkyl, substituted and unsubstituted heterocycloalkyl, substituted and unsubstituted alkyloxyl, substituted and unsubstituted cycloalkyloxyl, substituted and unsubstituted aryl, substituted and unsubstituted heteroaryl, substituted and unsubstituted alkylcarbonyl, and substituted and unsubstituted alkylamino;
$R_1$ and $R_2$ are independently selected from H, substituted and unsubstituted alkyl, substituted and unsubstituted cycloalkyl, substituted and unsubstituted heterocycloalkyl, substituted and unsubstituted alkyloxyl, substituted and unsubstituted alkenyl, substituted and unsubstituted alkynyl, substituted and unsubstituted aryl and substituted and unsubstituted heteroaryl residues;

$R_{11}$-$R_{15}$ are independently selected from nothing, H, substituted and unsubstituted alkyl, substituted and unsubstituted cycloalkyl, substituted and unsubstituted heterocycloalkyl, substituted and unsubstituted alkoxyl, substituted and unsubstituted perfluoroalkyl, substituted and unsubstituted alkyl halide, substituted and unsubstituted alkenyl, substituted and unsubstituted alkynyl, substituted and unsubstituted aryl, and substituted and unsubstituted heteroaryl;

and an agent selected from a high penetration prodrug of aspirin, a high penetration prodrug of another non-steroidal anti-inflammatory drug (NSAID), and any combination thereof; and administering orally an aromatic-L-amino-acid decarboxylase inhibitor selected from carbidopa, benserazide, difluromethyldopa, α-methyldopa, and a pharmaceutical composition thereof;

and/or administering a catechol-O-methyl transferase inhibitor selected from entacapone, tolcapone; and a pharmaceutical composition thereof.

2. A method for treating Parkinson disease in a subject comprising administering transdermally a pharmaceutical composition comprising 4-(2-(2-(methylamino)acetamido)ethyl)-1,2,-phenylene dibenzoate hydrochloride, 4-(2-(2-(methylamino)acetamido)ethyl)-1,2,-phenylene dibenzoate acetic acid, 4-(6-methyl-4,8-dioxo-5,7-dioxa-2,9-diazadecan-11-yl)-1,2,-phenylene dibenzoate hydrobromide, 4-(2-(2-amino-3-phenylpropanamido)ethyl)-1,2,-phenylene dibenzoate hydrochloride, 4-(2-(((1-((pyrrolidine-2-carbonyl)oxy)ethoxy)amino)ethyl)-1,2,-phenylene dibenzoate hydrochloride, 4-(2-piperidine-4-carboxamido)ethyl)-1,2,-phenylene bis(2-ethylbutanoate) hydrochloride, 4-(2-((((-octahydro-1H-quinolizin-3-yl)oxy)carbonyl)amino)ethyl)-1,2,-phenylene bis(2-ethylbutanoate) acetate, 1-(((2-(4-amino-2,5-dioxo-2,3,4,5-tetrahydrobenzo[b][1,4]dioxocin-8-yl)ethyl)carbamoyl)oxy)ethyl isobutyrate hydrofluoride, 1-(((2-(3-amino-2,5-dioxo-2,3,4,5-tetrahydrobenzo[b][1,4]dioxocin-8-yl)ethyl)carbamoyl)oxy)ethyl isobutyrate hydrofluoride, (-(2-((ethoxycarbonyl)amino)ethyl)-2-(2-methylamino)acetoxy)phenyl benzoate hydrochloride, 5-(2-((ethoxycarbonyl)amino)ethyl)-2-(2-methylamino)acetoxy)phenyl benzoate hydrochloride, 4-(2-aminoethyl)-1,2-phenylene dibenzoate hydrochloride, (S)-4-(2-amino-3-isopropoxy-3-oxopropyl)-1,2-phenylene dibenzoate hydrochloride, (S)-4-(2-amino-3-(heptan-4-yloxy)-3-oxopropyl)-1,2-phenylene dibenzoate hydrochloride, (S)-4-(2-amino-3-isopropoxy-3-oxopropyl)-1,2-phenylene dipentanoate hydrochloride, (S)-4-(2-amino-3-ethoxy-3-oxopropyl)-1,2-phenylene diacetate hydrochloride, (S)-4-(2-amino-3-oxo-3-(pentan-3-yloxy)propyl)-1,2-phenylene bis(2-methylpropanoate) hydrobromide, (S)-4-(2-aminoacetamido)-3-isopropoxy-3-oxopropyl)-1,2-phenylene dibenzoate hydrochloride, 4-((2S)-3-oxo-3-(pentan-3-yloxy)-2-(pyrrolidine-2-carboxamido)propyl)-1,2-phenylene dibenzoate hydrofluoride, (S)-4-(3-isopropoxy-3-oxo-2-(piperidine-4-carboxamido)propyl)-1,2-phenylene dibenzoate hydrochloride, 4-((2S)-3-isopropoxy-3-2-(octahydro-1H-quinolizine-2-carboxamido)-3-oxopropyl)-1,2-phenylene bis(2-methylpropanoate) hydrochloride, (2S)-isopropyl 3-(3-amino-2,5-dioxo-2,3,4,5-tetrahydrobenzo[b][1,4]dioxocin-8-yl)-2-(((1-(isobutyryloxy)ethoxy)carbonyl)amino)propanoate hydrobromide, (2S)-isopropyl 3-(4-amino-2,5-dioxo-2,3,4,5-tetrahydrobenzo[b][1,4]dioxocin-8-yl)-2-(((1-(isobutyryloxy)ethoxy)carbonyl)amino)propanoate hydrobromide, 5-((2S)-2-(((1-(isobutyryloxy)ethoxy)carbonyl)amino-3-isopropoxy-3-oxopropyl)-2-(2-(methylamino)acetoxy)phenyl benzoate hydrochloride, 4-((2S)-2-(((1-(isobutyryloxy)ethoxy)carbonyl)amino-3-isopropoxy-3-oxopropyl)-2-(2-(methylamino)acetoxy)phenyl benzoate hydrochloride, 4-((2S)-3-isopropoxy-2-((((octahydroindolizin-1-yl)oxy)carbonyl)amino)-3-oxopropyl)-1,2-phenylene dibenzoate acetate, 2-(diethylamino)ethyl 2-[(2,6-dichloro-3-methylphenyl)amino]benzoate.acetate, (Z)-2-(diethylaminoethyl)ethyl 2-(5-fluoro-2-methyl-1-(4-methylsulfinyl)benzylidene)-1H-inden-1-yl)acetate.AcOH, 2-(dimethylamino)ethyl 2-(3-phenoxyphenyl) propionate.hydrochloride, S-(2-(dimethylamino)ethyl 2-(3-phenoxyphenyl) propanethioate hydrochloride, 2-(dipropylamino)ethyl 4-acetoxy-2',4'-difluoro-[1,1'-biphenyl]-3-carboxylate hydrochloride, 2-(diethylamino)ethyl 2-(4-isobutylphenyl) propionate hydrochloride, and/or 2-(diethylamino)ethyl 2-acetoxybenzoate hydrochloride, and/or a pharmaceutically acceptable salt thereof; and administering orally an aromatic-L-amino-acid decarboxylase inhibitor selected from carbidopa, benserazide, difluromethyldopa, α-methyldopa, and a pharmaceutical composition thereof;

and/or administering a catechol-O-methyl transferase inhibitor selected from entacapone, tolcapone, and a pharmaceutical composition thereof.

3. The method of claim 2 comprising administering transdermally a pharmaceutical composition comprising (S)-4-(2-amino-3-isopropoxy-3-oxopropyl)-1,2-phenylene dibenzoate and 2-(diethylamino)ethyl 2-acetoxybenzoate, and/or pharmaceutically acceptable salt thereof; and
administering orally an aromatic-L-amino-acid decarboxylase inhibitor selected from carbidopa, benserazide, difluromethyldopa, α-methyldopa, and a pharmaceutical composition thereof; and/or administering a catechol-O-methyl transferase inhibitor selected from entacapone, tolcapone; and a pharmaceutical composition thereof.

4. The method of claim 2 comprising
administering transdermally a pharmaceutical composition comprising (S)-4-(2-amino-3-isopropoxy-3-oxopropyl)-1,2-phenylene dibenzoate, 2-(diethylamino)ethyl 2-acetoxybenzoate, carbidopa and/or entacapone, and/or pharmaceutically acceptable salt thereof; and
administering orally an aromatic-L-amino-acid decarboxylase inhibitor selected from carbidopa, benserazide, difluromethyldopa, α-methyldopa, and a pharmaceutical composition thereof; and/or administering a catechol-O-methyl transferase inhibitor selected from entacapone, tolcapone; and a pharmaceutical composition thereof.

5. The method of claim 2 comprising
administering transdermally a pharmaceutical composition comprising (S)-4-(2-amino-3-oxo-3-(pentan-3-yloxy)propyl)-1,2-phenylene bis(2-methylpropanoate) and 2-(diethylamino)ethyl 2-(4-isobutylphenyl)propionate, and/or pharmaceutically acceptable salt thereof; and
administering orally an aromatic-L-amino-acid decarboxylase inhibitor selected from carbidopa, benserazide, difluromethyldopa, α-methyldopa, and a pharmaceutical composition thereof; and/or administering a catechol-O-methyl transferase inhibitor selected from entacapone, tolcapone; and a pharmaceutical composition thereof.

6. The method of claim 2 comprising
administering transdermally a pharmaceutical composition comprising 4-(2-(((1-((pyrrolidine-2-carbonyl)oxy)ethoxy)amino)ethyl)-1,2,-phenylene dibenzoate and 4-(dimethylamino)butyl 2-(3-phenoxyphenyl) propionate, and/or pharmaceutically acceptable salt thereof; and
administering orally an aromatic-L-amino-acid decarboxylase inhibitor selected from carbidopa, benserazide, difluromethyldopa, α-methyldopa, and a pharmaceutical composition thereof; and/or administering a catechol-O-methyl transferase inhibitor selected from entacapone, tolcapone; and a pharmaceutical composition thereof.

7. The method of claim 2 comprising
administering transdermally a pharmaceutical composition comprising (S)-4-(2-amino-3-oxo-3-(pentan-3-yloxy)propyl)-1,2-phenylene, bis(2-methylpropanoate), 2-(diethylamino)ethyl 2-(4-isobutylphenyl) propionate, carbidopa and/or entacapone, and/or pharmaceutically acceptable salt thereof; and
administering orally an aromatic-L-amino-acid decarboxylase inhibitor selected from carbidopa, benserazide, difluromethyldopa, α-methyldopa, and a pharmaceutical composition thereof; and/or administering a catechol-O-methyl transferase inhibitor selected from entacapone, tolcapone; and a pharmaceutical composition thereof.

8. The method of claim 2 comprising
administering transdermally a pharmaceutical composition comprising (S)-4-(2-amino-3-(heptan-4-yloxy)-3-oxopropyl)-1,2-phenylene dibenzoate, and 2-(dipropylamino)ethyl 4-acetoxy-2',4'-difluoro-[1,1'-biphenyl]-3-carboxylate, and/or pharmaceutically acceptable salt thereof; and
administering orally an aromatic-L-amino-acid decarboxylase inhibitor selected from carbidopa, benserazide, difluromethyldopa, α-methyldopa, and a pharmaceutical composition thereof; and/or administering a catechol-O-methyl transferase inhibitor selected from entacapone, tolcapone; and a pharmaceutical composition thereof.

9. The method of claim 2 comprising
administering transdermally a pharmaceutical composition comprising (S)-4-(2-amino-3-(heptan-4-yloxy)-3-oxopropyl)-1,2-phenylene dibenzoate, and 2-(dipropylamino)ethyl 4-acetoxy-2',4'-difluoro-[1,1'-biphenyl]-3-carboxylate, carbidopa and/or entacapone, and/or pharmaceutically acceptable salt thereof; and
administering orally an aromatic-L-amino-acid decarboxylase inhibitor selected from carbidopa, benserazide, difluromethyldopa, α-methyldopa, and a pharmaceutical composition thereof; and/or administering a catechol-O-methyl transferase inhibitor selected from entacapone, tolcapone; and a pharmaceutical composition thereof.

* * * * *